United States Patent
Barany et al.

(10) Patent No.: US 7,709,201 B2
(45) Date of Patent: May 4, 2010

(54) DETECTION OF NUCLEIC ACID DIFFERENCES USING ENDONUCLEASE CLEAVAGE/LIGASE RESEALING REACTIONS AND CAPILLARY ELECTROPHORESIS OR MICROARRAYS

(75) Inventors: Francis Barany, New York, NY (US);
Hanna Pincas, New York, NY (US);
Jianmin Huang, Jackson Heights, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 480 days.

(21) Appl. No.: 11/574,286

(22) PCT Filed: Aug. 23, 2005

(86) PCT No.: PCT/US2005/029966

§ 371 (c)(1),
(2), (4) Date: Feb. 26, 2007

(87) PCT Pub. No.: WO2006/023919

PCT Pub. Date: Mar. 2, 2006

(65) Prior Publication Data

US 2009/0123913 A1     May 14, 2009

Related U.S. Application Data

(60) Provisional application No. 60/603,937, filed on Aug. 24, 2004, provisional application No. 60/603,855, filed on Aug. 24, 2004.

(51) Int. Cl.
*C12Q 1/68* (2006.01)
(52) U.S. Cl. ......................................... 435/6; 435/91.2
(58) Field of Classification Search ...................... None
See application file for complete search history.

(56) References Cited

U.S. PATENT DOCUMENTS

2003/0148283 A1    8/2003  Barany et al.

FOREIGN PATENT DOCUMENTS

WO    02/44335 A2    6/2002

OTHER PUBLICATIONS

Guo et al., "Methodology for Using a Universal Primer to Label Amplified DNA Segments for Molecular Analysis," Biotechnology Letters 25:2079-83 (2003).
Supplementary Partial European Search Report for European Patent Application No. EP05807317 (Jan. 13, 2009).
Heath et al., "Universal Primer Quantitative Fluorescent Multiplex (UPQFM) PCR: A Method to Detect Major and Minor Rearrangements of the Low Density Lipoprotein Receptor Gene," J. Med. Genet 37:272-280 (2000).
European Examination Report for European Patent Application No. EP05807317, dated June 23, 2009.

*Primary Examiner*—James Martinell
(74) *Attorney, Agent, or Firm*—Nixon Peabody LLP

(57) ABSTRACT

The present invention is directed to various methods for detecting DNA sequence differences, including single nucleotide mutations or polymorphisms, one or more nucleotide insertions, and one or more nucleotide deletions. Labeled heteroduplex PCR fragments containing base mismatches are prepared. Endonuclease cleaves the heteroduplex PCR fragments both at the position containing the variation (one or more mismatched bases) and, to a lesser extent, at non-variant (perfectly matched) positions. Ligation of the cleavage products with a DNA ligase corrects non-variant cleavages and thus substantially reduces background. This is then followed by a detection step in which the reaction products are detected, and the position of the sequence variations are determined.

33 Claims, 27 Drawing Sheets

EndoV / DNA Ligase Mismatch Scanning Assay:
Use of lambda exonuclease to reduce background signal.

1. PCR amplify genes in two independent reactions, using one phosphorylated and one fluorescent primer, and vice versa in the second reaction, with different fluorescent labels, and Taq DNA polymerase. ◆

2. Mix first reaction from test sample with second reaction from reference sample, and vice versa.

3. Treat each PCR product mix with lambda exonuclease ⟩ to form heteroduplexed DNA.

4. Preferentially nick DNA one base to the 3' side of mismatches using thermostable Endonuclease V. ▼

5. Add thermostable ligase ● to re-seal background nicks at perfect match regions. EndoV and ligase reactions may be performed in a single step.

6. Separate fluorescent products using capillary electrophoresis using length standards to determine site of mismatch.

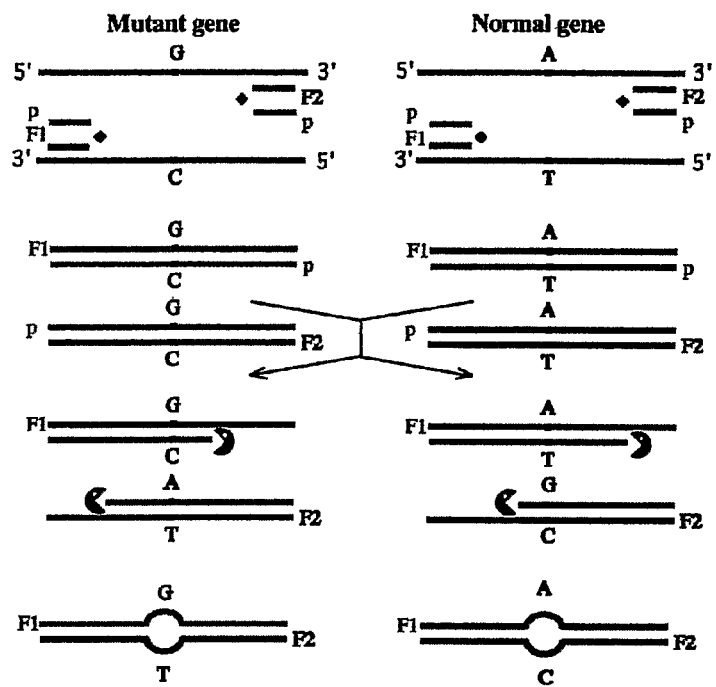

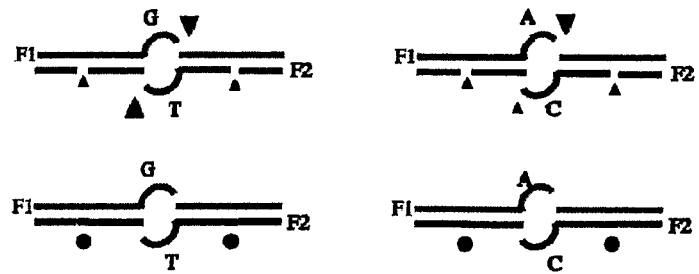

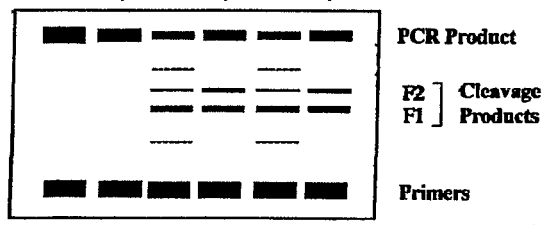

PCR Product

F2 ⎤ Cleavage
F1 ⎦ Products

Primers

Figure 2

**PCR / PCR to prepare heteroduplexed DNA for EndoV mutation scanning
Standard denaturation, renaturation treatment.**

1. PCR amplify one or more fragments of target DNA using a low concentration of gene-specific/universal primers and Taq polymerase. ◆ In the same or a subsequent reaction, a high concentration of labeled universal primers are present, containing the same sequence and additional marker bases on their 3' end. The PCR reaction is continued at a lower temperature and the labeled fragments predominate. Since the two primers share the same sequence, primer dimers do not amplify.

2. In a separate (or the same) reaction, PCR amplify normal DNA as above.

3. Denature and renature products to generate heteroduplexed fragments.

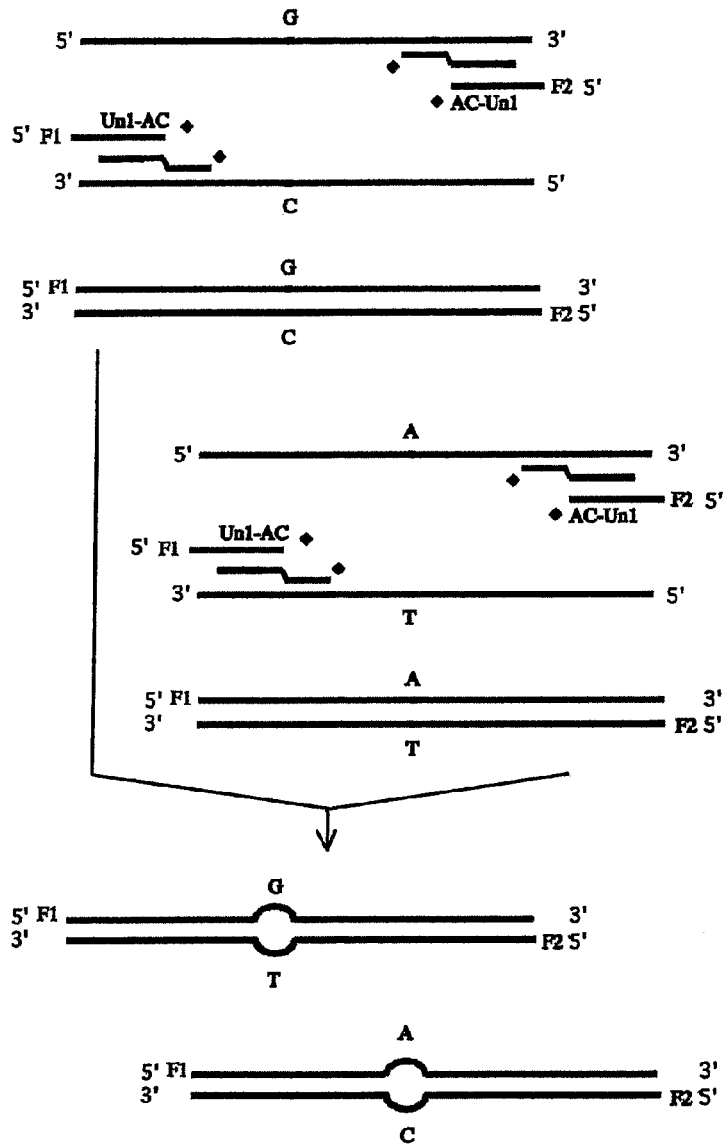

Figure 4

PCR / PCR to prepare heteroduplexed DNA for EndoV mutation scanning Split Label, denaturation, renaturation treatment.

1. PCR amplify one or more fragments of target DNA using a low concentration of gene-specific/universal primers and Taq polymerase. ♦ In the same or a subsequent reaction, a high concentration of one labeled and one unlabeled universal primer are present, containing the same sequence and additional marker bases on their 3' ends. The PCR reaction is continued at a lower temperature and the labeled fragments predominate. Since the two primers share the same sequence, primer dimers do not amplify.

2. In a separate reaction, PCR amplify normal DNA as above, but switch which universal primer is labeled and which is unlabeled.

3. Denature and renature products to generate heteroduplexed fragments.

4. Reverse primer sets to generate complementary heteroduplex set.

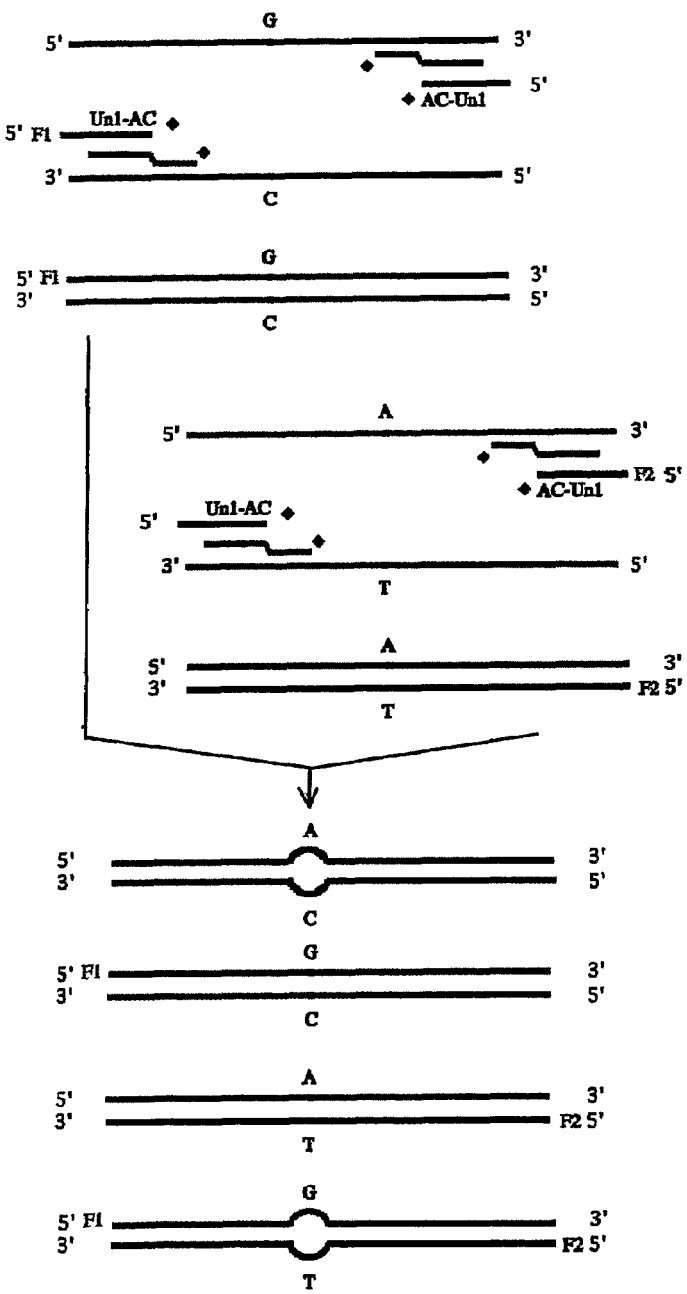

Figure 5

PCR / PCR to prepare heteroduplexed DNA for EndoV mutation scanning Lambda exonuclease treatment.

1. PCR amplify one or more fragments of target DNA using a low concentration of gene-specific/universal primers and Taq polymerase. ♦ In the same or a subsequent reaction, a high concentration of one labeled and one phosphrylated universal primers are present, containing the same sequence and additional marker bases on their 3' ends. The PCR reaction is continued at a lower temperature and the labeled fragments predominate. Since the two primers share the same sequence, primer dimers do not amplify.

2. In a separate reaction, PCR amplify normal DNA as above, but switch which universal primer is labeled and which contains the phosphate group.

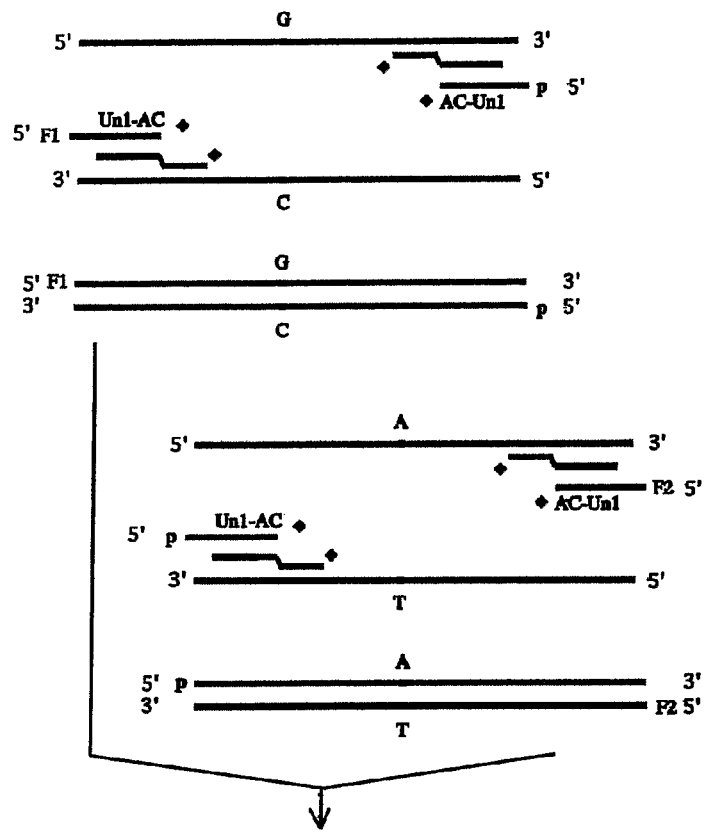

3. Mix the two PCR products, and treat with lambda exonuclease ⟩ to form heteroduplexed DNA.

4. Reverse primer sets to generate complementary heteroduplex set.

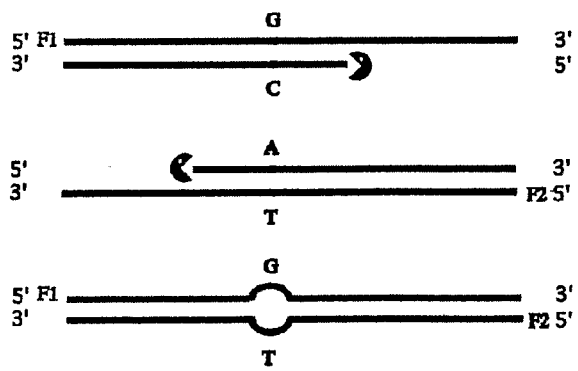

Figure 6

PCR / PCR to prepare heteroduplexed DNA for EndoV mutation scanning Linker ligation treatment.

1. PCR amplify one or more fragments of target DNA using a low concentration of gene-specific/universal primers and Taq polymerase. ♦ In the same or a subsequent reaction, a high concentration of phosphorylated universal primers are present, containing the same sequence and additional marker bases on their 3' end. The PCR reaction is continued at a lower temperature and the phosphorylated fragments predominate. Since the two primers share the same sequence, primer dimers do not amplify.

2. In a separate reaction, PCR amplify normal DNA as above, using universal primers containing additional bases on their 5' ends.

3. Denature and renature products to generate heteroduplexed fragments with asymmetrical "sticky ends". Linkers with corresponding overhangs are ligated with T4 ligase, ● only to the correct heteroduplexed ends. Companion linkers may be used that ligate to ends containing an additional 3' A, often added to the ends of PCR products by Taq polymerase. The linkers contain blocking groups to render the heteroduplexed DNA resistant to a subsequent exonuclease digestion.

4. A separate or the same reaction contains linkers for protection of the complementary heteroduplex.

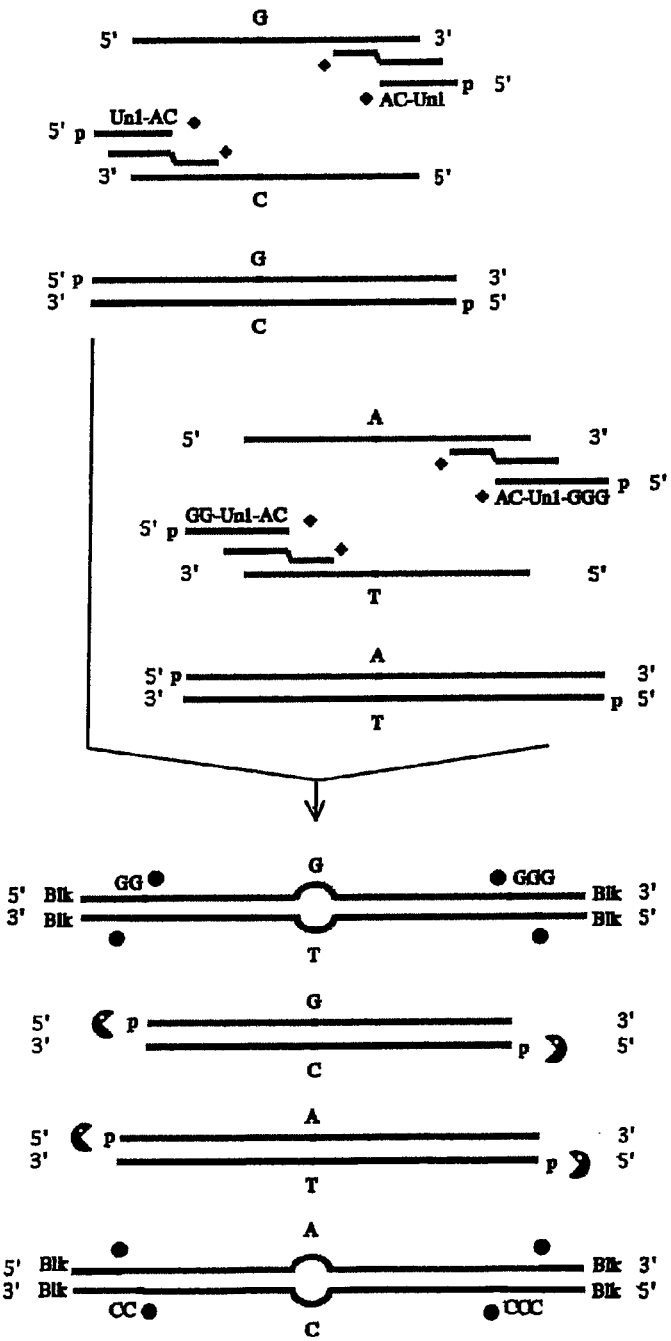

Figure 7

EndoV / DNA Ligase / Array Mutation Screening Assay.
Sequence-specific detection of newly generated 3' ends.

1. Form heteroduplexed DNA. Preferentially nick DNA one base to the 3' side of mismatches using thermostable Endonuclease V. ▼

2. Add thermostable ligase ● to re-seal background nicks at perfect match regions. EndoV and ligase reactions may be performed in a single step.

3. Extend newly generated 3'OH using terminal transferase and dGTP. ■ Anneal primer containing 2 unique bases on 3' end (AT), C8, encoding sequence (E1) and a universal sequence (Un1) on the 5' end, and extend with Taq DNA polymerase. ♦ PCR amplify with gene-specific upstream primer containing a universal sequence (Un2) on the 5' end, phosphorylated Un2 primer, and fluorescently labeled Un1 primer, using Taq DNA polymerase and dNTP's containing a low concentration of dUTP.

4. Nick PCR products one base to the 3' side of uracil bases using Endonuclease V. ▼

5. Digest nicked PCR products using lambda exonuclease ⊃. Only the 5' labeled single-stranded fragment containing approximately 20 to 50 bases of gene-specific sequence adjacent to and including the site of mismatch will remain.

6. Hybridize labeled fragments on array containing tiling of gene sequences to identify approximate position of mismatch. A separate procedure with opposite strand primers would be performed on an array containing complementary sequences to determine presence of mismatches on the complementary strand.

7. The mutation containing fragment(s) may be sequenced individually from the PCR products, by reamplifying with a gene-specific primer and a primer containing a unique encoding sequence E1 and the universal Un1 sequence.

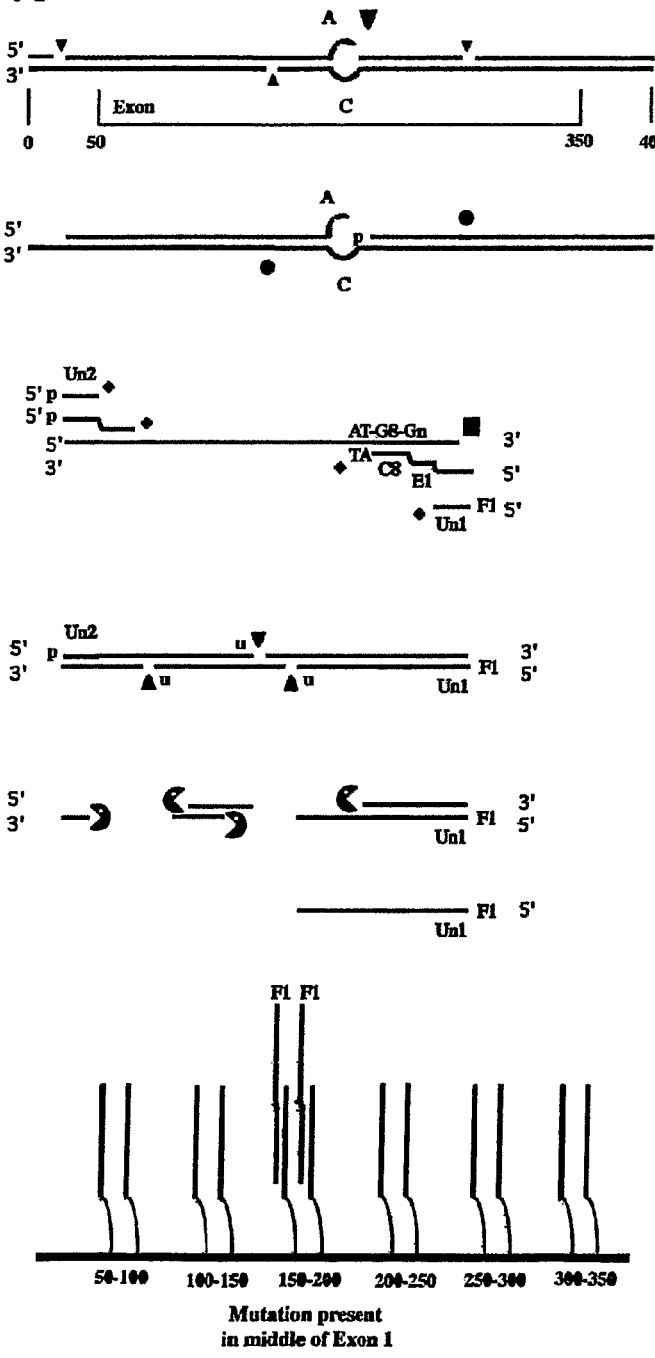

Figure 8

EndoV / DNA Ligase / Array Mutation Screening Assay.
Detection of newly generated 3' ends with multiple exons.

1. Form heteroduplexed DNA. Preferentially nick DNA one base to the 3' side of mismatches using thermostable Endonuclease V. ▼

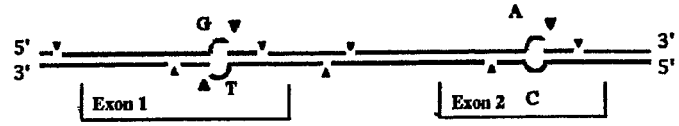

2. Add thermostable ligase ● to re-seal background nicks at perfect match regions. EndoV and ligase reactions may be performed in a single step.

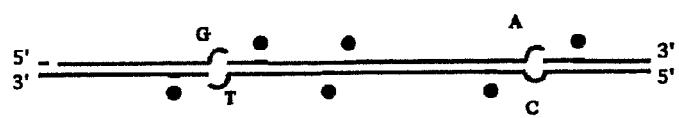

3. Extend newly generated 3'OH using terminal transferase and dGTP. ■ Anneal primer containing 2 unique bases on 3' end (e.g. AC, GT), C8, encoding sequence (e.g. E1, E2) and a universal sequence (Un1) on the 5' end, and extend with Taq DNA polymerase. ◆ PCR amplify with gene-specific primers, upstream of each exon, containing a universal sequence (Un2) on the 5' end, phosphorylated Un2 primer, and fluorescently labeled Un1 primer, using Taq DNA polymerase and dNTP's. Presence of blocking oligos assure the desired PCR products dominate.

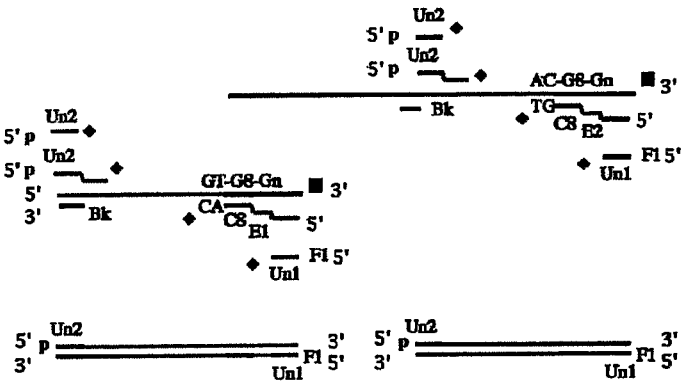

4. Digest PCR products using lambda exonuclease ⊃. Only the 5' labeled single-stranded fragment containing bases of gene-specific sequence adjacent to and including the site of mismatch will remain.

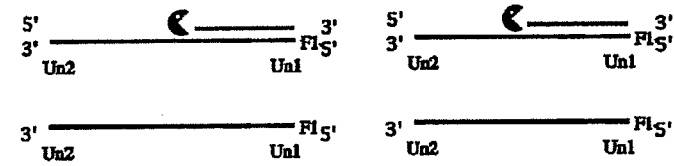

5. Hybridize labeled fragments on array containing tiling of exon sequences to identify exons containing mismatches. A separate procedure with opposite strand primers would be performed on an array containing complementary sequences to determine presence of mismatches on the complementary strand.

6. The mutation containing fragment(s) may be sequenced individually from the PCR products, by reamplifying with an exon-specific primer and a primer containing a unique encoding sequence (e.g. E1, E2) and the universal Un1 sequence.

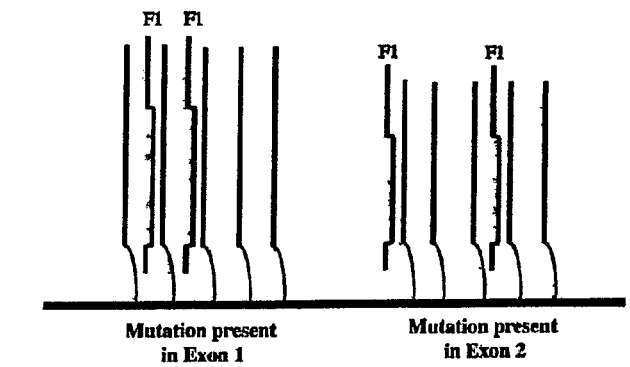

Mutation present in Exon 1    Mutation present in Exon 2

Figure 9

EndoV / DNA Ligase / Array Mutation Screening Assay.
Sequence-specific detection of newly generated 5' ends.

1. Form heteroduplexed DNA. Preferentially nick DNA one base to the 3' side of mismatches using thermostable Endonuclease V. ▼

2. Add thermostable ligase ● to re-seal background nicks at perfect match regions. EndoV and ligase reactions may be performed in a single step 3. Anneal downstream gene-specific primer and extend to create blunt end with newly generated 5' phosphate. Ligate linker containing universal Un1 sequence with T4 ligase ● . PCR amplify with gene-specific downstream primer containing a universal sequence (Un2) on the 5' end, phosphorylated Un2 primer, and fluorescently labeled Un1 primer, using Taq DNA polymerase ◆ and dNTP's containing a low concentration of dUTP.

4. Nick PCR products one base to the 3' side of uracil bases using Endonuclease V. ▼

5. Digest nicked PCR products using lambda exonuclease ⊃ . Only the 5' labeled single-stranded fragment containing approximately 20 to 50 bases of gene-specific sequence one base beyond the site of mismatch will remain.

6. Hybridize labeled fragments on array containing tiling of gene sequences to identify approximate position of mismatch. A separate procedure with opposite strand primers would be performed on an array containing complementary sequences to determine presence of mismatches on the complementary strand.

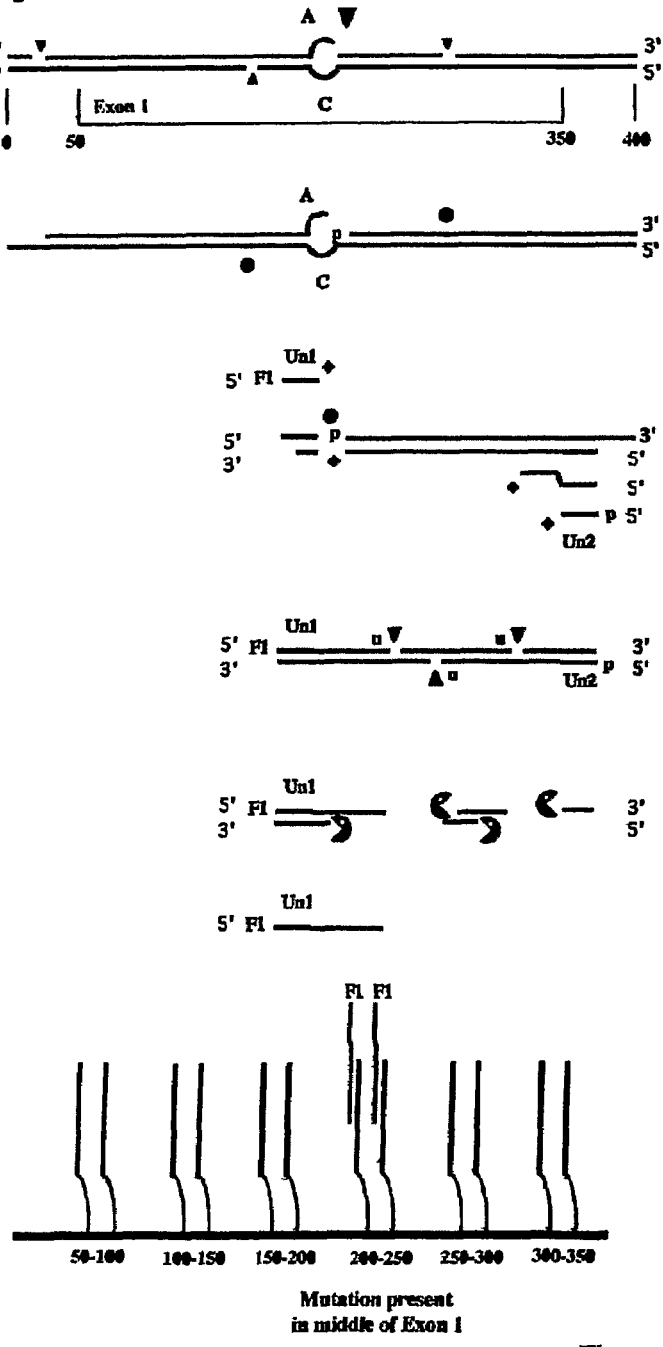

Mutation present
in middle of Exon 1

Figure 10

EndoV / DNA Ligase / Universal Array Mutation Screening Assay.
Detection of newly generated 3' ends.

1. Form heteroduplexed DNA. Preferentially nick DNA one base to the 3' side of mismatches using thermostable Endonuclease V. ▼

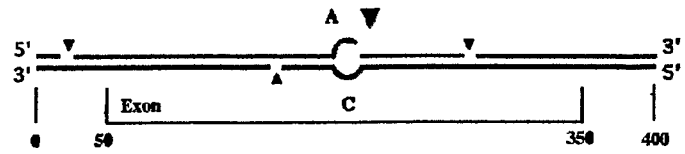

2. Add thermostable ligase ● to re-seal background nicks a perfect match regions. EndoV and ligase reactions may be performed in a single step.

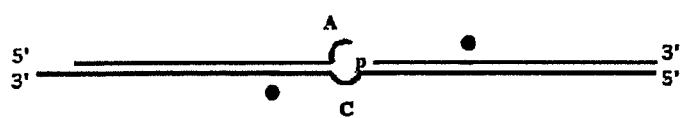

3. Extend newly generated 3'OH using terminal transferase and dGTP. ■ Anneal primer containing 2 unique bases on 3' end (AT), C8, encoding sequence (E1) and a universal sequence (Un1) on the 5' end and extend with Taq DNA polymerase. ◆ PCR amplify with gene-specific upstream primer containing a zipcode sequence and a universal sequence (Un2) on the 5' end, phosphorylated Un2 primer, and fluorescently labeled Un1 primer, using Taq DNA polymerase and dNTP's. Multiple primers with different zipcodes are available but the shortest PCR product dominates.

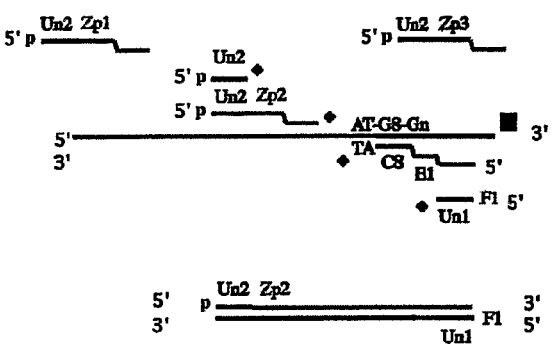

4. Digest PCR products using lambda exonuclease ⊃. Only the 5' labeled single-stranded fragment containing bases of gene-specific sequence adjacent to and including the site of mismatch will remain.

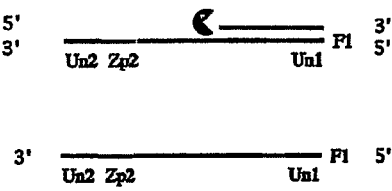

5. Hybridize labeled fragments on universal array containing zipcode sequences to identify approximate position of mismatch. A separate procedure with opposite strand primers would be performed to determine presence of mismatches on the complementary strand.

6. The mutation containing fragment(s) may be sequenced individually from the PCR products, by reamplifying with the specific zipcode primer and a primer containing a unique encoding sequence E1 and the universal Un1 sequence.

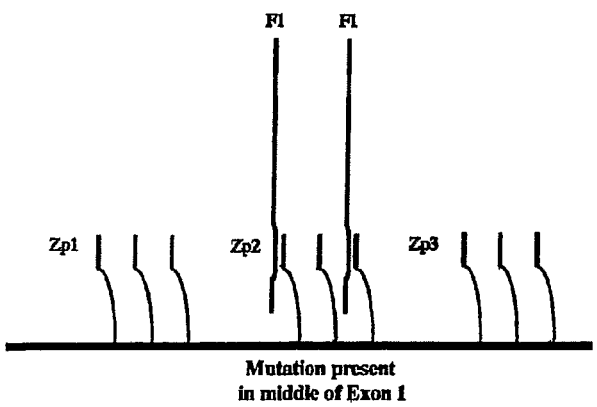

Mutation present in middle of Exon 1

Figure 11

**EndoV / DNA Ligase / Universal Array Mutation Screening Assay.
Detection of newly generated 3' ends with multiple exons and polymorphisms.**

1. Form heteroduplexed DNA. Preferentially nick DNA one base to the 3' side of mismatches using thermostable Endonuclease V. ▼

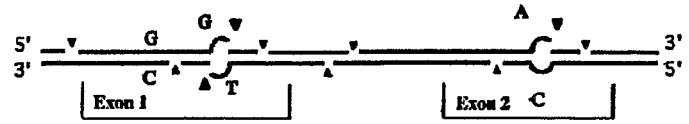

2. Add thermostable ligase ● to re-seal background nicks at perfect match regions. EndoV and ligase reactions may be performed in a single step.

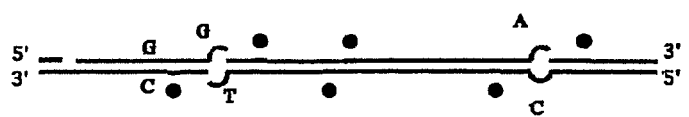

3. Extend newly generated 3'OH using terminal transferase and dGTP. ■ Anneal primers containing 2 unique bases on 3' end (e.g. AC, GT), C8, encoding sequence (e.g. E1, E2) and a universal sequence (Un1) on the 5' end and extend with Taq DNA polymerase ◆. PCR amplify with gene-specific upstream primers containing a zipcode sequence and a universal sequence (Un2) on the 5' end, phosphorylated Un2 primer, and fluorescently labeled Un1 primer, using Taq DNA polymerase and dNTP's. Multiple primers with different zipcodes are available to assure amplification of mutations associated with specific polymorphisms. Presence of blocking oligos assure the desired PCR products dominate.

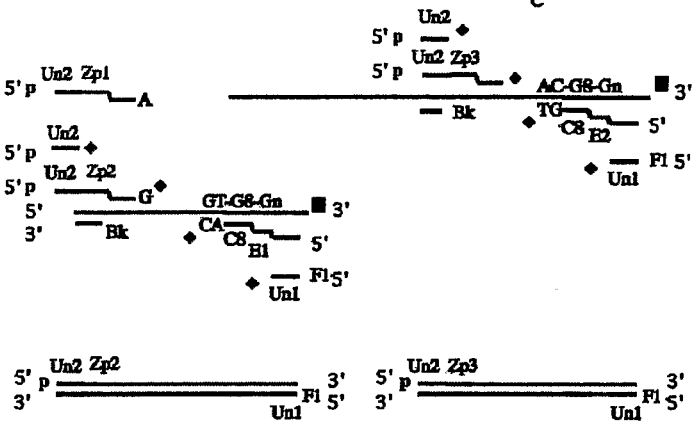

4. Digest PCR products using lambda exonuclease ⟩. Only the 5' labeled single-stranded fragment containing bases of gene-specific sequence adjacent to and including the site of mismatch will remain.

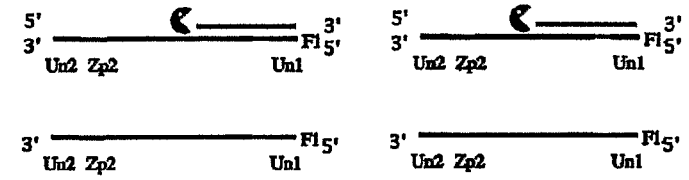

5. Hybridize labeled fragments on universal array containing zipcode sequences to identify approximate position of mismatch. A separate procedure with opposite strand primers would be performed to determine presence of mismatches on the complementary strand.

6. The mutation containing fragment(s) may be sequenced individually from the PCR products, by reamplifying with the specific zipcode primer and a primer containing a unique encoding sequence (e.g. E1, E2) and the universal Un1 sequence.

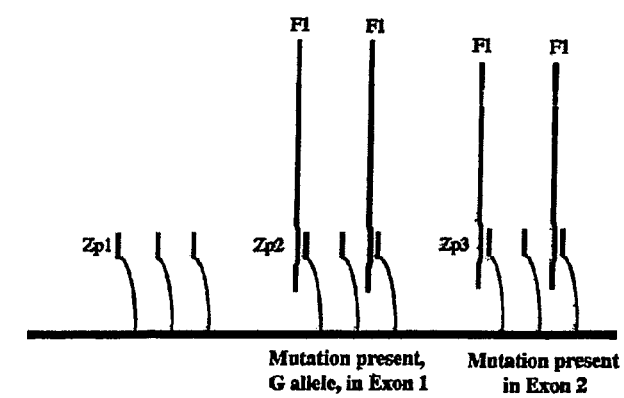

Figure 12

Chemical structure of tetramethylene sulfone and tetramethylene sulfoxide.
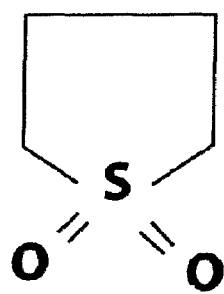
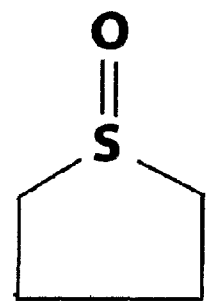
tetramethylene sulfone        tetramethylene sulfoxide
Figure 17

A: PCR primers are 5'VIC-CGCCGC-exon 8 specific sequence, 5'NED-CGCCGC-exon 8 specific sequence.
B: PCR primers are 5'VIC-(2'-O-MeC)$_2$-CGCCGC-exon 8 specific sequence, 5'NED-(2'-O-MeC)$_2$-CGCCGC-exon 8 specific sequence.
C: PCR primers are 5'CCGCCGC-exon 8 specific sequence, 5'CCGCCGC-exon 8 specific sequence.

Figure 20. EndoV cleavage products of p53 exon 6 (Q192Ter, Y205F) fragments generated by PCR: Comparison of internally labeled universal primers and reversed linkage labeled universal primers.

A: PCR primers are 5'-CGCCG-universal sequence, 5'-CGCCG-universal sequence.
B: PCR primers are 3'-VIC-5'-5'-universal sequence, 3'-NED-5'-5'-universal sequence.

SEQUENCE LISTING

<160> NUMBER OF SEQ ID NOS: 36

<210> SEQ ID NO 1
<211> LENGTH: 30
<212> TYPE: DNA
<213> ORGANISM: Artificial
<220> FEATURE:
<223> OTHER INFORMATION: Primer

<400> SEQUENCE: 1
ccccggacag gtaggacctg atttccttac          30

<210> SEQ ID NO 2
<211> LENGTH: 26
<212> TYPE: DNA
<213> ORGANISM: Artificial
<220> FEATURE:
<223> OTHER INFORMATION: Primer

<400> SEQUENCE: 2
ccccgcttct tgtcctgctt gcttac          26

<210> SEQ ID NO 3
<211> LENGTH: 30
<212> TYPE: DNA
<213> ORGANISM: Artificial
<220> FEATURE:
<223> OTHER INFORMATION: Primer

<400> SEQUENCE: 3
ccccggacag gtaggacctg atttccttac          30

<210> SEQ ID NO 4
<211> LENGTH: 26
<212> TYPE: DNA
<213> ORGANISM: Artificial
<220> FEATURE:
<223> OTHER INFORMATION: Primer

<400> SEQUENCE: 4
ccccgcttct tgtcctgctt gcttac          26

<210> SEQ ID NO 5
<211> LENGTH: 19
<212> TYPE: DNA
<213> ORGANISM: Artificial
<220> FEATURE:
<223> OTHER INFORMATION: Primer

<400> SEQUENCE: 5
cgcgtcacga cacgaaaac          19

<210> SEQ ID NO 6
<211> LENGTH: 19
<212> TYPE: DNA
<213> ORGANISM: Artificial
<220> FEATURE:
<223> OTHER INFORMATION: Primer

<400> SEQUENCE: 6
cgcgtcacga cacgaaaca          19

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
cgccgtcacg acacgaaaac                                               20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
cgccgtcacg acacgaaaca                                               20

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ccgccgtcac gacacgaaaa c                                             21

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
ccgccgtcac gacacgaaac a                                             21

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
ccgccgtcac gacacgaaaa c                                             21

<210> SEQ ID NO 12
<211> LENGTH: 21
<212> TYPE: DNA
<213> ORGANISM: Artificial
<220> FEATURE:
<223> OTHER INFORMATION: Primer

<400> SEQUENCE: 12
ccgccgtcac gacacgaaac a                                             21

<210> SEQ ID NO 13
<211> LENGTH: 48
<212> TYPE: DNA
<213> ORGANISM: Artificial
<220> FEATURE:
<223> OTHER INFORMATION: Primer

```
<400> SEQUENCE: 13
cgtcacgaca cgaaaacata gtgtattaac cttatgtgtg acatgttc            48

<210> SEQ ID NO 14
<211> LENGTH: 48
<212> TYPE: DNA
<213> ORGANISM: Artificial
<220> FEATURE:
<223> OTHER INFORMATION: Primer

<400> SEQUENCE: 14
cgtcacgaca cgaaacacaa aatggtcaga gaaacccttta tctgtatc            48

<210> SEQ ID NO 15
<211> LENGTH: 43
<212> TYPE: DNA
<213> ORGANISM: Artificial
<220> FEATURE:
<223> OTHER INFORMATION: Primer

<400> SEQUENCE: 15
cgtcacgaca cgaaaacctc tgattcctca ctgattgctc tta                  43

<210> SEQ ID NO 16
<211> LENGTH: 40
<212> TYPE: DNA
<213> ORGANISM: Artificial
<220> FEATURE:
<223> OTHER INFORMATION: Primer

<400> SEQUENCE: 16
cgtcacgaca cgaaacaggc cactgacaac caccccttaac                     40

<210> SEQ ID NO 17
<211> LENGTH: 38
<212> TYPE: DNA
<213> ORGANISM: Artificial
<220> FEATURE:
<223> OTHER INFORMATION: Primer

<400> SEQUENCE: 17
cgtcacgaca cgaaaaccag ggtggttggg agtagatg                        38

<210> SEQ ID NO 18
<211> LENGTH: 45
<212> TYPE: DNA
<213> ORGANISM: Artificial
<220> FEATURE:
<223> OTHER INFORMATION: Primer

<400> SEQUENCE: 18
cgtcacgaca cgaaacaggt gataaaagtg aatctgaggc ataac                45

<210> SEQ ID NO 19
<211> LENGTH: 38
<212> TYPE: DNA
<213> ORGANISM: Artificial
<220> FEATURE:
<223> OTHER INFORMATION: Primer

<400> SEQUENCE: 19
cgtcacgaca cgaaaactgt ggcttctcct ccacctac                        38
```

<210> SEQ ID NO 20
<211> LENGTH: 37
<212> TYPE: DNA
<213> ORGANISM: Artificial
<220> FEATURE:
<223> OTHER INFORMATION: Primer

<400> SEQUENCE: 20
cgtcacgaca cgaaacagcc ccaattgcag gtaaaac                              37

<210> SEQ ID NO 21
<211> LENGTH: 29
<212> TYPE: DNA
<213> ORGANISM: Artificial
<220> FEATURE:
<223> OTHER INFORMATION: Primer

<400> SEQUENCE: 21
cccggacagg taggacctga tttccttac                                      29

<210> SEQ ID NO 22
<211> LENGTH: 26
<212> TYPE: DNA
<213> ORGANISM: Artificial
<220> FEATURE:
<223> OTHER INFORMATION: Primer

<400> SEQUENCE: 22
ccccgcttct tgtcctgctt gcttac                                         26

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
cgccgcaggg tggttgggag tagatg                                         26

<210> SEQ ID NO 24
<211> LENGTH: 34
<212> TYPE: DNA
<213> ORGANISM: Artificial
<220> FEATURE:
<223> OTHER INFORMATION: Primer

<400> SEQUENCE: 24
cgccgcggtg ataaaagtga atctgaggca taac                                34

<210> SEQ ID NO 25
<211> LENGTH: 26
<212> TYPE: DNA
<213> ORGANISM: Artificial
<220> FEATURE:
<223> OTHER INFORMATION: Primer

<400> SEQUENCE: 25
cgccgcaggg tggttgggag tagatg                                         26

<210> SEQ ID NO 26
<211> LENGTH: 34
<212> TYPE: DNA
<213> ORGANISM: Artificial
<220> FEATURE:
<223> OTHER INFORMATION: Primer

```
<400> SEQUENCE: 26
cgccgcggtg ataaaagtga atctgaggca taac                          34

<210> SEQ ID NO 27
<211> LENGTH: 26
<212> TYPE: DNA
<213> ORGANISM: Artificial
<220> FEATURE:
<223> OTHER INFORMATION: Primer

<400> SEQUENCE: 27
ccgcgcaggg tggttgggag tagatg                                   26

<210> SEQ ID NO 28
<211> LENGTH: 34
<212> TYPE: DNA
<213> ORGANISM: Artificial
<220> FEATURE:
<223> OTHER INFORMATION: Primer

<400> SEQUENCE: 28
ccgcgcggtg ataaaagtga atctgaggca taac                          34

<210> SEQ ID NO 29
<211> LENGTH: 38
<212> TYPE: DNA
<213> ORGANISM: Artificial
<220> FEATURE:
<223> OTHER INFORMATION: Primer

<400> SEQUENCE: 29
tccgcgcata gtgtattaac cttatgtgtg acatgttc                      38

<210> SEQ ID NO 30
<211> LENGTH: 39
<212> TYPE: DNA
<213> ORGANISM: Artificial
<220> FEATURE:
<223> OTHER INFORMATION: Primer

<400> SEQUENCE: 30
ctcggccgca aaatggtcag agaaaccttt atctgtatc                     39

<210> SEQ ID NO 31
<211> LENGTH: 33
<212> TYPE: DNA
<213> ORGANISM: Artificial
<220> FEATURE:
<223> OTHER INFORMATION: Primer

<400> SEQUENCE: 31
tccgcgcctc tgattcctca ctgattgctc tta                           33

<210> SEQ ID NO 32
<211> LENGTH: 30
<212> TYPE: DNA
<213> ORGANISM: Artificial
<220> FEATURE:
<223> OTHER INFORMATION: Primer

<400> SEQUENCE: 32
ctcggccggc cactgacaac caccettaac                               30
```

```
<210> SEQ ID NO 33
<211> LENGTH: 31
<212> TYPE: DNA
<213> ORGANISM: Artificial
<220> FEATURE:
<223> OTHER INFORMATION: Primer

<400> SEQUENCE: 33
tccgcgctgg gcgacagagc gagattccat c                             31

<210> SEQ ID NO 34
<211> LENGTH: 35
<212> TYPE: DNA
<213> ORGANISM: Artificial
<220> FEATURE:
<223> OTHER INFORMATION: Primer

<400> SEQUENCE: 34
ctcggccgtg gatgggtagt agtatggaag aaatc                         35

<210> SEQ ID NO 35
<211> LENGTH: 27
<212> TYPE: DNA
<213> ORGANISM: Artificial
<220> FEATURE:
<223> OTHER INFORMATION: Primer

<400> SEQUENCE: 35
tccgcgcagg gtggttggga gtagatg                                  27

<210> SEQ ID NO 36
<211> LENGTH: 35
<212> TYPE: DNA
<213> ORGANISM: Artificial
<220> FEATURE:
<223> OTHER INFORMATION: Primer

<400> SEQUENCE: 36
ctcggccggt gataaaagtg aatctgaggc ataac                         35
```

DETECTION OF NUCLEIC ACID DIFFERENCES USING ENDONUCLEASE CLEAVAGE/LIGASE RESEALING REACTIONS AND CAPILLARY ELECTROPHORESIS OR MICROARRAYS

This application is a national stage application under 35 U.S.C. ±371 of PCT/US2005/029966, filed Aug. 23, 2005, and claims benefit of U.S. Provisional Patent Application Ser. Nos. 60/603,937, filed Aug. 24, 2004 and 60/603,855, filed Aug. 24, 2004, which are hereby incorporated by reference in their entirety.

The present invention was made with funding from the National Institutes of Health under NCI Grant No. 2 P01 CA65930-05. The U.S. Government may have certain rights in this invention.

FIELD OF THE INVENTION

The present invention is directed to the detection of nucleic acid differences using endonuclease cleavage and ligase resealing reactions in conjunction with electrophoresis or microarrays.

BACKGROUND OF THE INVENTION

Cancer Detection Generally

Each year in the United States, 130,000 new patients are found to have colorectal cancer and 55,000 patients die with metastatic disease even after attempted surgical resection. Despite extensive information about the morphology and the molecular biology of this disease, only a small number of patients actually benefit from this knowledge. It is presently not possible to calibrate therapy to the molecular state of the tumor. Physicians now rely primarily on histological and clinical criteria for developing prognosis and formulating treatment. These predictions are fairly reliable for determining the average outcome of 100 patients. However, there is such large variation from patient to patient, that meaningful individual predictions and treatment stratification are quite difficult.

Thus, patients are confronted with the real possibility that the standard course of adjuvant chemotherapy treatment will be either inadequate or too aggressive for their disease. Not all polyps progress to tumors, and not every carcinoma progresses to metastatic disease.

Consequently, there is an urgent need to change the basis of tumor classification from morphological to molecular characteristics. Such classification should successfully identify those patients with good or poor prognosis, which could not have been distinguished by classical methods. The ultimate goal is to discover reliable molecular markers or targets for the detection, diagnosis, prognosis, and treatment of cancer.

Developing a molecular approach to identifying the risk of progression might permit physicians to allocate the most intense therapy to those patients for whom it is necessary. Conversely, patients with tumors that are destined not to progress, or which are likely to be more sensitive to adjuvant chemotherapy, could be allocated to less intense, less toxic regimens.

The development of microarray technology has allowed for the profiling of thousands of mRNA expression levels and, more recently, has permitted evaluation of changes at the DNA and protein level. This new ability to perform highly parallel analysis of hundreds to thousands of genes and their products, may enable a deeper understanding of the molecular pathways that interact to produce cancer. These newly identified gene products may become targets for new therapies, allowing for the ultimate development of individualized treatments for individual patients.

Despite the successes of microarrays for expression profiling, with notable exceptions, they have been less than successful in predicting patient outcomes or helping to identify new candidate cancer genes. For example, important DNA alterations in known cancer genes (mutations, methylation, gene copy number, allele imbalance, LOH) are frequently not detected by gene expression arrays. To date, DNA changes in individual genes, loss of heterozygosity (LOH), or microsatellite instability (MSI) have been the strongest predictors of prognosis in colon cancer.

Thus, there is an urgent need to profile both DNA and RNA changes on the same tumors. Further, genes that have alterations at both the DNA and RNA level are more likely to be causal to tumor development. Finally, sophisticated mathematical mining of RNA expression profiles for new candidates will likely require stratification of tumors by DNA alterations in known cancer genes.

Genetic Analysis of Solid Tumors

Cancers arise from the accumulation of inherited and/or sporadic mutations in cell cycle, DNA repair, and growth signaling genes. Knowledge of these molecular changes can influence patient management. For instance, members of certain ethnic groups have a higher risk of carrying SNPs in cancer genes, such as BRCCA1, BRCA2 or APC. These SNPs confer an increased risk of developing breast, ovarian, prostate, or colon cancers (Abeliovich, D., et al., *Am J Hum Genet*, 60(3):505-14 (1997); Beller, U., et al., *Gynecol Oncol*, 67(2):123-6 (1997); Berman, D. B., et al., *Cancer Res*, 56(15):3409-14 (1996); Laken, S. J., et al., *Nat Genet*, 17(1): 79-83 (1997); Oddoux, C., et al., *Nat Genet*, 14(2):188-90 (1996); Roa, B. B., et al., *Nat Genet*, 14(2):185-7 (1996); Struewing, J. P., et al., *Nat Genet*, 11(2):198-200 (1995); and Struewing, J. P., et al., *N Engl J Med*, 336(20):1401-8 (1997)) and would benefit from increased vigilance in testing. Sporadic mutations, such as those in the p53 gene, influence both clinical outcome and response to therapy (Broll, R., et al., *Eur J Cancer*, 35(7):1083-8 (1999); Bunz, F., et al., *J Clin Invest*, 104(3):263-9 (1999); Dameron, K. M., et al., *Science*, 265 (5178):1582-4 (1994); Heide, I., et al., *Eur J Cancer*, 33(8): 1314-22 (1997); Prives, C., et al., *J Pathol*, 187(1):112-26 (1999); Tortola, S., et al., *J Clin Oncol*, 17(5):1375-81 (1999); and Zou, Z., et al., *J Biol Chem*, 275(9):6051-4 (2000)). The precise nature of the p53 mutation, therefore, may alter treatment protocols and other clinical considerations (Aurelio, O. N., et al., *Cancer Res*, 58(10):2190-5 (1998); Aurelio, O. N., et al., *Mol Cell Biol*, 20(3):770-8 (2000); Foster, B. A., et al., *Science*, 286(5449):2507-10 (1999); Wang, Y., et al., *Oncogene*, 17(15):1923-30 (1998); and Webley, K. M., et al., *J Pathol*, 191(4):361-7 (2000)). Here, the compilation of mutations occurring in genes from tumor samples is defined as the "mutagenome". Since to date, DNA changes have been the strongest predictors of prognosis in colon cancer, the mutagenome may be the key to more accurate predictors of outcome. Further, it may guide evaluation of expression profiles to identify candidate cancer genes, leading to new targets for cancer therapies.

The utility of any given detection technique needs to be considered in the context of its application. For instance, compared to germline analysis, mutation detection in solid tumors is more difficult. Because solid tumors contain a mixture of both tumor cells and stromal (i.e. non-tumor) cells, a mutation present in the tumor sample may represent only a minor fraction (as little as 15%) of the total DNA. In contrast, when germline SNPs are present, at least half of the sample being tested will contain that variant. As a result, a solid tumor sample requires detection strategies with higher sensitivity.

Polymorphism Detection Technologies

There is a smorgasbord of polymorphism detection technologies available, and their utility depends upon the experimental objectives (and tastes) of the researcher. The most useful criteria for evaluating a given technology include throughput, sensitivity/specificity, quantitative ability, sample requirements, and cost.

Many parameters can increase throughput, such as multiplexing and sample pooling. Multiplexing refers to the ability of an assay to perform multiple reactions simultaneously in the same tube. Assays with very high multiplexing capabilities can process thousands of reactions in parallel (e.g., DNA microarrays). Conversely, assays with low multiplexing capabilities compensate by processing a large number of separate reactions simultaneously (e.g., Taqman assays). SNPs that are of low frequency in a population are less likely to be found when querying germline samples individually. In this case, pooling of samples can increase effective throughput and also increase the chances that a low-frequency SNP is identified per reaction.

In clinical applications, sensitivity (positivity in disease) is defined as the ability of a test to give a positive finding when the patient truly has the disease {Sensitivity=100×(True Positives)/(True Positives+False Negatives)}. As mentioned, technologies used to detect germline polymorphisms in a sample from an individual subject require much lower sensitivity than technologies used to detect sporadic mutations in a solid tumor sample. Pooled germline samples may require greater sensitivity than either of the above. Therefore, different applications can have different sensitivity requirements.

Specificity (negativity in disease) is defined as the ability of a test to give a negative finding when the patient is free of the disease {Specificity=100×(True Negatives)/(True Negatives+False Positives)}. As a result, assays with low specificity are more prone to false positive results. Although false negative and false positive results are both generally undesirable, a false positive tends to be more deleterious. This is because a false negative only removes the sample from its appropriate group, whereas a false positive not only removes the sample from its appropriate group, but also places it in the wrong group; a double error. As a result, it is sometimes prudent to sacrifice sensitivity for greater specificity (Patil, N., et al., *Science*, 294(5547):1719-23. (2001)).

The total number of genotypes that can be performed is limited by the amount of sample available. When sample DNA is in short supply, it can be PCR amplified. However, the PCR step can generate cross contamination artifacts, affecting the overall specificity and sensitivity, and can yield variable multiplexing results, limiting the throughput of the assay. Since the majority of methodologies utilize PCR amplification, development of an alternative method for the high throughput genotyping of low quantity DNA samples (such as from tumor biopsies) would be desirable.

Techniques to Identify Unknown Polymorphisms

SNPs are often of low frequency within a population, so the vast majority of individually queried germline samples will be negative. To address this challenge, unknown samples can be pooled, provided that a highly sensitive technology is used (Halushka, M. K., et al., *Nat Genet*, 22(3):239-47 (1999); Li, W. H., et al., *Genetics*, 129(2):513-23 (1991); and Wang, D. G., et al., *Science*, 280(5366):1077-82 (1998)) (Table 1). Pooling increases the level of throughput, resulting in a higher positive rate per reaction and increasing the chance that an individual reaction will be informative (Shaw, S. H., et al., *Genome Res*, 8(2):111-23 (1998)).

TABLE 1

Comparison of techniques to identify unknown polymorphisms and mutations.

| Technique | Advantages | Current Limitations |
|---|---|---|
| Sanger dideoxy-sequencing | 1) Detects any mutation up to 600 bp/reaction.<br>2) As rapid as SSCP and DGGE but more accurate. | 1) Difficult to detect low level mutations.<br>2) Multiple reactions for large genes. |
| Variation Detection Array (VDA) | 1) High-throughput screen; uses direct hybridization.<br>2) Can screen large sequence blocks. | 1) False positive rate of 11-21% in large scale screens.<br>2) Difficulty detecting polymorphisms in mononucleotide repeats.<br>3) Does not detect frameshift mutations. |
| SSCP | 1) Detects low level mutations.<br>2) Rapid, does not require extra enzymatic steps. | 1) Misses 30% of possible mutations.<br>2) Cannot distinguish missense from silent polymorphisms.<br>3) Does not locate position of polymorphism.<br>4) Can miss mutation near common polymorphism. |
| DGGE, CDGE, DHPLC | 1) Detects low level polymorphisms.<br>2) Rapid, does not require extra enzymatic steps. | 1) Large scale screen missed 13% of polymorphisms.<br>2) Cannot distinguish missense from silent polymorphisms.<br>3) Technically challenging to reproduce results.<br>4) Requires GC clamp; limited to small fragments.<br>5) Does not locate position of polymorphism. |
| ddF, REF | 1) Detects virtually all possible mutations. | 1) Difficult to detect low level mutations.<br>2) Cannot distinguish missense from silent polymorphisms. |
| Cleavase | 1) Heteroduplex not required. | 1) High background.<br>2) Does not locate position of polymorphism.<br>3) Requires optimization for each mutation. |
| Chemical Cleavage (CCM) | 1) Identifies approximate position of mutation.<br>2) High sensitivity. | 1) Labor intensive.<br>2) Chemical hazard. |
| T4 endoVII, MutY | 1) Identifies approximate position of most mutations.<br>2) Identifies missense, frameshift, and nonsense mutations. | 1) Difficult to detect low level mutations.<br>2) High background observed depending on sequence. |
| Thermostable Endonuclease V -DNA Ligase | 1) Identifies approximate position of mutation, identifies 98% of polymorphisms.<br>2) Identifies missense, frameshift, and nonsense mutations, up to 1,750 bp/reaction.<br>3) Detects low level mutations; 1 in 20.<br>4) In combination with sequencing, most rapid screen to directly identify mutation. | 1) Does not detect transition mutations in GGCG or RCGC sequences.<br>2) New technique. |

Direct Sequencing

Sanger dideoxysequencing represents an ideal in unknown polymorphism detection in that it can detect any polymorphism and its position. Unfortunately, direct sequencing has only limited utility for analysis of solid tumors or pooled samples of DNA due to low sensitivity (Yan, H., et al., *Science*, 289(5486):1890-2 (2000)). However, direct sequencing is particularly useful for identifying a polymorphism and its specific position, once a sample is known to contain a polymorphism in a specific area. Furthermore, since many techniques that are capable of identifying the position of a polymorphism are incapable of providing sequence information, Sanger sequencing has utility as a second step to locate and identify the exact base altered in a gene region previously identified as polymorphic.

Electrophoretic Mobility Assays

Classic methods detect unknown polymorphisms by observing the different electrophoretic migration behaviors of homoduplex versus heteroduplex DNA. These methods include single strand conformation polymorphism (SSCP) (Hayashi, K., *PCR Methods Appl*, 1(1):34-8 (1991); Korn, S. H., et al., *J Clin Pathol*, 46(7):621-3 (1993); Makino, R., et al., *PCR Methods Appl*, 2(1):10-3 (1992); and Suzuki, Y., et al., *Oncogene*, 5(7):1037-43 (1990)), denaturing-gradient gel electrophoresis (DGGE) (Fodde, R., et al., *Hum Mutat*, 3(2): 83-94 (1994); Guldberg, P., et al., *Nucleic Acids Res*, 22(5): 880-1 (1994); Ridanpaa, M., et al., *Hum Mol Genet*, 2(6):639-44 (1993); and Ridanpaa, M., et al., *Mutat Res*, 334(3):357-64 (1995)), constant denaturing capillary electrophoresis (CDCE) (Chen, J., et al., *Environ Health Perspect*, 3(227-9 (1994) and Khrapko, K., et al., *Nucleic Acids Res*, 22(3): 364-9 (1994)), dideoxy fingerprinting (ddF) (Sarkar, G., et al., *Genomics*, 13(441-443 (1992)), and restriction endonuclease fragmentation (REF) (Liu, B., et al., *Nat Med*, 1(4): 348-52 (1995)) (See Table 1). A similar approach, denaturing high-performance liquid chromatography (DHPLC), also differentiates homoduplex from heteroduplex DNA, but is based on separation by ion-pair reverse-phase liquid chromatography on alkylated nonporous (styrene divinylbenzene) particles (Underhill, P. A., et al., *Genome Res*, 7(10):996-1005 (1997)). Although these techniques contain some very desirable characteristics, all fall short in either desired throughput or sensitivity for both SNP association studies and mutational analysis of solid tumors. The techniques that can identify the position of a polymorphism (ddF and REF) are not sensitive enough to reliably detect low level polymorphisms in pooled or solid tumor samples. The other techniques are more rapid and can detect low level polymorphisms but do not identify the approximate position of the polymorphism. As a result multiple rounds of dideoxysequencing may be required to identify the sequence of the polymorphism. This greatly reduces throughput capabilities. In addition, these techniques lack the ability to distinguish missense from silent polymorphisms, an essential distinction for tumor analysis.

Microarray

The recent development of DNA microarray technology has established unprecedented levels of throughput. Variation detection arrays (VDA) apply this new technology to scan large sequence blocks and identify regions containing unknown polymorphisms (Halushka, M. K., et al., *Nat Genet*, 22(3):239-47 (1999); Hacia, J. G., et al., *Nature Genetics*, 14(4):441-7 (1996); and Ahrendt, S., et al., *Proc. Natl. Acad. Sci. USA*, 96(7382-7387 (1999)).

The advantage of microarrays is the ability to score hundreds to thousands of signals simultaneously. However, in the current formulation, variation detection arrays miss a high percentage of SNPs and mutations when the position is unknown. Although it is touted as a high-throughput technology, when the position of the mutation is unknown, the need to tile across a large sequence space limits these arrays to just one gene at a time. These chips are particularly deficient in identifying frameshift mutations (Ahrendt, S., et al., *Proc. Natl. Acad. Sci. USA*, 96(7382-7387 (1999); Hacia, J. G., et al., *Nature Genetics*, 14(4):441-7 (1996); and Hacia, J. G., *Nat Genet*, 21(1 Suppl):42-7 (1999)), which occur at high frequency in important tumor suppressor genes such as p53 (10-15%) and APC (70%) (Beroud, C., et al., *Nucleic Acids Res*, 26(1):200-4 (1998) and Beroud, C., et al., *Nucleic Acids Res*, 24(1):121-4 (1996)). Further, since detection of mutations via array hybridization already has too high a rate of false negative signal with germline mutations (Ahrendt, S., et al., *Proc. Natl. Acad. Sci. USA*, 96(7382-7387 (1999)), arrays are just too unreliable to accurately score new mutations in tumor samples where stromal contamination becomes an issue.

This methodology suffers from the same limitations in fabrication and design as observed in known polymorphism analysis, but has demonstrated much greater success in the context of unknown polymorphism detection for both SNP and tumor analysis. For example, in a proof of principle experiment, a GeneChip® (Affymetrix) was used to interrogate lung tumor samples for mutations in p53, a gene mutated in approximately 50% of all cancers. The experiment was performed in a simulated unknown discovery mode and was able to identify 88% of the known missense mutations and 80% of all known polymorphisms (Ahrendt, S., et al., *Proc. Natl. Acad. Sci. USA*, 96:382-7387 (1999)). These results compare with the more traditional method of dideoxysequencing, which detected 76% of the known mutations present. With respect to SNP analysis, a recent study of chromosome 21 successfully identified approximately half of the estimated number of common SNPs (frequency of 10%-50%) across the entire chromosome (Patil, N., et al., *Science*, 294 (5547):1719-23 (2001)). The experimental design required a sacrifice in sensitivity in order to minimize false positives. This explains the decrease in successful identification from 80% to 50% for the chromosome 21 SNP analysis when compared to the lung tumor study previously mentioned. In addition, the utility of this approach needs to be evaluated in the context of rare SNPs (frequency around 1%). Since approximately 50% of the common SNPs in the human genome are refractory to detection by this approach, alternative techniques will most likely be required for a more complete identification of SNPs. Improvements in variant methodologies, such as dynamic allele-specific hybridization (DASH) (Prince, J. A., et al., *Genome Res*, 11(1): 152-62 (2001)) and Microelectric Chip Arrays (Radtkey, R., et al., *Nucleic Acids Res*, 28(7):E17 (2000); Sosnowski, R. G., et al., *Proc Natl Acad Sci USA*, 94(4):1119-23 (1997)), may enhance its utility.

Cleavage

Unknown polymorphisms can also be identified by the cleavage of mismatches in DNA-DNA heteroduplexes. This can be achieved either chemically (Chemical Cleavage Method—CCM) (Cotton, R. G., et al., *Proc Natl Acad Sci USA*, 85(12):4397-401 (1988); Hansen, L. L., et al., *PCR Primer: A Laboratory Manual.*, 275-286 (1995); and Haris, I. I., et al., *PCR Methods Appl*, 3(5):268-71 (1994)), or enzymatically (T4 Endonuclease VII, MutY cleavage, or Cleavase) (Giunta, C., et al., *Diagn Mol Pathol*, 5(4):265-70 (1996); Xu, J. F., et al., *Carcinogenesis*, 17(2):321-6 (1996);

and Youil, R., et al., *Proc Natl Acad Sci USA,* 92(1):87-91 (1995)). Typically, at least two samples are PCR amplified (one sample can be sufficient for solid tumor samples with high levels of stromal contamination), denatured, and then hybridized to create DNA-DNA heteroduplexes of the variant strands. Enzymes cleave adjacent to the mismatch and products are resolved via gel or capillary electrophoresis. Unfortunately, the cleavage enzymes often nick complementary regions of DNA as well. This increases background noise, lowers specificity, and reduces the pooling capacity of the assay.

Cleavage/Ligation

One way to improve signal-to-noise in the cleavage assay is to follow the cleavage with a ligation step to seal spurious nicks. FIG. 1 is a schematic diagram, illustrating this prior procedure for the standard EndoV/ligase mutation scanning assay with detection of fragments by gel electrophoresis. Tet and 6-Fam labeled PCR primers are used to PCR amplify both the mutant and normal genes (in either the same or different reactions). The PCR products are combined, denatured, and reannealed, to form both G/T and A/C heteroduplexed DNA (as well as G:C and A:T homoduplexed DNA, not illustrated). An endonuclease (EndoV) is used to preferentially nick DNA one base to the 3' side of mismatches, while a ligase is used to reseal background nicks at perfect match regions. The products are separated via gel electrophoresis, and the length of the product is used to determine the site of the mutation. Unfortunately, many enzymes that are commonly used to detect mismatches are incompatible with this solution. Enzymes, such as MutY, do not generate re-ligatable ends (Xu, J. F., et al., *Carcinogenesis,* 17(2):321-6 (1996)), while enzymes such as T4 Endonuclease VII or a combination of MutH, MutS, and MutL cleave far from the mismatch (Giunta, C., et al., *Diagn Mol Pathol,* 5(4):265-70 (1996); Youil, R., et al., *Proc Natl Acad Sci USA,* 92(1):87-91 (1995); and Smith, J., et al., *Proc Natl Acad Sci USA,* 93(9):4374-9 (1996)), so ligase would reseal all of the latter nicks. One technique addresses this issue by combining the ability of thermostable Endonuclease V (Endo V) enzyme to recognize and nick mismatched DNA, with the high fidelity of thermostable DNA ligase to suppress nicks at matched DNA (Huang, J., et al., *Oncogene,* 21(12):1909-21 (2002)). Endo V can nick either or both strands of the mismatch. Unlike the previous cleavage enzymes mentioned, Endo V nicks DNA close to the mismatched base (Yao, M., et al., *Journal of Biological Chemistry,* 269(50):31390-6 (1994)). This allows the thermostable ligase to effectively discriminate between perfectly matched and mismatched regions of the DNA (Tong, J., et al., *Nucleic Acids Res,* 27(3):788-94. (1999)) and to ligate only perfectly matched nicks. This results in greatly reduced background noise. This method has very high sensitivity, and can distinguish one mutant sequence in a 20-fold excess of unaltered DNA. Further, since it can locate the approximate position of the polymorphism, it is readily compatible with follow-up dideoxysequencing to identify the exact polymorphism sequence. To date, a few refractory sequences (GGCG and RCGC), where R=purine, have been identified. Nevertheless, evaluation of the SNP database suggests that the combined EndoV/ligase assay is capable of identifying 98% of the polymorphisms typically observed in the human genome (Huang, J., et al., *Oncogene,* 21(12):1909-21 (2002)). Since products are detected by means of electrophoresis, samples are processed sequentially. However, due to its ability to minimize background noise, this technique is more amenable to pooled samples, effectively increasing its throughput capabilities. Overall, since it is a relatively new technique, its reliability and utility need to be established as it is more broadly applied.

The advantage of capillary electrophoresis is the ability to rapidly detect many fragments of different size, similar to gel electrophoresis. Instrumentation for capillary electrophoresis is far more amenable to automation, and is more rapid than gel electrophoresis. However, the EndoV enzyme cleaves the 5' fluorescent label off the PCR products, and these run aberrantly in the capillary, providing a potential for false signal. Thus, there is a need to solve this problem in order to successfully move the EndoV reaction to a capillary electrophoresis readout.

Few tumor samples will have sufficient material to allow for hybridization in the absence of some form of amplification. Amplification from genomic DNA would also be needed to reduce sequence space complexity. If the EndoV/ligase assay were used in conjunction with an array, any primer or incomplete PCR extension product hybridizing to the array would be extended by polymerase. As a result, a false positive signal would be generated. Further, single strand DNA on an array can fold back on itself to form a hairpin. Since polymerase can extend hairpins, false positive signals are generated. Another problem with the Endo V/ligase assay is that EndoV will cleave some heteroduplexed DNAs on both strands. Instead of being a substrate for nick translation, the fragment will fall off the chip, losing signal. EndoV also does not cleave both strands of a heteroduplex with equal intensity. Strands containing the "C" base of a mismatch are not usually nicked. Thus, there is a need to have both Watson & Crick strands on the array and the target. Another problem with the EndoV/ligase assay is that closely related genes like K-ras, N-ras, and H-ras will cross-hybridize to the homologue address. This will result in a false-positive signal being generated. Finally, enzyme reactions on solid surfaces (i.e. microarrays) are difficult due to substrate access, causing protein denaturation problems.

Naturally occurring polymorphisms will also be cleaved by EndoV. As a result, they will be indistinguishable from bona-fide new mutations. In addition, there will be splice site variants which may be difficult to score. The cumulative error rate for reverse transcriptase and PCR will give high background signal. This has the potential of causing false-positives. Since the position of mutations and the intensity of cleavage will influence fluorescent signal strength, it may be difficult to distinguish true-positives from false-positives in the EndoV/ligase assay.

The present invention is directed to overcoming these problems in the art.

SUMMARY OF THE INVENTION

One aspect of the present invention relates to a method for identifying one or more mutant nucleotide target sequences differing by one or more single-base changes, insertions, or deletions, from one or more normal nucleotide target sequences. This involves providing one or more sample(s) potentially containing the normal nucleotide target sequences, one or more mutant nucleotide target sequences, or both. Also provided is a group of one or more primary oligonucleotide primer sets. Each set comprises (a) a first primary oligonucleotide primer, having a target-specific portion and a 5' upstream secondary primer-specific portion, and (b) a second primary oligonucleotide primer, having a target-specific portion and a 5' upstream secondary primer-specific portion. The first primary oligonucleotide primers of each set in a group contain the same 5' upstream secondary primer-specific portion, and the second oligonucleotide primers of each set in a group contain the same 5' upstream secondary primer-specific portion. The sample, the one or more primary oligonucleotide primer sets, and a polymerase are blended to form one or more primary polymerase chain reaction mixture(s). The one or more primary polymerase chain reaction mixture(s) is subjected to one or more polymerase chain reaction cycles to form primary extension products complementary to the normal nucleotide target and mutant nucleotide target sequences present in the sample. A group of one or more secondary oligonucleotide primer sets, each set comprising (a) a first secondary oligonucleotide primer which comprises the same sequence as the 5' upstream secondary primer-specific portion of the first primary oligonucleotide primer, and (b) a second secondary oligonucleotide primer, which comprises the same sequence as the 5' upstream secondary primer-specific portion of the second primary oligonucleotide primer, is also provided. The one or more primary polymerase chain reaction mixture(s), the one or more secondary oligonucleotide primer sets, and a polymerase are blended to form one or more secondary polymerase chain reaction mixture(s). The one or more secondary polymerase chain reaction mixture(s) is subjected to one or more polymerase chain reaction cycles to form secondary extension products complementary to the primary extension products. The polymerase is then inactivated, and the one or more secondary polymerase chain reaction mixture(s) is subjected to a process which converts the secondary extension products to a single-stranded form and anneals the single-stranded secondary extension products to form heteroduplexed products potentially comprising nucleic acid molecules which include nucleotide sequences from the normal nucleotide target sequence and from the mutant nucleotide target sequence. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. After subjecting the ligase resealing reaction mixture to a ligase resealing reaction, products are separated by size or electrophoretic mobility or hybridization to capture probes attached to a solid support. The presence of the normal nucleotide target sequences and the one or more mutant nucleotide target sequences in the sample is detected by distinguishing the separated products.

Another aspect of the present invention relates to a method for identifying one or more mutant nucleotide target sequences differing by one or more single-base changes, insertions, or deletions, from normal nucleotide target sequences. This method involves providing one or more sample(s) potentially containing the normal nucleotide target sequence, one or more mutant nucleotide target sequences, or both. Also provided is a group of one or more primary oligonucleotide primer sets, each set characterized by (a) a first oligonucleotide primer, having a target-specific portion, and (b) a second oligonucleotide primer, having a target-specific portion, where only one of the primary oligonucleotide primers is provided with a label. A polymerase is provided, and the sample, the primary oligonucleotide primer sets, and the polymerase are blended to form one or more primary polymerase chain reaction mixture(s). The primary polymerase chain reaction mixture is subjected to one or more polymerase chain reaction cycles to form primary extension products complementary to the normal nucleotide target sequence and the mutant nucleotide target sequences are present in the sample. The polymerase is inactivated, and the primary polymerase chain reaction mixture(s) is subjected to a process which converts the primary extension products to a single-stranded form and anneals the single-stranded primary extension products to form heteroduplexed products potentially comprising nucleic acid molecules which include nucleotide sequences from the normal nucleotide target sequence and the mutant nucleotide target sequences. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves the heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. Products resulting from subjecting the ligase resealing reaction mixture to a ligase resealing reaction are separated by size or electrophoretic mobility. The presence of the normal nucleotide target sequences and the one or more mutant nucleotide sequences are detected in the sample by distinguishing the separated products resulting from the ligase resealing reaction.

Another aspect of the present invention relates to a method for identifying one or more mutant nucleotide target sequences differing by one or more single-base changes, insertions, or deletions, from a normal nucleotide target sequence. This method involves providing one or more sample(s) potentially containing the normal nucleotide target sequences, one or more mutant nucleotide target sequences, or both. This involves providing a group of one or more primary oligonucleotide primer sets, each set characterized by (a) a first oligonucleotide primer, having a target-specific portion, and (b) a second oligonucleotide primer, having a target-specific portion, where only one of the primary oligonucleotide primers is provided with a label. A polymerase is provided, and the sample, the primary oligonucleotide primer sets, and a polymerase are blended to form one or more primary polymerase chain reaction mixture(s). The primary polymerase chain reaction mixture is subjected to one or more polymerase chain reaction cycles to form primary extension products complementary to the normal nucleotide target sequence and the mutant nucleotide target sequence present in the sample. The polymerase is inactivated, and the primary polymerase chain reaction mixture(s) is subjected to a process which converts the secondary extension products to a single-stranded form and anneals the single-stranded secondary extension products to form heteroduplexed products potentially comprising nucleic acid molecules which include nucleotide sequences from the normal nucleotide target sequence and from the mutant nucleotide target sequences.

An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves the heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. A terminal transferase is provided, and the potentially nicked or cleaved heteroduplexed products from the ligase resealing reaction mixture and the terminal transferase are blended to form a terminal transferase extension reaction mixture. The terminal transferase extension reaction mixture is incubated with a single dNTP to extend nicked or cleaved heteroduplexed products at newly generated 3' OH groups to form terminal transferase extension products. One or more tertiary oligonucleotide primers suitable for hybridization to the newly generated terminal transferase extension products and suitable for 3' end extension are provided. The terminal transferase extension products, the tertiary oligonucleotide primers, and a polymerase are blended to form a tertiary polymerase extension reaction mixture. The tertiary polymerase extension reaction mixture is incubated under conditions allowing the tertiary oligonucleotide primers to hybridize to the terminal transferase extension products, and polymerase to produce tertiary extension products, which are complementary copies of the terminal transferase extension products, containing sites of mismatch and adjacent target-specific sequences. A group of one or more quaternary oligonucleotide primer sets, each set characterized by (a) a first quaternary oligonucleotide primer, having a tertiary extension product-specific portion and a 5' upstream quintenary primer-specific portion, and (b) a second quaternary oligonucleotide primer, having a tertiary extension product-specific portion and a 5' upstream quintenary primer-specific portion. The tertiary extension products, the quaternary oligonucleotide primers, and a polymerase are blended to form one or more quaternary extension reaction mixture(s). The one or more quaternary polymerase chain reaction mixture(s) is subjected to one or more quaternary polymerase chain reaction cycles to form a quaternary extension product. A group of one or more quintenary oligonucleotide primer sets, each set characterized by (a) a first quintenary oligonucleotide primer, having the same sequence as the 5' upstream portion of the first quaternary oligonucleotide primer, and (b) a second quintenary oligonucleotide primer, containing the same sequence as the 5' upstream portion of the second quaternary oligonucleotide, is provided. The quaternary extension product, the group of one or more quintenary oligonucleotide primer sets, and a polymerase are blended to form a quintenary polymerase chain reaction mixture(s). The quintenary polymerase chain reaction mixture(s) is subjected to one or more quintenary polymerase chain reaction cycles to form a quintenary extension product complementary to the quaternary extension product. Products resulting from subjecting the ligase resealing reaction mixture to a ligase resealing reaction are separated by size or electrophoretic mobility or hybridization to capture probes attached to a solid support. The presence of the normal nucleotide target sequence and the one or more mutant nucleotide target sequences in the sample are detected by distinguishing the separated products resulting from the ligase resealing reaction.

Another aspect of the present invention relates to a method for identifying one or more mutant nucleotide target sequences differing by one or more single-base changes, insertions, or deletions, from normal nucleotide target sequences. This involves providing one or more sample(s) potentially containing the normal nucleotide target sequences, one or more mutant nucleotide target sequences, or both. Also provided is a group of one or more primary oligonucleotide primer sets, each set characterized by (a) a first oligonucleotide primer, having a target-specific portion, and (b) a second oligonucleotide primer, having a target-specific portion. Only one of the primary oligonucleotide primers is provided with a label. A polymerase is provided, and the sample, the primary oligonucleotide primer sets, and the polymerase are blended to form one or more primary polymerase chain reaction mixture(s). The primary polymerase chain reaction mixture is subjected to one or more polymerase chain reaction cycles to form primary extension products complementary to the normal nucleotide target sequences and the mutant nucleotide target sequences present in the sample. The polymerase is inactivated, and the primary polymerase chain reaction mixture(s) is subjected to a process which converts the primary extension products to a single-stranded form and anneals the single-stranded primary extension products to form heteroduplexed products potentially comprising nucleic acid molecules which include nucleotide sequences from the normal nucleotide target sequences and from the mutant nucleotide sequences. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves the heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. One or more tertiary oligonucleotide primers suitable for hybridization to the 5' end of a strand of the nicked heteroduplex products which have been sealed is provided, and the ligase resealing reaction mixture after resealing, the tertiary oligonucleotide primers, and a polymerase are blended to form a tertiary polymerase extension reaction mixture. The tertiary polymerase extension reaction mixture is incubated under conditions allowing for the tertiary oligonucleotide primers to hybridize to a strand of the nicked heteroduplex products which has been sealed and the polymerase to produce tertiary extension products. A blunt end linker and a ligase with blunt end activity are provided. The tertiary extension products, the blunt end linker, and the ligase with blunt end activity are blended to form a blunt end ligase reaction mixture. The blunt end ligase reaction mixture is incubated under conditions effective to ligate the blunt end linker to tertiary extension products and produce blunt end ligation products. A plurality of quaternary oligonucleotide primer sets, each set characterized by (a) a first quaternary oligonucleotide primer, having a blunt end ligation product-specific portion and a 5' upstream quintenary primer-specific portion, and (b) a second quaternary oligonucleotide primer, having a linker-specific portion, is provided. The blunt end ligation products, the quaternary oligonucleotide primer sets, and a polymerase are blended to form one or more quaternary polymerase chain reaction mixture(s). The one or more quaternary polymerase chain reaction mixture(s) is subjected to one or more polymerase chain reaction cycles to form a quaternary extension product. A quintenary oligonucleotide primer, having the same sequence as the 5' upstream portion of a first quaternary oligonucleotide primer, is provided, and the quintenary oligonucleotide primer, quaternary polymerase extension product, and a polymerase are blended to form a quintenary polymerase chain reaction mixture. The one or more quintenary polymerase chain reaction mixture is subjected to one or more polymerase chain reaction cycles to form a quintenary extension product. Products resulting from subjecting the one or more quintenary polymerase chain reaction mixture to one or more polymerase chain reaction cycles are separated by size or electrophoretic mobility or hybridization to capture probes attached to a solid support. The presence of the normal nucleotide target sequences and the one or more mutant nucleotide target sequences in the sample is detected by distinguishing the separated products resulting from the quintenary polymerase chain reaction.

The advantages of the EndoV/ligase mutation scanning assay are most apparent when detecting mutations in tumor samples (Huang, J., et al., *Oncogene,* 21(12):1909-21 (2002), which is hereby incorporated by reference in its entirety). The technique not only can readily identify frameshift mutations, but also can detect the presence of mutations in an excess of wild-type DNA, precisely the condition observed with most solid tumor samples. However, since the products are detected by electrophoresis, genes are processed sequentially.

There are hundreds of known tumor suppressor genes and dozens of known oncogenes that may undergo mutations during tumor development. Current technology is inadequate for rapidly surveying these genes to identify the key tumor suppressor genes that underwent inactivating point or frameshift mutations, or the key oncogenes that underwent activating mutations. Further, for clinical diagnosis and prognosis, the technology should be both sensitive and specific, i.e. identify all the genes with new mutations, identify all mutations when present in the gene, and limit the number of putative mutations that are not verified by a subsequent sequencing step. Thus, there is an urgent need to accurately identify the "mutagenome" of a tumor sample.

Related to the identification of new mutations that arise sporadically in tumors is the identification of germline mutations that predispose individuals to developing cancers in the first place. Again, there are hundreds of candidate genes that would need to be rapidly profiled for the presence of both common and uncommon SNPs and mutations.

One approach would be to combine the EndoV/ligase mutation scanning technology with microarray technology. The idea here is not to necessarily identify within a base pair the exact nature of a mutation, but to identify the genes or exons that contain a potential mutation on a microarray, and then pinpoint the mutation using EndoV/ligase mutation scanning with electrophoretic separation and ultimately automated sequencing. A simple statement of the idea is to take a sample of cDNA and hybridize to a cDNA chip. Heteroduplexes are nicked with EndoV at positions of base mismatches (with nicks at perfect matches resealed by ligase), and the nicked fragments labeled by nick translation using DNA polymerase and fluorescent dNTPs. Those addresses that show fluorescent label identify the particular cDNAs containing the original mutations. A similar approach could be considered using genome fragments in the sample and hybridizing them to complementary fragments that have been spotted on a microarray.

The EndoV reaction of the present invention takes place in solution and does not fall off the chip. Further, since the labeling scheme does not depend on nick translation, cleavage of both strands of the substrate does not interfere with generating the correct signal. The Watson & Crick strands are analyzed independently in different reactions. In some embodiments of the present invention, the array is made from synthetic oligonucleotides, cDNA, or PCR fragments complementary to the strand that is being scored. In other embodiments, a universal array is used to score each reaction separately or, after completion of the PCR step, they may be mixed and hybridized to a single array, provided different addresses are used on the array for each independent strand reaction.

If the mutation is at a different 50 bp region, then they will be easily distinguished as two addresses will light up. If the mutation is in the same 50 bp region, signal may light up differently in tumor vs. normal sample or when co-hybridizing two different labeled signal. If detection schemes are used with a Q-zipcode sequence attached to the 3' end of the fragment, the additional two bases on the end of the extension primer allow for a unique labeling scheme. Since both the Watson and Crick strands are interrogated, most mutations will be distinguished from the mutation, except in the rare cases where the surrounding bases are identical (on average 1 in 64 cases). Allele-specific PCR primers for each known polymorphism may also be used to score new mutations close to an existing polymorphism.

In order to score splice variants, both normal and splice site variant have regions that are both amplified with a given primer set.

The use of different sets of arrays and amplifications and mixing in separate tubes can prevent cross-hybridization of closely related genes to homologue addresses, resulting in a false positive signal.

A capping scheme is provided that captures heteroduplexed products containing only full length PCR extension product. The procedure also removes the problem of false positive signal from a full length free 3' OH end. Generally, incomplete PCR amplification is not a problem and does not generate sufficient background noise. The labeled products that indicate presence of a mutation are PCR amplified using specific primers that are inset from about 20 to 60 bases from the original primers used to generate the heteroduplexed products.

By using multiple 50 mer sequences to tile across a region, noise is divided by the number of addresses used to tile the targeted region. Proofreading enzymes may also be used to further reduce noise, if needed.

Q-Zipcode labeling gives same strength signal independent of position. For the universal array detection scheme, products are PCR amplified prior to scoring on the array. This may help even out intensities.

With the present invention, single stranded DNA on an array cannot fold back on itself and permit polymerase to extend hairpins. This all avoids producing a false positive signal.

Enzyme reactions in the present invention work in solution, not on the array.

BRIEF DESCRIPTION OF THE DRAWINGS

FIG. 2 is a schematic drawing, illustrating an EndoV/Ligase mutation scanning assay in accordance with the present invention which uses lambda exonuclease to reduce background signal.

FIG. 4 is a schematic drawing, illustrating an EndoV/Ligase mutation scanning assay in accordance with the present invention which uses PCR/PCR to prepare heteroduplexed DNA and standard denaturation and renaturation treatments.

FIG. 5 is a schematic drawing, illustrating an EndoV/Ligase mutation scanning assay in accordance with the present invention, which uses PCR/PCR to prepare heteroduplexed DNA for EndoV mutation scanning and split label denaturation and renaturation treatments.

FIG. 6 is a schematic drawing, illustrating an EndoV/Ligase mutation scanning assay in accordance with the present invention, which uses PCR/PCR to prepare heteroduplexed DNA for EndoV mutation scanning and lambda exonuclease treatment.

FIG. 7 is a schematic drawing, illustrating an EndoV/Ligase mutation scanning assay in accordance with the present invention, which uses PCR/PCR to prepare heteroduplexed DNA for EndoV mutation scanning and linker ligation treatment.

FIG. 8 is a schematic drawing, illustrating an EndoV/DNA Ligase/Array mutation screening assay in accordance with the present invention, which uses sequence-specific detection of newly generated 3' ends.

FIG. 9 is a schematic drawing, illustrating an EndoV/DNA Ligase/Array mutation screening assay in accordance with the present invention, which detects newly generated 3' ends with multiple exons.

FIG. 10 is a schematic drawing, illustrating an EndoV/DNA Ligase/Array mutation screening assay in accordance with the present invention, which uses sequence-specific detection of newly generated 5' ends.

FIG. 11 is a schematic drawing, illustrating an EndoV/DNA Ligase/Universal Array mutation screening assay in accordance with the present invention, which uses detection of newly generated 3' ends.

FIG. 12 is a schematic drawing, illustrating an EndoV/DNA Ligase/Universal Array mutation screening assay in accordance with the present invention, which uses detection of newly generated 3' ends with multiple exons and polymorphisms.

In FIG. 15A, the results obtained on p53 exon 8 are displayed, when using either VicUniEV1F and NedUniEV2R PCR primers (internally-labeled), or VicUniEV5F and NedUniEV6R PCR primers (reverse linkage-labeled) to PCR amplify both wild-type and R273H mutation, as indicated (See FIG. 4). For the lambda exonuclease treatment, one of the labeled universal primers was replaced with a phosphorylated primer to allow for digestion of that strand (See FIG. 6). Under the standard denaturation/renaturation conditions, wild-type/mutant PCR mixtures contain heteroduplexes with G/T+A/C mismatches. Wild-type PCR fragments were used as controls (G:C match). With the lambda exonuclease procedure, two distinct types of wild-type/mutant PCR mixtures were subjected to the EndoV reaction: heteroduplexes of top strand wild-type with bottom strand mutant (G/T mismatch)

and heteroduplexes of top strand mutant with bottom strand wild-type (A/C mismatch). Wild-type PCR mixtures were used as controls (G:C match).

FIGS. 16A-B are electrophoretograms of EndoV/Ligase cleavage products obtained on heteroduplexed DNA fragments of different sizes containing the p53 exon 8 R273H mutation. In FIG. 16A, the results obtained on p53 exon 8 R273H are displayed, when using 3 different heteroduplexing conditions, as indicated. Under the standard conditions, wild-type/mutant PCR mixtures contain heteroduplexes with G/T+A/C mismatches. Wild-type PCR fragments were used as controls (G:C match). Under the lambda exonuclease procedure, two distinct types of wild-type/mutant PCR mixtures were subjected to the EndoV reaction: heteroduplexes of top strand wild-type with bottom strand mutant (G/T mismatch) and heteroduplexes of top strand mutant with bottom strand wild-type (A/C mismatch). Wild-type PCR mixtures were used as controls (G:C match). Under the "split label, denaturation/renaturation" procedure, two distinct types of labeled wild-type/mutant PCR mixtures were denatured, reannealed, and then subjected to the EndoV reaction: heteroduplexes of top strand wild-type with bottom strand mutant (only G/T mismatch labeled) and heteroduplexes of top strand mutant with bottom strand wild-type (only A/C mismatch labeled). Wild-type PCR mixtures were used as controls (G:C match). In FIG. 16B, results obtained on p53 exons 8-9 R73H are displayed, when using standard and lambda exonuclease heteroduplexing methods, as indicated. Under the standard conditions, wild-type/mutant PCR mixtures contain heteroduplexes with G/T+A/C mismatches. Wild-type PCR fragments were used as controls (G:C match). Under the lambda exonuclease procedure, two distinct types of wild-type/mutant PCR mixtures were subjected to the EndoV reaction: heteroduplexes of top strand wild-type with bottom strand mutant (G/T mismatch) and heteroduplexes of top strand mutant with bottom strand wild-type (A/C mismatch). Wild-type PCR mixtures were used as controls (G:C match). Reaction mixtures were electrophoresed on the ABI 3730 fluorescence-based capillary electrophoresis instrument (Applied Biosystems, Foster City, Calif.). At completion of the electrophoretic run, a virtual gel image was displayed on the instrument monitor, with Vic- and Ned-labeled fragments appearing in green and yellow, respectively. Data analysis was achieved using Gene Mapper fragment analysis software.

FIG. 17 is a drawing of the chemical structures of tetramethylene sulfone and tetramethylene sulfoxide.

As shown in FIG. 18, the numbers above the electrophoretogram (1-10) indicate different variations of the standard reaction conditions as follows:

Condition 1: Standard conditions for generating heteroduplexes (95° C., 2 min., slow cool to 45° C. over 1 hour) and EndoV reactions (5% DMSO and 1.5 M betaine);

Condition 2: 4 mM EDTA (final concentration) was added during the heteroduplex formation incubation step;

Condition 3: 5% tetramethylene sulfoxide was added during the EndoV cleavage step;

Condition 4: 4 mM: EDTA was added during the heteroduplex formation incubation step. 5% tetramethylene sulfoxide was added during the EndoV cleavage step;

Condition 5: 5% tetramethylene sulfone was added during the EndoV cleavage step;

Condition 6: 4 mM EDTA was added during the heteroduplex formation incubation step, 5% tetramethylene sulfone was added during the EndoV cleavage step;

Condition 7: 10% tetramethylene sulfoxide was added during the heteroduplex formation incubation step. 5% tetramethylene sulfoxide was present during the EndoV cleavage step;

Condition 8: 10% tetramethylene sulfoxide and 4 mM EDTA were added during the heteroduplex formation incubation step. Final concentration of 5% tetramethylene sulfoxide was present in the EndoV reaction mixture;

Condition 9: 10% tetramethylene sulfone was added during the heteroduplex formation incubation step. Final concentration of 5% tetramethylene sulfone was present during the EndoV cleavage step; and Condition 10: 10% tetramethylene sulfone and 4 mM EDTA were added during the heteroduplex formation incubation step. Final concentration of 5% tetramethylene sulfone was present during the EndoV cleavage step.

The cleavage products of upper and lower strand of the R273H mutation are indicated with arrows. Different additives are shown as (+) for the different lanes. W: wild-type. M: mutant. Tfx: tetramethylene sulfoxide. Tfo: tetramethylene sulfone.

Figure 3:
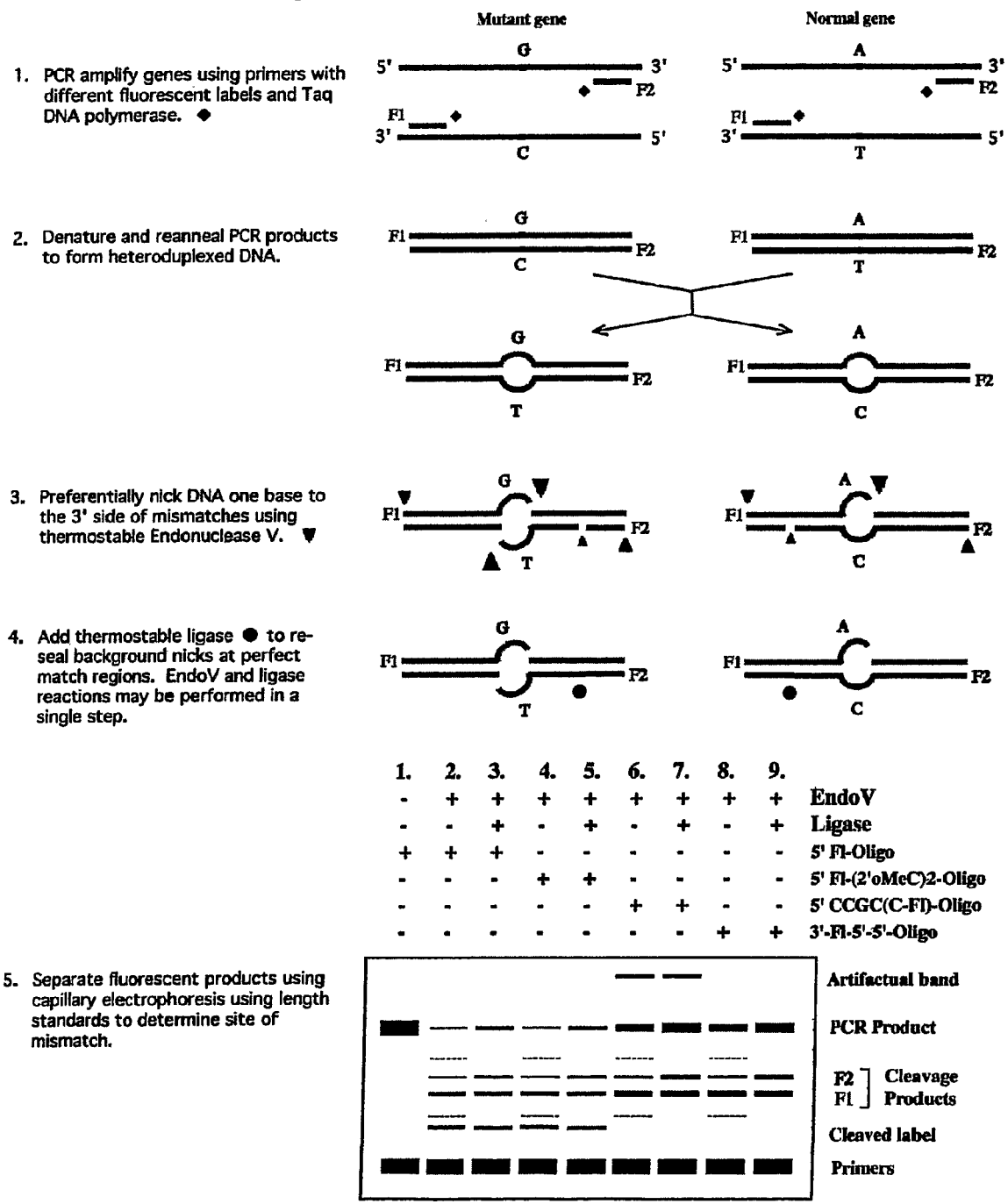
FIG. 3 is a schematic drawing, illustrating an EndoV/Ligase mutation scanning assay in accordance with the present invention which reduces 5' end cleavage.
Figure 19:
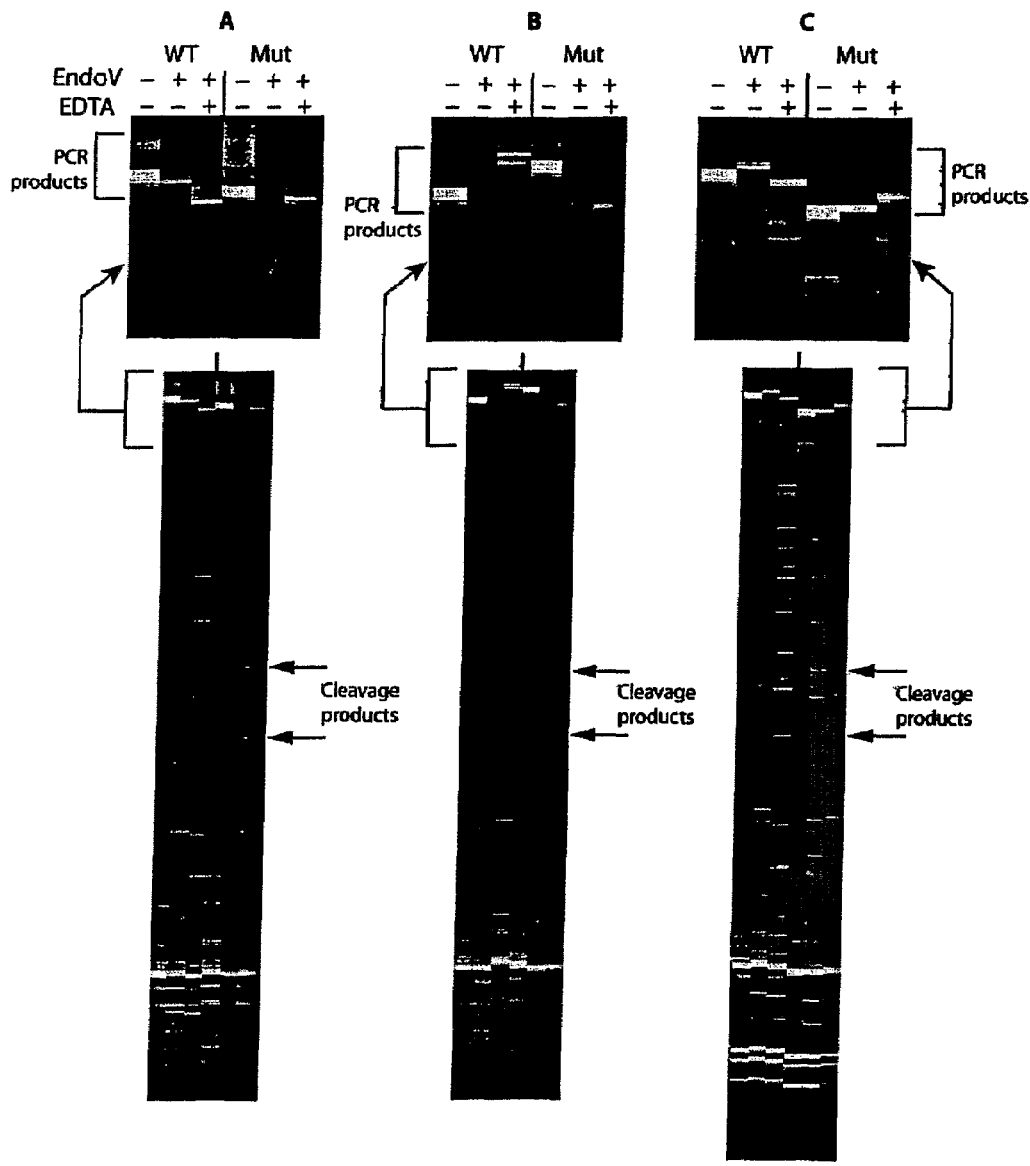

FIGS. 19A-C are a display of capillary electrophoretic results of EndoV cleavage products of p53 exon 8 (R273H mutation) fragments generated by PCR primers containing different modifications. Fragments were PCR amplified, denatured, and renatured as illustrated in FIG. 3. EndoV cleavage products of heteroduplex PCR fragments amplified with different modified primers were visualized in an ABI 3730 after electrophoresis. In FIG. 19A, primers designed to amplify p53 exon 8 were modified with adding the EndoV resistant sequence "CGCCGC" to the 5' end of each primer. In FIG. 19B, primers were modified by attaching the label on the 5' end through two 2'O methyl-C bases followed by the resistant sequence CGCCGC. In FIG. 19C, primers were modified by attaching the label through a C-c6-Vic (or Ned) linkage at the 5th position 5' from the end of the primer (see bottom of FIG. 19). The top image in each of FIGS. 19A-C is an enlargement of the top part of the gel image. The arrows indicate the cleavage products generated from the R273H mutation/wild-type heteroduplexed template. Each sample has three lanes. The first lane is a control where no EndoV is added. The second and third lanes are cleavage products with EndoV. In the second lane, no EDTA is added to terminate the EndoV reaction. In the third lane, 10 mM EDTA (final concentration) was added at the end of the EndoV reaction to terminate the reaction. WT: wild-type, Mut: heteroduplex containing 50% of p53 exon 8 mutation R273H and 50% wild-type PCR fragments.

FIGS. 20A-B are a display of capillary electrophoretic results of EndoV cleavage products of p53 exon 6 (Q192Ter, Y205F) fragments generated by PCR. The experiment compares protection of label from EndoV cleavage with internally labeled universal primers (FIG. 20A) and reversed linkage labeled universal primers (FIG. 20B). Fragments were PCR amplified, denatured, and renatured as illustrated in FIG. 4. W: wild type homoduplex PCR products. M: heteroduplexes of 50% mutants PCR products and 50% wild type PCR products. Mutation in sample 1: p53 exon 6 Q192Ter. Mutations in sample 2: p53 exon 6 Y205F. Since this experiment was designed to determine if mutation cleavage products could be distinguished even in a high background, the ligation step was omitted. In FIG. 20A, the label is resistant to EndoV cleavage, but higher molecular weight artifacts are observed migrating at about 600 bases. In FIG. 20B, the artifacts are not observed, but substantial label is cleaved off as indicated by the lower molecular weight fragments.

Figure 21:
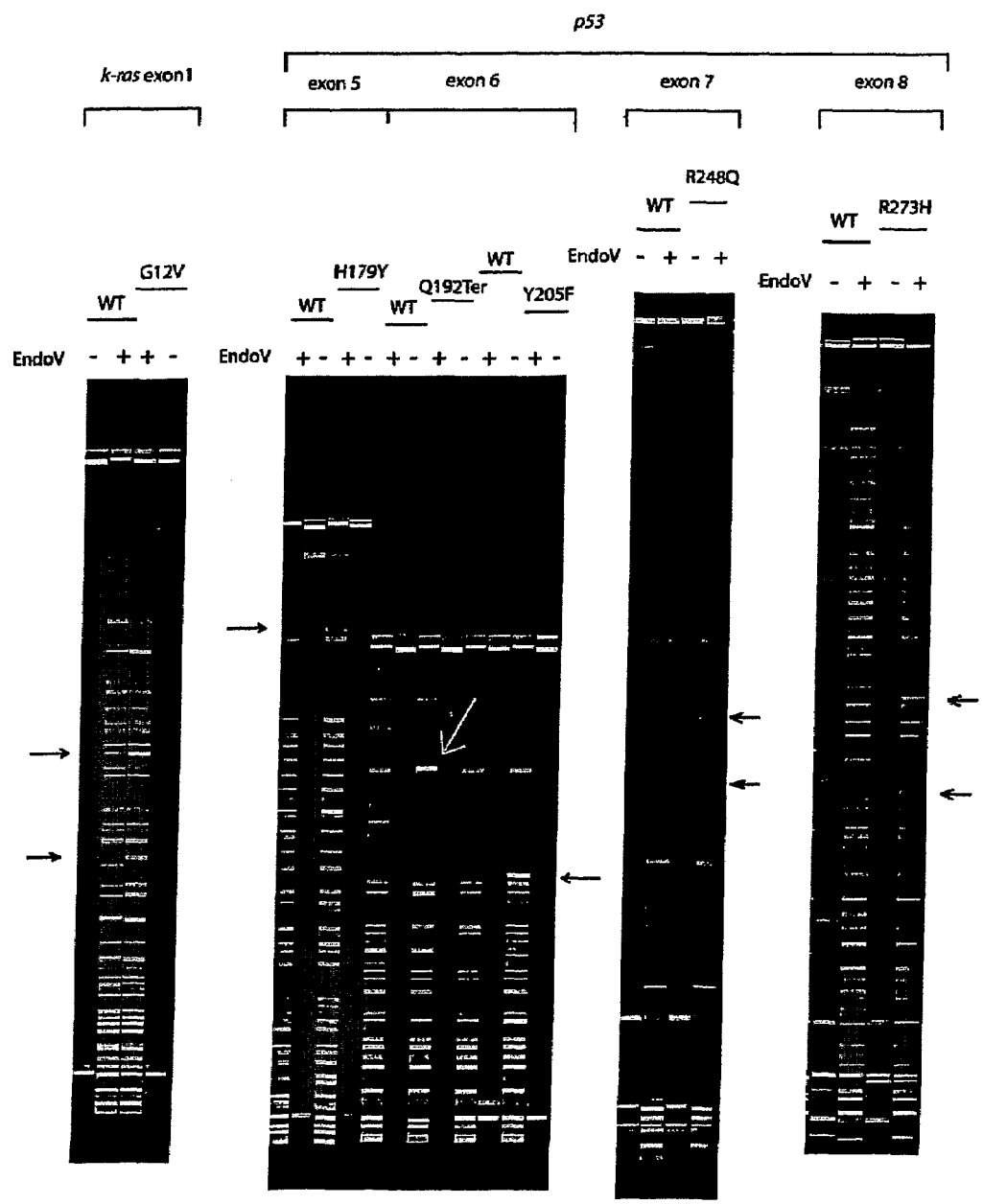

FIG. 21 is an electrophoretogram of EndoV cleavage products for detecting mutations in k-ras exon 1 and p53 genes exon 5, 6, 7, and 8 when internally labeled PCR primers were used. Fragments were PCR amplified, denatured, and renatured, as illustrated in FIG. 3. WT: wild type. PCR products from wild-type DNA and mutant DNA from clinical samples were amplified with internally labeled primers. EndoV cleavage reactions were carried out on DNA duplexes in a standard reaction condition. Since this experiment was designed to determine if mutation cleavage products could be distinguished even in a high background, the ligation step was omitted. Reactions of negative controls (without EndoV) were also carried out. Cleavage products were electrophoresed in a ABI 3730 sequencer. The results were analyzed with GeneMapper and visualized with Gel Render. The cleavage products of mutations G12V in k-ras exon1, H179Y in p53 exon 5, Q192Ter and Y205F in p53 exon 6, R248Q in p53 exon 7, and R273H in p53 exon 8 can be identified by comparison of cleavage products from wild-type DNA with cleavage products from mutant DNA. The cleavage products of mutations are indicated with arrows.

Figure 22:
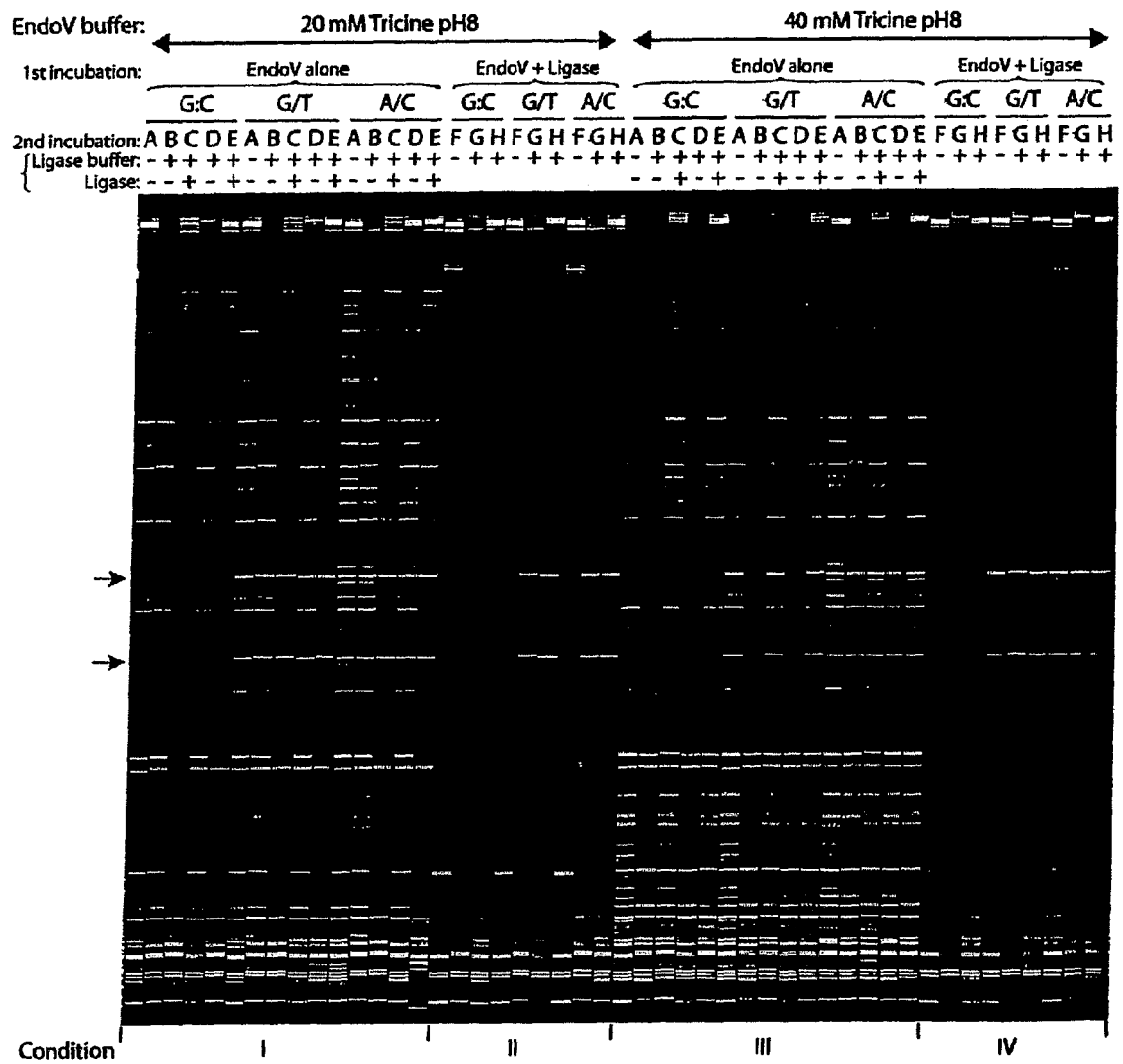

FIG. 22 is an electrophoretogram of EndoV/Ligase cleavage products of heteroduplexed DNA containing the p53 exon 8 R273H mutation obtained under various buffer conditions. Wild-type and mutant fragments were PCR amplified using either VicUniEV1F with p-UniEV2R or NedUniEV2R with p-UniEV1F, in conjunction with gene-specific primers to generate fragments with one labeled and one unlabeled strand. Mixtures were heteroduplexed using "split label, denaturation/renaturation" such that only the G/T or A/C heteroduplex was labeled as illustrated in FIG. 5. Buffer conditions I through IV, as well as standard conditions are listed below and in Table 6.

| Standard conditions: | [40 min] | 1- 1x EndoV buffer = 20 mM Hepes pH 7.5, 5 mM MgCl$_2$, 1 mM DTT, 5% DMSO, 1.5 M betaine, 2% glycerol, with 1 μM EndoV |
| --- | --- | --- |
| | [30 min] | 2- 1x Ligase buffer = 20 mM Tris pH 8.5, 1.25 mM MgCl$_2$, 50 mM KCl, 10 mM DTT, 20 μg/ml BSA, with 3 nM Ligase + 1 mM NAD |
| Condition I-E: | [60 min] | 1- 1x EndoV buffer = 20 mM Tricine pH 8, 5 mM MgCl$_2$, 1 mM DTT, 5% DMSO, 1.5 M betaine, 2% glycerol, with 1 μM EndoV |
| | [60 min] | 2- 1x Ligase buffer = 40 mM Tricine pH 8, 1.25 mM MgCl$_2$, 10 mM DTT, 20 μg/ml BSA, with 6 nM Ligase + 5 mM NAD |
| Condition II-H: | [60 min] | 1- 1x EndoV buffer = 20 mM Tricine pH 8, 5 mM MgCl$_2$, 1 mM DTT, 5% DMSO, 1.5 M betaine, 2% glycerol, with 1 μM EndoV + 6 nM Ligase + 5 mM NAD |
| | [60 min] | 2- 1x Ligase buffer = 40 mM Tricine pH 8, 1.25 mM MgCl$_2$, 6.25 mM DTT, 20 μg/ml BSA |
| Condition III-E: | [60 min] | 1- 1x EndoV buffer = 40 mM Tricine pH 8, 5 mM MgCl$_2$, 1 mM DTT, 5% DMSO, 1.5 M betaine, 2% glycerol, with 1 μM EndoV |
| | [60 min] | 2- 1x Ligase buffer = 40 mM Tricine pH 8, 1.25 mM MgCl$_2$, 10 mM DTT, 20 μg/ml BSA, with 6 nM Ligase + 5 mM NAD |
| Condition IV-H: | [60 min] | 1- 1x EndoV buffer = 40 mM Tricine pH 8, 5 mM MgCl$_2$, 5 mM DTT, 5% DMSO, 1.5 M betaine, 2% glycerol, with 1 μM EndoV + 6 nM Ligase + 5 mM NAD |
| | [60 min] | 2- 1x Ligase buffer = 40 mM Tricine pH 8, 1.25 mM MgCl$_2$, 6.25 mM DTT, 20 μg/ml BSA |

In these experiments, two distinct types of wild-type/mutant PCR mixtures were "split label, denatured/renatured", and then subjected to the EndoV reaction: heteroduplexes of top strand wild-type with bottom strand mutant (G/T mismatch) and heteroduplexes of top strand mutant with bottom strand wild-type (A/C mismatch). Wild-type PCR mixtures were used as controls (G:C match). EndoV/Ligase reactions were carried out either as "classical" two-step procedures (conditions I and III: $1^{st}$ incubation with EndoV, $2^{nd}$ incubation with Ligase), or as two-step procedures that combined both enzymes in the first incubation step (conditions II and IV: $1^{st}$ incubation with [EndoV+Ligase], $2^{nd}$ incubation with Ligase buffer). Within conditions I and III, a few sub-conditions were tested:

A: $1^{st}$ incubation with EndoV for 60 min, no $2^{nd}$ incubation

B: $1^{st}$ incubation with EndoV for 60 min, $2^{nd}$ incubation with Ligase buffer only for 30 min C: $1^{st}$ incubation with EndoV for 60 min, $2^{nd}$ incubation with Ligase buffer+Ligase for 30 min D: $1^{st}$ incubation with EndoV for 60 min, 2nd incubation with Ligase buffer only for 60 min E: $1^{st}$ incubation with EndoV for 60 min, 2nd incubation with Ligase buffer+Ligase for 60 min Likewise, a few sub-conditions were tested within conditions II and IV:

F: $1^{st}$ incubation with EndoV+Ligase for 60 min, no $2^{nd}$ incubation

G: $1^{st}$ incubation with EndoV+Ligase for 60 min, $2^{nd}$ incubation with Ligase buffer for 30 min H: $1^{st}$ incubation with EndoV+Ligase for 60 min, $2^{nd}$ incubation with Ligase buffer for 60 min Reaction mixtures were electrophoresed on the ABI 3730 fluorescence-based capillary electrophoresis instrument (Applied Biosystems, Foster City, Calif.). At completion of the electrophoretic run, a virtual gel image was displayed on the instrument monitor, with Vic- and Ned-labeled fragments appearing in green and yellow, respectively. Data analysis was achieved using Gene Mapper fragment analysis software.

Figure 23:
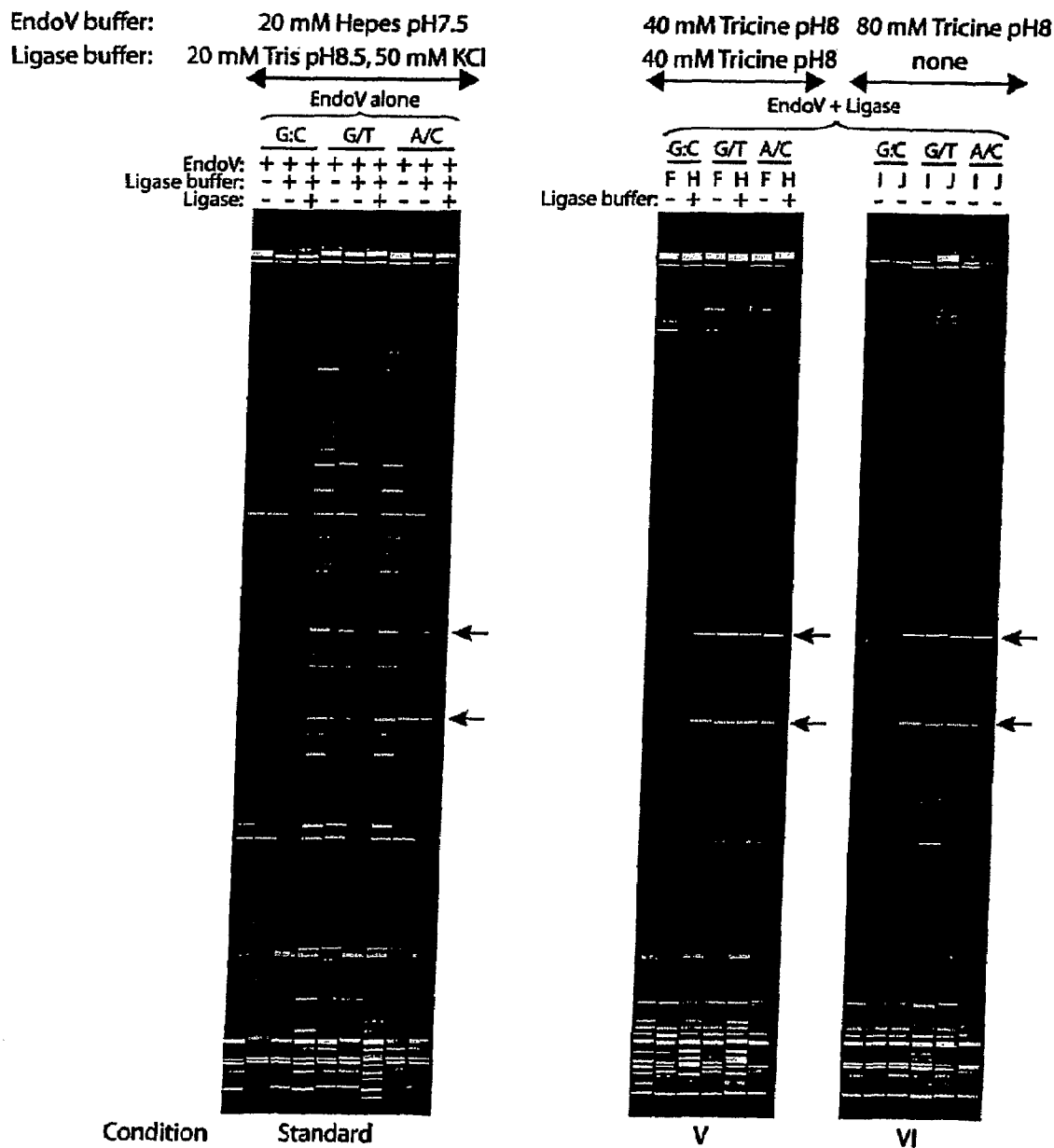

FIG. 23 is an electrophoretogram of EndoV/Ligase cleavage products of heteroduplexed DNA containing the p53 exon 8 R273H mutation, showing a comparison of one-step versus two-step incubation conditions. Wild-type and mutant fragments were PCR amplified using either VicUniEV1F with p-UniEV2R or NedUniEV2R with p-UniEV1F, in conjunction with gene-specific primers to generate fragments with one labeled and one unlabeled strand. Mixtures were heteroduplexed using "split label, denaturation/renaturation" such that only the G/T or A/C heteroduplex were labeled as illustrated in FIG. 5. Buffer conditions V and VI, as well as the standard conditions are listed below and in Table 7.

In these experiments, two distinct types of wild-type/mutant PCR mixtures were "split label, denatured/renatured", and then subjected to the EndoV reaction: heteroduplexes of top strand wild-type with bottom strand mutant (G/T mismatch) and heteroduplexes of top strand mutant with bottom strand wild-type (A/C mismatch). Wild-type PCR mixtures were used as controls (G:C match). EndoV/Ligase reactions were carried out either as a two-step procedure combining both enzymes in the first incubation step (condition V: $1^{st}$ incubation with [EndoV+Ligase], $2^{nd}$ incubation with Ligase buffer), or as a single-step procedure (condition VI: one incubation with [EndoV+Ligase]). In addition, a standard two-step procedure was performed (standard conditions: $1^{st}$ incubation with EndoV, $2^{nd}$ incubation with Ligase). Within condition V, a few sub-conditions were tested:

F: $1^{st}$ incubation with EndoV+Ligase for 60 min, no $2^{nd}$ incubation

H: $1^{st}$ incubation with EndoV+Ligase for 60 min, $2^{nd}$ incubation with Ligase buffer for 60 min Likewise, a few sub-conditions were tested within condition VI:

I: $1^{st}$ incubation with EndoV+Ligase for 60 min, no $2^{nd}$ incubation

J: $1^{st}$ incubation with EndoV+Ligase for 120 min, no $2^{nd}$ incubation

Reaction mixtures were electrophoresed on the ABI 3730 fluorescence-based capillary electrophoresis instrument (Applied Biosystems, Foster City, Calif.). At completion of the electrophoretic run, a virtual gel image was displayed on the instrument monitor, with Vic- and Ned-labeled fragments appearing in green and yellow, respectively. Data analysis was achieved using Gene Mapper fragment analysis software.

Figure 24:
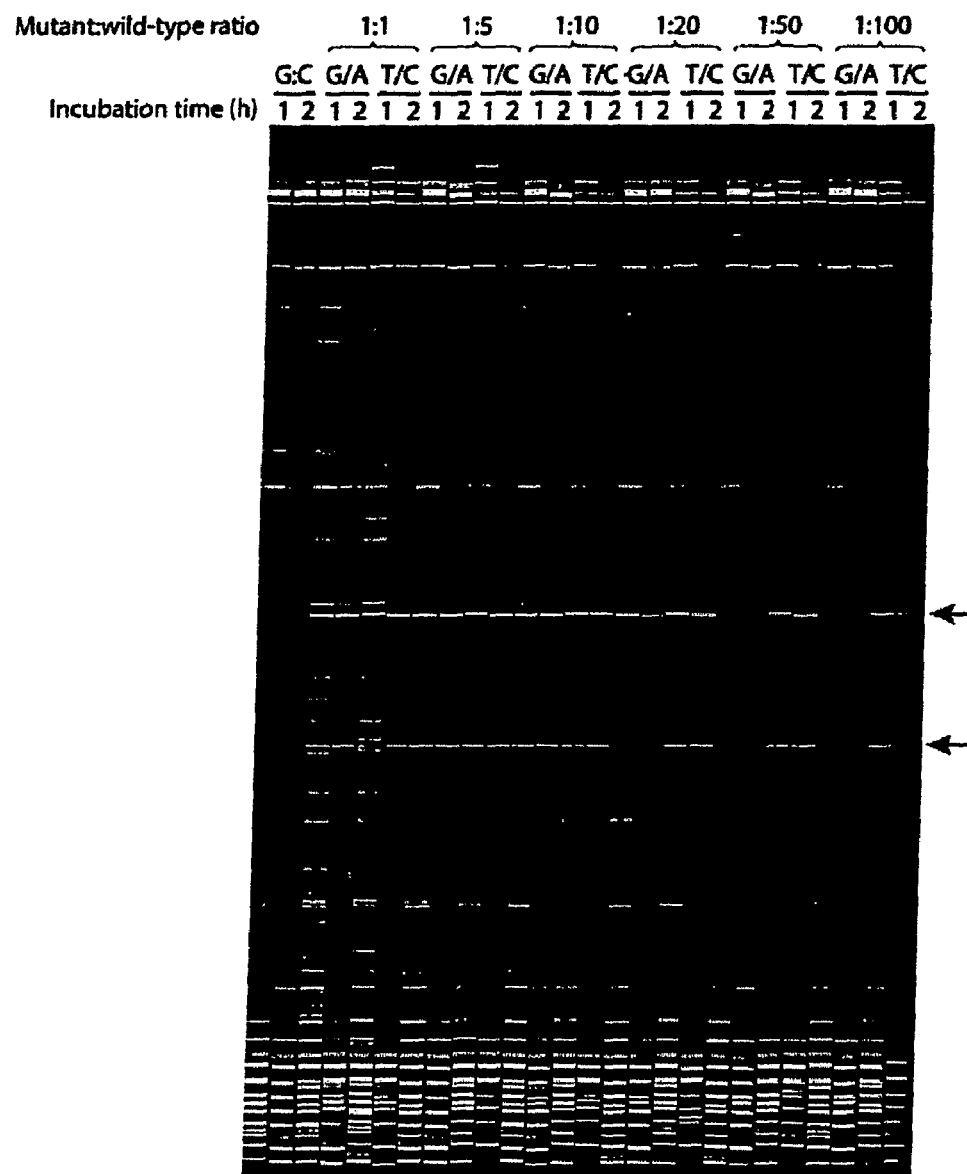

FIG. 24 shows the sensitivity of the EndoV/Ligase mutation scanning assay on K-ras exon 1 G12V. Wild-type and mutant fragments were PCR amplified using either VicUniEV1F with p-UniEV2R or NedUniEV2R with p-UniEV1F, in conjunction with gene-specific primers to generate fragments with one labeled and one unlabeled strand. Mixtures were heteroduplexed using "split label, denaturation/renaturation" such that only the G/T or A/C heteroduplex was labeled as illustrated in FIG. 5. The EndoV/Ligase incubations were performed under the following single-step conditions/one- or two-hour incubation at 65° C. in 80 mM Tricine pH 8, 5 mM $MgCl_2$, 5 mM DTT, 2% glycerol, 5% DMSO, 1.5 M betaine, 1 mM NAD, using 1 μM EndoV and 12 nM Ligase. PCR fragments containing the G12V mutation were mixed with wild-type PCR fragments in the ratio of mutant-to-wild type of 1:1, 1:5, 1:10, 1:20, 1:50, and 1:100. This was applied to both types of wild-type/mutant heteroduplexes: heteroduplexes of top strand wild-type with

| | | |
|---|---|---|
| Standard conditions: | [40 min] | 1- 1x EndoV buffer = 20 mM Hepes pH 7.5, 5 mM $MgCl_2$, 1 mM DTT, 5% DMSO, 1.5 M betaine, 2% glycerol, with 1 μM EndoV |
| | [30 min] | 2- 1x Ligase buffer = 20 mM Tris pH 8.5, 1.25 mM $MgCl_2$, 50 mM KCl, 10 mM DTT, 20 μg/ml BSA, with 3 nM Ligase + 1 mM NAD |
| Condition V-H: | [60 min] | 1- 1x EndoV buffer = 40 mM Tricine pH 8, 5 mM $MgCl_2$, 5 mM DTT, 5% DMSO, 1.5 M betaine, 2% glycerol, with 500 nM EndoV + 6 nM Ligase + 5 mM NAD |
| | [60 min] | 2- 1x Ligase buffer = 40 mM Tricine pH 8, 1.25 mM $MgCl_2$, 6.25 mM DTT, 20 μg/ml BSA |
| Condition VI-J: | [120 min] | 1x EndoV/Ligase buffer = 80 mM Tricine pH 8, 5 mM $MgCl_2$, 5 mM DTT, 5% DMSO, 1.5 M betaine, 2% glycerol, with 500 nM EndoV + 6 nM Ligase + 5 mM NAD | bottom strand mutant (G/A mismatch) and heteroduplexes of top strand mutant with bottom strand wild-type (T/C mismatch). Wild-type PCR mixtures were used as controls (G:C match). Reaction mixtures were electrophoresed on the ABI 3730 fluorescence-based capillary electrophoresis instrument (Applied Biosystems, Foster City, Calif.). At completion of the electrophoretic run, a virtual gel image was displayed on the instrument monitor, with Vic- and Ned-labeled fragments appearing in green and yellow, respectively. Data analysis was achieved using Gene Mapper fragment analysis software.

FIGS. 25A-B represent two plots of relative intensity of fluorescence as a function of ratio of mutant-to-wild type, demonstrating the sensitivity of the EndoV/Ligase mutation scanning assay performed on K-ras exon 1 G12V mutation (G->T nucleotide change) under the following single-step conditions: two-hour incubation at 65° C. in 80 mM Tricine pH 8, 5 mM $MgCl_2$, 5 mM DTT, 2% glycerol, 5% DMSO, 1.5 M betaine, 1 mM NAD, using 1 µM EndoV and 12 nM Ligase. Bars indicate the relative fluorescence intensity with their respective mutant-to-wild type ratios: blue bars for the top strand cleavage products, pink bars for the bottom strand cleavage products. FIG. 25A displays the G/A mismatch data, while FIG. 25B shows the T/C mismatch data. The relative intensity of fluorescence is defined as the area under a signal's peak as determined by Gene Mapper fragment analysis software (data analyzed from FIG. 24).

Figure 26:
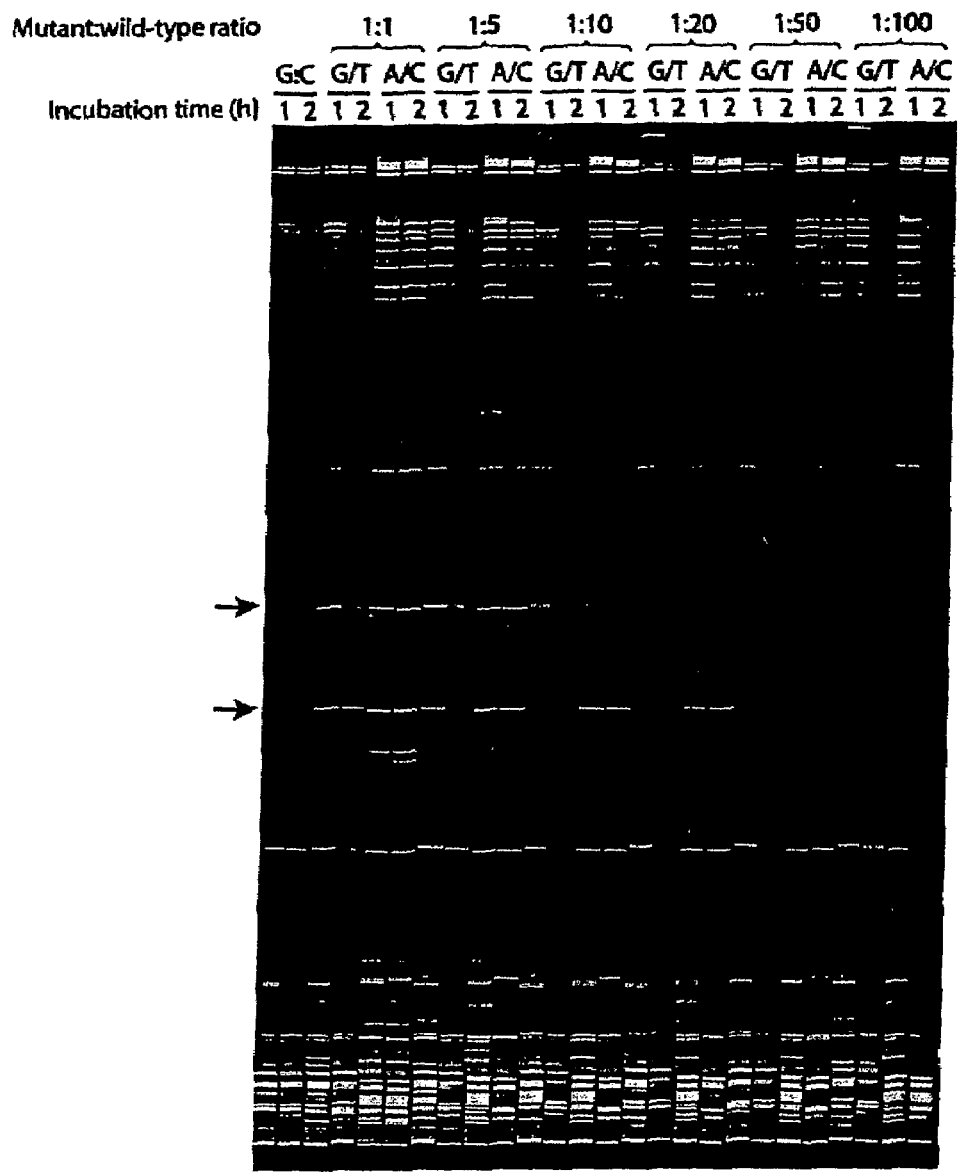

FIG. 26 shows the sensitivity of the EndoV/Ligase mutation scanning assay on p53 exon 8 R273H mutation. Wild-type and mutant fragments were PCR amplified using either VicUniEV1F with p-UniEV2R or NedUniEV2R with p-UniEV1F, in conjunction with gene-specific primers to generate fragments with one labeled and one unlabeled strand. Mixtures were heteroduplexed using "split label, denaturation/renaturation" such that only the G/T or A/C heteroduplex was labeled as illustrated in FIG. 5. The EndoV/Ligase incubations were performed under the following single-step conditions: one- or two-hour incubation at 65° C. in 80 mM Tricine pH 8, 5 mM $MgCl_2$, 5 mM DTT, 2% glycerol, 5% DMSO, 1.5 M betaine, 1 mM NAD, using 1 µM EndoV and 12 nM Ligase. PCR fragments containing the G12V mutation were mixed with wild-type PCR fragments in the ratio of mutant-to-wild type of 1:1, 1:5, 1:10, 1:20, 1:50, and 1:100. This was applied to both types of wild-type/mutant heteroduplexes: heteroduplexes of top strand wild-type with bottom strand mutant (G/T mismatch) and heteroduplexes of top strand mutant with bottom strand wild-type (A/C mismatch). Wild-type PCR mixtures were used as controls (G:C match). Reaction mixtures were electrophoresed on the ABI 3730 fluorescence-based capillary electrophoresis instrument (Applied Biosystems, Foster City, Calif.). At completion of the electrophoretic run, a virtual gel image was displayed on the instrument monitor, with Vic- and Ned-labeled fragments appearing in green and yellow, respectively. Data analysis was achieved using Gene Mapper fragment analysis software.

FIGS. 27A-B represents two plots of relative intensity of fluorescence as a function of ratio of mutant-to-wild type, demonstrating the sensitivity of the EndoV/Ligase mutation scanning assay performed on p53 exon 8 R273H mutation (G->A nucleotide change) under the following single-step conditions: two-hour incubation at 65° C. in 80 mM Tricine pH 8, 5 mM $MgCl_2$, 5 mM DTT, 2% glycerol, 5% DMSO, 1.5 M betaine, 1 mM NAD, using 1 µM EndoV and 12 nM Ligase. Bars indicate the relative fluorescence intensity with their respective mutant-to-wild type ratios: blue bars for the top strand cleavage products, pink bars for the bottom strand cleavage products. FIG. 27A displays the G/T mismatch data, while FIG. 27B shows the A/C mismatch data. The relative intensity of fluorescence is defined as the area under a signal's peak as determined by Gene Mapper fragment analysis software (data analyzed from FIG. 26).

DETAILED DESCRIPTION OF THE INVENTION

Detecting DNA Sequence Differences

One aspect of the present invention relates to a method for identifying one or more mutant nucleotide target sequences differing by one or more single-base changes, insertions, or deletions, from a normal nucleotide target sequences. This method involves providing one or more sample(s) potentially containing the normal nucleotide target sequence, one or more mutant nucleotide target sequences, or both. Also provided is a group of one or more primary oligonucleotide primer sets, each set characterized by (a) a first oligonucleotide primer, having a target-specific portion, and (b) a second oligonucleotide primer, having a target-specific portion, where only one of the primary oligonucleotide primers is provided with a label. A polymerase is provided, and the sample, the primary oligonucleotide primer sets, and the polymerase are blended to form one or more primary polymerase chain reaction mixture(s). The primary polymerase chain reaction mixture is subjected to one or more polymerase chain reaction cycles to form primary extension products complementary to the normal nucleotide target sequence and the mutant nucleotide target sequences are present in the sample. The polymerase is inactivated, and the primary polymerase chain reaction mixture(s) is subjected to a process which converts the primary extension products to a single-stranded form and anneals the single-stranded primary extension products to form heteroduplexed products potentially comprising nucleic acid molecules which include nucleotide sequences from the normal nucleotide target sequence and the mutant nucleotide target sequences. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves the heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. Products resulting from subjecting the ligase resealing reaction mixture to a ligase resealing reaction are separated by size or electrophoretic mobility. The presence of the normal nucleotide target sequences and the one or more mutant nucleotide sequences are detected in the sample by distinguishing the separated products resulting from the ligase resealing reaction.

The first step of the invention is the preparation of heteroduplex nucleic acid fragments. In the preferred embodiment, genomic DNA containing both wild-type and the sequence variation(s) (e.g. single nucleotide mutations or polymorphisms, one or more nucleotide insertions, and one or more nucleotide deletions) is PCR amplified with labeled oligonucleotide primers. Fluorescent, infrared, radioactive, or other labels may be used in the primers. In the preferred embodiment, Taq DNA polymerase or other PCR enzymes are inactivated, for example, by digestion with proteinase K. The mixture of mutation or polymorphism containing and wild-type PCR fragments are denatured and then reannealed to form heteroduplex PCR fragments with nucleotide mismatches. In the preferred embodiment, denaturation is achieved by heating the fragments above their Tm value (generally greater than 94° C.), and reannealing is achieved by cooling first to 50-85° C., more preferably, 65° C. for 5-30 minutes, more preferably 15 minutes, and then to room temperature for 5-30 minutes, more preferably 15 minutes, to form heteroduplex PCR fragments. Alternative means of denaturing/renaturing may be used. If wild-type genomic DNA is not known to be present in the original reaction, then concurrently in a separate reaction, wild type genomic DNA is PCR amplified using the exact same primers as above. Equal molar amounts of mutation containing PCR fragments and wild type PCR fragments are mixed, heated, and then cooled to form heteroduplex PCR fragments with nucleotide mismatches. Alternatively, denaturation can be achieved by digestion with an exonuclease.

The second step utilizes Tma endonuclease V for cleavage of the heteroduplex DNA containing base mismatches. This reaction is preferably performed in an optimized reaction buffer at high temperature (50-65° C.) for 30 minutes to 1 hour. Optimal buffer conditions include a neutral pH, low or no salt, and the presence of $Mg^{2+}$. Addition of organic solvents or other compounds, such as DMSO and betaine, may be used to facilitate cleavage by Tma EndoV. Use of alternative conditions or metal co-factors (such as $Mn^{2+}$) may also facilitate cleavage. Tma endonuclease V activity can be sufficient even under sub-optimal conditions. The cleavage site was determined to be one nucleotide beyond the 3' position of the nucleotide mismatch.

For the next step, a supplemental buffer is added to bring the contents and concentration of the buffer to a level optimized for a thermostable DNA ligase. In the preferred embodiment, a *Thermus* species ("Tsp.") AK16D DNA ligase is used. This ligation reaction is performed at 45 to 85° C., preferably 65° C., for 2 to 60 minutes, preferably 20 minutes and utilizes the high specificity of Tsp. AK16D DNA ligase to reseal complementary nicks, while leaving cleaved mismatches unaltered. This greatly reduces background and, therefore, dramatically increases the sensitivity of the assay.

In the fourth step, the cleaved fragments are separated, for example, by electrophoresis on a denaturing polyacrylamide gel or by capillary electrophoresis. Since the PCR primers of step one are labeled, fragments can be detected with the corresponding detection equipment. In the preferred embodiment, primers are fluorescently labeled and detected using automated DNA sequencing or fluorescent fragment analysis instrumentation. The lengths of products are determined by comparison of the mobility of cleavage products to a fluorescent labeled molecular size standard. This allows for an approximate determination of the position of a mutation.

FIG. 2 is a schematic diagram, illustrating an improved procedure for EndoV/Ligase mutation scanning assay, in accordance with one aspect of the present invention, using lambda exonuclease. One labeled (F1, left primer) and one 5' phosphorylated PCR primer (p, right primer) are used to PCR amplify the mutant gene (G:C) to form a first PCR product. A second PCR reaction is performed on target with the normal gene (A:T, p, left primer with F2 right primer) to form a second PCR product. A third and fourth set of PCR products may also be generated, using an F1-labeled left primer with a phosphorylated right primer for the normal gene and a phosphorylated left primer with an F2-labeled right primer for the mutant gene respectively. The first two PCR products are combined, and the phosphorylated strands digested with lambda exonuclease, generating two complementary labeled strands that anneal to form a G/T heteroduplex. (The same procedure is used on the third and fourth PCR products to form the opposite strand A/C heteroduplex). An endonuclease (EndoV) is used to preferentially nick DNA one base to the 3' side of mismatches, while a ligase is used to reseal background nicks at perfect match regions. The EndoV and ligase reactions may be performed in a single step. The products are separated via capillary electrophoresis and the length of the product is used to determine the site of the mutation. Use of pure labeled heteroduplexed DNA as generated with lambda exonuclease improves both signal as well as the signal-to-noise ratio (lanes 4 & 6).

FIG. 3 is a schematic diagram, illustrating an improved procedure for EndoV/Ligase mutation scanning assay using labeled primers that are resistant to EndoV cleavage. Labeled PCR primers are used to PCR amplify both the mutant and normal genes (in either the same or different reactions). Alternatively, one labeled and one unlabeled primer may be used to generate PCR products. The PCR products are combined, denatured, and reannealed, to form both G/T and A/C heteroduplexed DNA (as well as G:C and A:T homoduplexed DNA). Alternatively, the lambda exonuclease procedure illustrated in FIG. 2 may be used to generate heteroduplexed DNA. An endonuclease (EndoV) is used to preferentially nick DNA one base to the 3' side of mismatches, while a ligase is used to reseal background nicks at perfect match regions. The EndoV and Ligase reactions may be performed in a single step. The products are separated via capillary electrophoresis, and the length of the product is used to determine the site of the mutation. With standard 5' fluorescently labeled oligonucleotides, optionally having 2'-o-methyl-modified sugars in the linkage and/or containing a 5' CCGCC sequence, EndoV cleaves the label off the PCR fragment. This cleaved label runs anomalously on the capillary gel, with an apparent size of about 94 (for Ned) and 102 (for Vic) bases (lanes 2-5). Attachment of the fluorescent label internally in the primer sequence (via linkage to the C-6 position of cytosine, 4 or 5 bases from the 5' end) renders the primer resistant to cleavage by EndoV. However, an artifactual band migrating with apparent size of 600 bases appears (lanes 6-7). Attachment of the fluorescent label to the primer sequence via a reversed linkage (i.e. 3'-Fluorescent group-5'-5' primer sequence-3') renders the primer more resistant to cleavage by EndoV (lanes 8-9).

In carrying out the process of the present invention, the sample can contain a target nucleotide sequence which is either genomic DNA, DNA isolated from tumor samples, a double stranded cDNA copy of mRNA, or a PCR amplified DNA fragment. In the sample being analyzed according to the process of the present invention, the molar ratio of the mutant nucleotide target sequence to the normal nucleotide target sequence is in a range of 1:100 to 100:1.

The sample may comprise a mixture of germline DNA from multiple samples, a mixture of tumor DNA from multiple samples, or a mixture of target regions.

The process of the present invention is capable of distinguishing an inherited or sporadic mutation or polymorphism from a polymorphism in the normal target sequence. This distinction can be made in a tumor suppressor gene, oncogene, or DNA replication or repair gene. Such genes include Bcl2, Mdm2, Cdc25A, Cyclin D1, Cyclin E1, Cdk4, survivin, HSP27, HSP70, p53, $p21^{Cip}$, $p16^{Ink}4a$, $p19^{ARF}$, $p15^{INK4b}$, $p27^{Kip}$, Bax, growth factors, EGFR, Her2-neu, ErbB-3, ErbB-4, c-Met, c-Sea, Ron, c-Ret, NGFR, TrkB, TrkC, IGF1R, CSF1R, CSF2, c-Kit, AXL, Flt-1 (VEGFR-1), Flk-1 (VEGFR-2), PDGFRα, PDGFRβ, FGFR-1, FGFR-2, FGFR-3, FGFR-4, other protein tyrosine kinase receptors, β-catenin, Wnt(s), Akt, Tcf4, c-Myc, n-Myc, Wisp-1, Wisp-3, K-ras, H-ras, N-ras, c-Jun, c-Fos, PI3K, c-Src, Shc, Raf1, TGFβ, and MEK, E-Cadherin, APC, TβRII, Smad2, Smad4, Smad 7, PTEN, VHL, BRCA1, BRCA2, ATM, hMSH2, hMLH1, hPMS1, hPMS2, or hMSH3.

Since residual active Taq DNA polymerase can extend EndoV cleaved DNA, PCR reactions can be incubated with proteinase K at 45 to 75° C. for 5 to 60 min., preferably 70° C. for 10 min. Subsequently, proteinase K is inactivated at 80° C. to 95° C. for 10 to 30 minutes, preferably 85° C. for 10 minutes. After amplification and proteinase K digestion, PCR fragments can be separated by agarose gel electrophoresis and visualized via ethidium bromide staining.

Most biological sources of target DNA (e.g., a tumor sample) will contain both variant (mutation or polymorphism) and wild type DNA. In these cases, it is not necessary to add wild-type PCR fragments exogenously to the heteroduplex hybridization step. For example, if the substrate is genomic DNA containing a heterozygous germline mutation, only 50% of the PCR fragments will contain a mutation, while the other half will be of wild-type sequence. Therefore, it is not necessary to add wild-type PCR fragments. Likewise, for solid tumor samples, there is typically a significant amount of stromal (i.e. wild-type) DNA within these samples. For sources of substrate in which a significant amount of endogenous wild-type DNA does not exist, an approximately equal amount of wild-type PCR fragments needs to be added. The optimal final ratio of mutant-to-wild type PCR fragments should be 1:1, although the technique is compatible with other ratios of mutant-to-wild type PCR fragments.

The labeled oligonucleotide primers are labeled, preferably at their 5' ends. Useful labels include chromophores, fluorescent dyes, enzymes, antigens, heavy metals, magnetic probes, infrared dyes, phosphorescent groups, radioactive groups, chemiluminescent moieties, quantum dyes, quantum dots, and electrochemical detecting moieties.

In carrying out the method of the present invention, the first primary oligonucleotide primer and/or the second primary oligonucleotide primer are labeled at their 5' ends. Desirably, the label is resistant to endonuclease cleavage and is either attached to the first primary oligonucleotide primer and/or the second primary oligonucleotide primer via a 3'→5' linkage, and/or are labeled internally to their 5' ends.

The polymerase is either a native or recombinant thermostable polymerase from *Thermus aquaticus, Thermus thermophilus, Pyrococcus furiosus,* or *Thermotoga maritima*.

The polymerase chain reaction process is fully described in H. Erlich, et. al., "Recent Advances in the Polymerase Chain Reaction," *Science* 252: 1643-50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487-91 (1988), which are hereby incorporated by reference in their entirety. The polymerase chain reaction is initiated by adding either the polymerase or metal co-factors at temperatures of 65-94° C. to the polymerase chain reaction mixture. The step of denaturing the polymerase chain reaction extension products is carried out in the presence of proteinase K, preferably by heating to 80 to 105° C., preferably 94° C. The step of annealing the polymerase chain reaction extension products is carried out by cooling first to 50 to 85° C., preferably 65° C., for 5 to 30 minutes, preferably, 10 minutes and then to room temperature for 5 to 30 minutes, preferably, 15 minutes.

For heteroduplex DNA formation, the mixture containing fluorescently labeled mutant and wild-type PCR fragments is denatured by heating above 95° C. (i.e. at 95 to 100° C. for 15 sec. to 5 min., preferably, 95° C. for 1 min), thus rendering the DNA single-stranded. This is followed by a re-annealing step at 45 to 85° C. for 2 to 60 min., preferably 65° C. for 10 min, and, subsequently, incubating at room temperature for 5 to 30 min., preferably 15 min. After this process, theoretically 50% of the re-annealed products are heteroduplex DNA containing a base-mismatch. An alternative reanneal step would be a slow cool from 95 to 25° C., decreasing the temperature by less than 1° C. per minute, preferably, from 94° C. to 65° C. for 30-60 minutes. Alternative means of denaturing/renaturation of the DNA (such as treatment with a base followed by neutralization) may also be used. Typically, the polymerase chain reaction extension products have a length in the range of 50 bp to 1,700 bp.

Alternatively, the process which converts the primary extension products to a single-stranded form is carried out by digestion with an exonuclease. Preferably, the exonuclease is a 5'→3' exonuclease and, most preferably, lambda exonuclease.

The endonuclease is preferably an Endonuclease V from *Thermotoga maritima, Aquifex aeolicus, Pyrococcus furiosus, Pyrococcus horikoshii, Pyrococcus abyssi, Pyrobaculum aerophilum, Archaeoglobus fulgidus, Aeropyrum pernix, Clostridium acetobutylicum,* or *Bacillus subtilis*. The endonuclease desirably nicks or cleaves heteroduplexed products at a location on the 3' side one base away from mismatched base pairs. The endonuclease preferentially cleaves mismatches within the heteroduplexed products selected from the group consisting of A/A, G/G, T/T, A/G, A/C, G/A, G/T, T/G, T/C, C/A, and C/T. Alternatively, the endonuclease preferentially nicks or cleaves at least one of the heteroduplexed products formed for any single base mutation or polymorphism, except those having a sequence selected from the group consisting of gRcg, rcRc, cgYc, and gYgy, where the position of the mismatch is underlined and shown in upper case. The endonuclease preferentially nicks or cleaves one, two, and three base insertions or deletions within the heteroduplexed products.

The endonuclease is preferably a thermostable endonuclease which preferentially nicks or cleaves heteroduplexed DNA at a location where base pairs are mismatched or one base beyond the mismatch and generates ends which are suitable for ligation when nicking perfectly matched DNA.

The endonuclease cleavage reaction is preferably carried out in presence of $MgCl_2$ at a concentration of 2-7 mM or $MnCl_2$ at a concentration of 0.4-1.2 mM. $MgCl_2$ should be added where the endonuclease to heteroduplexed product weight ratio in the endonuclease cleavage reaction mixture is in the range of 10:1 to 100:1; substantially no NaCl or KCl is present. Where the endonuclease to heteroduplexed product weight ratio in the endonuclease cleavage reaction mixture is in the range of 1:1 to 1:10, $MnCl_2$ should be added; in this case, a 25 to 75 mM, preferably 50 mM, concentration of NaCl or KCl is present. Endonuclease cleavage can also be carried out in the presence of DMSO in a volume percent range of 2.5% to 10%, a mixture containing tetramethylene sulfone or tetrasulfoxide in a range of 2.5 to 10 volume %, and/or betaine in a concentration of 0.5M to 1.5M. Preferably, the endonuclease treatment is carried out at 50-65° C. for 1 hour.

In the next step of the present invention, heteroduplexed PCR fragments are cleaved by Tma endonuclease V. Tma endonuclease V contains unique properties that make it ideal for this process. Most significant is its ability to preferentially cleave one base beyond the 3' side of a mismatch and the fact that spurious nicks at complementary regions are suitable substrates for religation with DNA ligase. While there are other mismatch repair enzymes which are more efficient in recognizing base mismatches, they generally do not cleave at the mismatch, nor do they leave ends suitable for religation. In conjunction with an appropriate ligase, these properties of Tma Endo V allow for the reduction of background noise due to spurious nicking, while maintaining cleaved sites associated with mismatch sequence.

The next step of this invention seals nonspecific nicks in the heteroduplex PCR fragments with a thermostable ligase, such as *Thermus* species AK16D, *Thermus aquaticus, Thermus thermophilus, Pyrococcus furiosus*, or *Thermotoga maritima*. The thermostable ligase may be derived from *Thermus aquaticus*. M. Takahashi, et al., "Thermophillic DNA Ligase," *J. Biol. Chem.* 259:10041-47 (1984), which is hereby incorporated by reference in its entirety. Alternatively, it can be prepared recombinantly. Procedures for such isolation as well as the recombinant production of *Thermus aquaticus* ligase as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," *Gene* 109:1-11 (1991), which are hereby incorporated by reference. These references contain complete sequence information for this ligase as well as the encoding DNA. Ligase resealing is preferably carried out in the presence of 50 mM KCl to inhibit further endonucleolytic cleavage. Preferably, Tsp AK16D ligase is used. Ligase resealing is carried out at a pH value between 7.2 and 7.8 when measured at 25° C. Ideally, the cleavage of Tma endonuclease V should be inhibited in this step. The optimal reaction buffer for Tsp AK16D ligase is 20 mM Tris-HCl (pH 8.5), 5 mM $MgCl_2$, 25-75 mM (preferably, 50 mM) KCl, 10 mM dithiothreitol, 1 mM $NAD^+$, and 20 mg/ml BSA. See Tong, J., et al., *Nucleic Acid Research* 27:788-94 (1999), which is hereby incorporated by reference in its entirety. Tma. endo V is almost completely inhibited in the presence of 50 mM KCl.

In order to obtain near optimal buffer conditions for the Tsp AK16D ligase reaction, a supplemental buffer is added to the Tma Endo V reaction. In a preferred embodiment, the 10× supplemental buffer consists of 200 mM Tris-HCl (pH 8.5), 12.5 mM $MgCl_2$, 500 mM KCl, 100 mM DTT, and 200 g/ml BSA. Typically, 15 μL of the reaction mixture from a Tma Endonuclease V cleavage reaction, 2 μL of 10× supplemental buffer, 1 μL of 20 mM $NAD^+$, and 2 μL of 10-100 nM Tsp AK16D ligase (stock enzyme solution) are combined. The mixture can then be incubated at 65° C. for 20 min and terminated by adding an equal volume of GeneScan stop solution (50 mM EDTA, 1% blue dextran and 80% formamide).

The endonuclease cleavage and ligase resealing reactions can be carried out simultaneously. As a result, the ligase resealing reaction causes products arising from mismatch cleavage/resealing to accumulate more rapidly than products arising from match cleavage/resealing or causes the rate of mismatch cleavage minus the rate of mismatch ligation to be greater than the rate of match cleavage minus the rate of match ligation.

The next step of the present invention involves detection of the reaction products which can be carried out using polyacrylamide gel electrophoresis or capillary gel electrophoresis.

In the preferred embodiment, the reaction mixture is denatured at 94° C. for only 1 minute (to avoid DNA fragmentation which can increase background signal), and then cooled on ice. 2-3 μL of the mixture can then be loaded onto a 6% denaturing polyacrylamide gel and electrophoresed for 1 hour. An ABI 377 sequencer (Perkin Elmer) at 1000 volt, 60 mA current, 200 W power, and a gel temperature of 45° C. can be used to separate and detect DNA products, although alternative capillary or gel electrophoresis approaches can be used. Fluorescent groups, 6-Fam and Tet, resolve blue and green, respectively, in the ABI DNA 377 sequencer. The color of the cleavage band indicates whether the cleavage product originated from the top or bottom strand. TAMRA labeled GeneScan Molecular size standard 500 are loaded on the same gel. This allows for the molecular weight of cleavage products to be estimated by comparing the relative mobility of a cleavage product to the size standard. Preferably, the GeneScan analysis software versions 2.1 or 3.0a (PE-Biosystems) is used, although any state of the art gel-analysis software can instead be employed. This analysis allows for the approximate site of the mutation to be determined.

Another aspect of the present invention relates to a method for identifying one or more mutant nucleotide target sequences differing by one or more single-base changes, insertions, or deletions, from one or more normal nucleotide target sequences. This involves providing one or more sample(s) potentially containing the normal nucleotide target sequences, one or more mutant nucleotide target sequences, or both. Also provided is a group of one or more primary oligonucleotide primer sets. Each set comprises (a) a first primary oligonucleotide primer, having a target-specific portion and a 5' upstream secondary primer-specific portion, and (b) a second primary oligonucleotide primer, having a target-specific portion and a 5' upstream secondary primer-specific portion. The first primary oligonucleotide primers of each set in a group contain the same 5' upstream secondary primer-specific portion, and the second oligonucleotide primers of each set in a group contain the same 5' upstream secondary primer-specific portion. The sample, the one or more primary oligonucleotide primer sets, and a polymerase are blended to form one or more primary polymerase chain reaction mixture(s). The one or more primary polymerase chain reaction mixture(s) is subjected to one or more polymerase chain reaction cycles to form primary extension products complementary to the normal nucleotide target and mutant nucleotide target sequences present in the sample. A group of one or more secondary oligonucleotide primer sets, each set comprising (a) a first secondary oligonucleotide primer which comprises the same sequence as the 5' upstream secondary primer-specific portion of the first primary oligonucleotide primer, and (b) a second secondary oligonucleotide primer, which comprises the same sequence as the 5' upstream secondary primer-specific portion of the second primary oligonucleotide primer, is also provided. The one or more primary polymerase chain reaction mixture(s), the one or more secondary oligonucleotide primer sets, and a polymerase are blended to form one or more secondary polymerase chain reaction mixture(s). The one or more secondary polymerase chain reaction mixture(s) is subjected to one or more polymerase chain reaction cycles to form secondary extension products complementary to the primary extension products. The polymerase is then inactivated, and the one or more secondary polymerase chain reaction mixture(s) is subjected to a process which converts the secondary extension products to a single-stranded form and anneals the single-stranded secondary extension products to form heteroduplexed products potentially comprising nucleic acid molecules which include nucleotide sequences from the normal nucleotide target sequence and from the mutant nucleotide target sequence. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. After subjecting the ligase resealing reaction mixture to a ligase resealing reaction, products are separated by size or electrophoretic mobility or hybridization to capture probes attached to a solid support. The presence of the normal nucleotide target sequences and the one or more mutant nucleotide target sequences in the sample is detected by distinguishing the separated products.

FIG. 4 is a schematic diagram, illustrating a procedure for generating heteroduplexed DNA using universal primers and denaturation/renaturation. One or more fragments of target DNA are PCR amplified using a low concentration of gene-specific/universal primers and Taq DNA polymerase. In the same or a subsequent reaction, a high concentration of labeled universal primers are present, containing the same sequence and additional marker bases on their 3' end. In FIG. 4, the F1-labeled universal primer (Un1) contains a 3' AC sequence, while the F2-labeled universal primer contains a 3' CA sequence. The PCR reaction is continued at a lower temperature and the labeled fragments predominate. Since the two primers share the same universal sequence on their 5' ends, primer dimers do not amplify. In a separate (or the same) reaction, PCR is used to amplify normal DNA, as above. Denatured and renatured mutant and normal products are used to generate both G/T and A/C heteroduplexed fragments. This procedure allows one or more fragments to be amplified simultaneously for evaluation of fragments via capillary electrophoresis, or via an addressable array format. In the array format, there is no need to label the heteroduplexed fragments.

FIG. 5 is a schematic diagram, illustrating a procedure for generating heteroduplexed DNA using universal primers and split label, denaturation/renaturation. One or more fragments of target DNA are PCR amplified using a low concentration of gene-specific/universal primers and Taq DNA polymerase. In the same or a subsequent reaction, a high concentration of one labeled and one unlabeled universal primer are present, containing the same sequence and additional marker bases on their 3' end. In FIG. 5, the F1-labeled universal primer (Un1) contains a 3' AC sequence, while the unlabeled universal primer contains a 3' CA sequence. The PCR reaction is continued at a lower temperature and the labeled fragments predominate. Since the two primers share the same universal sequence on their 5' ends, primer dimers do not amplify. In a separate reaction, PCR amplifies normal DNA as above, but the universal primer which is labeled (F2 with a 3' CA sequence) and which is unlabeled (unlabeled universal primer contains a 3' AC sequence) are switched. Denaturation and renaturation of mutant and normal products generate both G/T and A/C heteroduplexed fragments for a total of 4 heteroduplexes. In this example, only the G/T heteroduplex is labeled. The primer sets are reversed to generate the labeled complementary A/C heteroduplex. This procedure allows one or more fragments to be amplified simultaneously for evaluation of fragments via capillary electrophoresis, or via an addressable array format.

FIG. 6 is a schematic diagram, illustrating a procedure for generating heteroduplexed DNA using lambda exonuclease and universal primers. One or more fragments of target DNA are PCR amplified using a low concentration of gene-specific/universal primers and Taq DNA polymerase. In the same or a subsequent reaction, a high concentration of one labeled and one phosphorylated universal primer are present, containing the same sequence and additional marker bases on their 3' end. In the illustration shown, the F1-labeled universal primer (Un1) contains a 3' AC sequence, while the phosphorylated universal primer contains a 3' CA sequence. The PCR reaction is continued at a lower temperature and the labeled fragments predominate. Since the two primers share the same universal sequence on their 5' ends, primer dimers do not amplify. In a separate reaction, PCR amplifies normal DNA as above, but the universal primer which is labeled (F2 with a 3' CA sequence) and which is phosphorylated (phosphorylated universal primer contains a 3' AC sequence) are switched. The two PCR products are mixed and treated with lambda exonuclease, allowing the newly generated single-stranded DNA to anneal and generate labeled G/T heteroduplexed fragments. The primer sets are reversed to generate the labeled complementary A/C heteroduplex. This procedure allows one or more fragments to be amplified simultaneously for evaluation of fragments via capillary electrophoresis, or via an addressable array format.

FIG. 7 is a schematic diagram, illustrating a procedure for generating heteroduplexed DNA using universal primers and ligated adapters. One or more fragments of target DNA are PCR amplified using a low concentration of gene-specific/universal primers and Taq polymerase. In the same or a subsequent reaction, a high concentration of phosphorylated universal primers are present, containing the same sequence and additional marker bases on their 3' end. In FIG. 7, the left phosphorylated universal primer (Un1) contains a 3' AC sequence, while the right phosphorylated universal primer contains a 3' CA sequence. The PCR reaction is continued at a lower temperature and the phosphorylated fragments predominate. Since the two primers share the same sequence, primer dimers do not amplify. In a separate reaction, normal DNA is PCR amplified as above, using universal primers containing additional bases on their 5' ends. As shown in FIG. 7, the left phosphorylated universal primer (Un1) contains a 5' GG sequence and a 3' AC sequence, while the right phosphorylated universal primer contains a 5' GGG sequence and a 3' CA sequence. The PCR products are denatured and renatured to generate heteroduplexed fragments with asymmetrical "sticky ends". Linkers with corresponding overhangs (i.e. 2 base 5'GG overhang on the left, and 3 base 5'GGG overhang on the right) are ligated with T4 ligase, only to the correct heteroduplexed ends. Companion linkers may be used that ligate to ends containing an additional 3' A which is often added to the ends of PCR products by Taq DNA polymerase. The linkers contain blocking groups to render the heteroduplexed DNA resistant to a subsequent exonuclease digestion. Reannealed homoduplexes do not have sticky end overhangs and are not protected by linker ligation. As shown in FIG. 7, the linkers protect the G/T heteroduplex (but not the G:C or A:T homoduplexes) from digestion with exonucleases. A separate reaction or the same reaction contains linkers for protection of the complementary A/C heteroduplex. This procedure allows one or more fragments to be amplified simultaneously for evaluation of fragments via an addressable array format.

In carrying out the method of the present invention, a first secondary polymerase chain reaction is carried out with a first secondary oligonucleotide primer which is labeled and one or more second secondary oligonucleotide primers which are unlabeled. The second secondary polymerase chain reaction is carried out with a second secondary oligonucleotide primer which labeled and one or more first secondary oligonucleotide primers which are unlabeled. The first secondary polymerase chain reaction produces secondary extension products that are labeled and complements of the secondary polymerase extension products, which are also labeled, of the second secondary polymerase chain reaction. After the first and second secondary polymerase chain reactions, their secondary polymerase chain reaction mixtures are blended to create the heteroduplex products. The secondary polymerase chain reaction mixture for the first secondary polymerase chain reaction potentially comprises nucleic acid molecules which include nucleotide sequences from the mutant nucleotide target sequence. The secondary polymerase chain reaction mixture for the second secondary polymerase chain reaction comprises nucleic acid molecules which include nucleotide sequences from the normal nucleotide target sequence. The secondary polymerase chain reaction mixture for the first secondary polymerase chain reaction potentially comprises nucleic acid molecules which include nucleotide sequences from a first mutant nucleotide target sequence in a first sample, while the secondary polymerase chain reaction mixture for the second secondary polymerase chain reaction comprises nucleic acid molecules which include nucleotide sequences from a different mutant nucleotide target sequences in a second sample.

The method of the present invention can alternatively involve carrying out the first and second secondary polymerase chain reactions with a first secondary oligonucleotide primer which is labeled and one or more second secondary oligonucleotide primers which are unlabeled. Third and fourth secondary polymerase chain reactions are carried out with one or more first secondary oligonucleotide primers which are unlabeled and a second secondary oligonucleotide primer which is labeled. The first and second secondary polymerase chain reactions produce secondary extension products that are labeled and complementary to the secondary polymerase extension products, which are also labeled, of the third and fourth polymerase chain reactions. After the first and fourth secondary polymerase chain reactions, their secondary polymerase chain reaction mixtures are blended to create a first heteroduplex product and, after the second and third polymerase chain reactions, their secondary polymerase chain reaction are blended to create a second heteroduplex product. The secondary polymerase chain reaction mixtures for the first and third polymerase chain reactions potentially comprises nucleic acid molecules which include nucleotide sequences from the mutant nucleotide target sequences, while the secondary polymerase chain reaction mixture for the second and fourth polymerase chain reactions comprise nucleic acid molecules which include nucleotide sequences from the normal nucleotide target sequences. The secondary polymerase chain reaction mixtures for the first and third polymerase chain reactions potentially comprise nucleic acid molecules which include nucleotide sequences from a first mutant nucleotide target sequence in a first sample. The secondary polymerase chain reaction mixtures for the second and fourth polymerase chain reactions potentially comprises nucleic acid molecules which include nucleotide sequences from different mutant nucleotide target sequences in a second sample.

The method of the present invention also involves using a plurality of secondary polymerase chain reaction mixtures which comprise a first secondary oligonucleotide primer which is labeled and one or more second secondary oligonucleotide primers which are unlabeled. A plurality of secondary polymerase chain reaction mixtures comprise a second secondary oligonucleotide primer which is labeled and one or more first secondary oligonucleotide primers which are unlabeled. The secondary polymerase chain reactions are carried out with the plurality of first secondary polymerase chain reaction mixtures to produce secondary extension products that are labeled and complements to the secondary extension products, which are also labeled, from the secondary polymerase chain reactions carried out with the plurality of second secondary polymerase chain reaction mixtures. After the secondary polymerase chain reactions are carried out with the plurality of first and second secondary polymerase chain reaction mixtures, the plurality of second secondary polymerase chain reaction mixtures are blended to create a plurality of first heteroduplex products. The plurality of second secondary polymerase chain reaction mixtures are blended with a plurality of first secondary polymerase chain reaction mixtures to create second heteroduplex products. The plurality of first secondary polymerase chain reaction mixtures potentially comprise nucleic acid molecules which include nucleotide sequences from mutant nucleotide target sequences in a plurality of samples, while the plurality of second secondary polymerase chain reactions potentially comprise nucleic acid molecules which include nucleotide sequences from mutant nucleotide target sequences in the plurality of samples, the first and second secondary polymerase chain reaction mixtures producing complementary secondary extension products that are labeled.

Desirably, the label is provided on one of the first or second secondary oligonucleotide primers. Alternatively, the label is provided on both of the first or second secondary oligonucleotide primers. The unlabeled secondary oligonucleotide primers can alternatively contain 5' phosphate groups.

For a particular secondary oligonucleotide primer set, the first secondary oligonucleotide primer and second secondary oligonucleotide primer have nucleotide sequences which are substantially similar at their 5' ends, but contain differences at their 3' ends.

Another aspect of the present invention relates to a method for identifying one or more mutant nucleotide target sequences differing by one or more single-base changes, insertions, or deletions, from a normal nucleotide target sequence. This method involves providing one or more sample(s) potentially containing the normal nucleotide target sequences, one or more mutant nucleotide target sequences, or both. This involves providing a group of one or more primary oligonucleotide primer sets, each set characterized by (a) a first oligonucleotide primer, having a target-specific portion, and (b) a second oligonucleotide primer, having a target-specific portion, where only one of the primary oligonucleotide primers is provided with a label. A polymerase is provided, and the sample, the primary oligonucleotide primer sets, and a polymerase are blended to form one or more primary polymerase chain reaction mixture(s). The primary polymerase chain reaction mixture is subjected to one or more polymerase chain reaction cycles to form primary extension products complementary to the normal nucleotide target sequence and the mutant nucleotide target sequence present in the sample. The polymerase is inactivated, and the primary polymerase chain reaction mixture(s) is subjected to a process which converts the secondary extension products to a single-stranded form and anneals the single-stranded secondary extension products to form heteroduplexed products potentially comprising nucleic acid molecules which include nucleotide sequences from the normal nucleotide target sequence and from the mutant nucleotide target sequences. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves the heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. A terminal transferase is provided, and the potentially nicked or cleaved heteroduplexed products from the ligase resealing reaction mixture and the terminal transferase are blended to form a terminal transferase extension reaction mixture. The terminal transferase extension reaction mixture is incubated with a single dNTP to extend nicked or cleaved heteroduplexed products at newly generated 3' OH groups to form terminal transferase extension products. One or more tertiary oligonucleotide primers suitable for hybridization to the newly generated terminal transferase extension products and suitable for 3' end extension are provided. The terminal transferase extension products, the tertiary oligonucleotide primers, and a polymerase are blended to form a tertiary polymerase extension reaction mixture. The tertiary polymerase extension reaction mixture is incubated under conditions allowing the tertiary oligonucleotide primers to hybridize to the terminal transferase extension products, and polymerase to produce tertiary extension products, which are complementary copies of the terminal transferase extension products, containing sites of mismatch and adjacent target-specific sequences. A group of one or more quaternary oligonucleotide primer sets, each set characterized by (a) a first quaternary oligonucleotide primer, having a tertiary extension product-specific portion and a 5' upstream quinternary primer-specific portion, and (b) a second quaternary oligonucleotide primer, having a tertiary extension product-specific portion and a 5' upstream quinternary primer-specific portion. The tertiary extension products, the quaternary oligonucleotide primers, and a polymerase are blended to form one or more quaternary extension reaction mixture(s). The one or more quaternary polymerase chain reaction mixture(s) is subjected to one or more quaternary polymerase chain reaction cycles to form a quaternary extension product. A group of one or more quinternary oligonucleotide primer sets, each set characterized by (a) a first quinternary oligonucleotide primer, having the same sequence as the 5' upstream portion of the first quaternary oligonucleotide primer, and (b) a second quinternary oligonucleotide primer, containing the same sequence as the 5' upstream portion of the second quaternary oligonucleotide, is provided. The quaternary extension product, the group of one or more quinternary oligonucleotide primer sets, and a polymerase are blended to form a quinternary polymerase chain reaction mixture(s). The quinternary polymerase chain reaction mixture(s) is subjected to one or more quinternary polymerase chain reaction cycles to form a quinternary extension product complementary to the quaternary extension product. Products resulting from subjecting the ligase resealing reaction mixture to a ligase resealing reaction are separated by size or electrophoretic mobility or hybridization to capture probes attached to a solid support. The presence of the normal nucleotide target sequence and the one or more mutant nucleotide target sequences in the sample are detected by distinguishing the separated products resulting from the ligase resealing reaction.

FIG. 8 is a schematic diagram, illustrating an improved procedure for EndoV/Ligase mutation scanning assay with gene-specific array detection. Heteroduplexed DNA of one or more fragments is generated as described in FIGS. 4-7. An endonuclease (EndoV) is used to preferentially nick DNA one base to the 3' side of mismatches, while a ligase is used to reseal background nicks at perfect match regions. The EndoV and Ligase reactions may be performed in a single step. The newly generated 3'OH is extended using terminal transferase and dGTP. A primer containing 2 unique bases on 3' end (e.g. AT), C8, encoding sequence (e.g. E1) and a universal sequence (Un1) on the 5' end, is annealed and extended with Taq DNA polymerase. A gene-specific upstream primer containing a universal sequence (Un2) on the 5' end, phosphorylated Un2 primer, and fluorescently-labeled Un1 primer, are used to PCR amplify a fragment using Taq DNA polymerase and dNTP's containing a low concentration of dUTP. The PCR products are then nicked one base to the 3' side of uracil bases using Endonuclease V. The nicked PCR products are digested using lambda exonuclease. Only the 5' labeled single-stranded fragment containing approximately 20 to 50 bases of gene-specific sequence adjacent to and including the site of mismatch will remain. The labeled fragment(s) are then hybridized on an array containing tiling of gene sequences, to identify approximate position of mismatch. A separate procedure with opposite strand primers would be performed on an array containing complementary sequences to determine the presence of mismatches on the complementary strand. As shown in FIG. 8, fluorescent signal corresponding to bases 150-200 indicates presence of a mutation in the middle of Exon 1. The mutation containing fragment(s) may be sequenced individually from the PCR products, by reamplifying with a gene-specific primer and a primer containing a unique encoding sequence (e.g. E1) and the universal Un1 sequence.

FIG. 9 is a schematic diagram, illustrating an improved procedure for EndoV/Ligase mutation scanning assay of multiple exons with gene-specific array detection. Heteroduplexed DNA of one or more fragments containing multiple exons is generated as described in FIGS. 4-7. An endonuclease (EndoV) is used to preferentially nick DNA one base to the 3' side of mismatches, while a ligase is used to reseal background nicks at perfect match regions. The EndoV and Ligase reactions may be performed in a single step. The newly generated 3'OH is extended using terminal transferase and dGTP. A primer containing 2 unique bases on 3' end (e.g. AC, GT), C8, encoding sequence (e.g. E1, E2) and a universal sequence (Un1) on the 5' end, is annealed and extended with Taq DNA polymerase. A gene-specific upstream primer containing a universal sequence (Un2) on the 5' end, phosphorylated Un2 primer, and fluorescently-labeled Un1 primer, are used to PCR amplify a fragment using Taq DNA polymerase and dNTP's. The presence of blocking oligonucleotides assure the desired PCR products dominate. The PCR products are digested using lambda exonuclease. Only the 5'-labeled single-stranded fragment, which contains a gene-specific sequence adjacent to and including the site of mismatch, will remain. The labeled fragment(s) are then hybridized on an array containing tiling of exon sequences, to identify exons containing mismatches. A separate procedure with opposite strand primers would be performed on an array containing complementary sequences to determine presence of mismatches on the complementary strand. As shown in FIG. 9, fluorescent signal at both the Exon 1 and Exon 2 gene-specific addresses indicates presence of mutations (or polymorphisms) in both Exon 1 and Exon 2. The mutation containing fragment(s) may be sequenced individually from the PCR products, by reamplifying with an exon-specific primer and a primer containing a unique encoding sequence (e.g. E1, E2) and the universal Un1 sequence.

FIG. 11 is a schematic diagram, illustrating an improved procedure for EndoV/Ligase mutation scanning assay with universal array detection. Heteroduplexed DNA of one or more fragments is generated as described in FIGS. 4-7. An endonuclease (EndoV) is used to preferentially nick DNA one base to the 3' side of mismatches, while a ligase is used to reseal background nicks at perfect match regions. The EndoV and ligase reactions may be performed in a single step. The newly generated 3'OH is extended using terminal transferase and dGTP. A primer, containing 2 unique bases on the 3' end (e.g. AT), C8, encoding sequence (e.g. E1), and a universal sequence (Un1) on the 5' end, is annealed and extended with Taq DNA polymerase. A gene-specific upstream primer containing a zipcode sequence and a universal sequence (Un2) on the 5' end, phosphorylated Un2 primer, and fluorescently-labeled Un1 primer, are used to PCR amplify the fragment(s) using Taq DNA polymerase and dNTP's. Multiple primers with different zipcodes are available, but the shortest PCR product dominates. The PCR products are converted to a single stranded form using lambda exonuclease. Only the 5'-labeled single-stranded fragment containing bases of gene-specific sequence adjacent to and including the site of mismatch will remain. The labeled fragment(s) are subsequently hybridized on a universal array containing zipcode sequences to identify the approximate position of mismatch. In this illustration, fluorescent signal at address Zp2 indicates presence of a mutation in the middle of Exon 1. A separate procedure with opposite strand primers would be performed to determine the presence of mismatches on the complementary strand. The mutation containing fragment(s) may be sequenced individually from the PCR products by reamplifying with the specific zipcode primer and a primer containing a unique encoding sequence E1 and the universal Un1 sequence.

FIG. 12 is a schematic diagram, illustrating an improved procedure for EndoV/Ligase mutation scanning assay of multiple exons with universal array detection. Heteroduplexed DNA of one or more fragments containing multiple exons is generated as described in FIGS. 4-7. An endonuclease (EndoV) is used to preferentially nick DNA one base to the 3' side of mismatches, while a ligase is used to reseal background nicks at perfect match regions. The EndoV and Ligase reactions may be performed in a single step. The newly generated 3'OH is extended using terminal transferase and dGTP. A primer containing 2 unique bases on 3' end (e.g. AC, GT), C8, encoding sequence (e.g. E1, E2), and a universal sequence (Un1) on the 5' end is annealed and extended with Taq DNA polymerase. A gene-specific upstream primer containing a zipcode sequence and a universal sequence (Un2) on the 5' end, phosphorylated Un2 primer, and fluorescently labeled Un1 primer, are used to PCR amplify the fragment(s) with Taq DNA polymerase and dNTP's. Multiple primers with different zipcodes are available to assure amplification of mutations associated with specific polymorphisms. The presence of blocking oligonucleotides assures the desired PCR products dominate. The PCR products are converted to a single stranded form using lambda exonuclease. Only the 5' labeled single-stranded fragment containing bases of gene-specific sequence adjacent to and including the site of mismatch will remain. The labeled fragment(s) are subsequently hybridized on a universal array containing zipcode sequences to identify approximate position of mismatch. As shown in FIG. 12, a fluorescent signal at address Zp2 indicates a mutation is present on the G-allele of Exon 1, while a fluorescent signal at address Zp3 indicates a mutation is present on Exon 2. A separate procedure with opposite strand primers would be performed to determine presence of mismatches on the complementary strand. The mutation containing fragment(s) may be sequenced individually from the PCR products, by reamplifying with the specific zipcode primer and a primer containing a unique encoding sequence (e.g. E1, E2) and the universal Un1 sequence.

Terminal Transferase is a polymerase that works in a template independent fashion and adds deoxynucleotides to the 3' hydroxyl terminus of DNA. It can work on 5' overhang, 3' overhang, blunt end, or single-stranded molecules with an unblocked 3' end. It is commercially available from New England Biolabs (Beverly, Mass., USA), where the enzyme is isolated from an *E. coli* strain that carries the cloned terminal transferase gene from calf thymus. (Chang et al., *CRC Crit. Rev Biochem.* 21(1):27-52 (1986); Roychoudhury et al., *Nucl. Acids Res.* 3: 101-116 (1976); Tu et al., *Gene* 10:177-183 (1980); and Boule et al., *J. Biol. Chem.* 276, 31388-31393 (2001), which are hereby incorporated by reference in their entirety). The purpose of adding terminal transferase is to generate a tail of mononucleotides (in this case, G(n)) to which a primer can subsequently hybridize and be used to PCR amplify the unique fragment generated by EndoV cleavage 3' to the site of a mutation or polymorphism.

The tertiary oligonucleotide primers contain additional unique mutation identifier sequences that correspond to the 2 unique bases on their 3' ends.

This aspect of the present invention permits detection of a solid support (e.g., using an array format) as fully described in WO 97/31256 to Cornell Research Foundation, Inc., et al., which is hereby incorporated by reference in its entirety. In particular, a solid support with different capture oligonucleotides immobilized at different sites on the solid support is provided where the capture oligonucleotides have nucleotide sequences complementary to tertiary extension product-specific portions. The quintenary polymerase chain reaction mixture(s) are contacted with the solid support under conditions effective to hybridize the quintenary extension product to the capture oligonucleotides in a base-specific manner. The presence of quintenary extension product captured using the tertiary extension product-specific portions and immobilized to the solid support at particular sites is detected. This indicates the presence of one or more mutant target nucleotide sequences in the sample.

In a particularly preferred embodiment of the present invention, two solid supports are provided. The first support contains a first set of different capture oligonucleotides immobilized at different sites on the first solid support, where the first set of capture oligonucleotides are complementary to one strand of the tertiary extension product. The second support contains a second set of different capture oligonucleotides immobilized at different sites on the second solid support, where the second set of capture oligonucleotides have nucleotide sequences complementary to the complementary strand of the tertiary extension product. In this aspect of the present invention, the capture oligonucleotides are from 20 to 1,500 bases in length and correspond to exons and adjacent nucleotide sequences of the target genes.

The tertiary oligonucleotide primers can contain additional unique mutation identifier sequences that correspond to the 2 unique bases on their 3' ends. A pair of labeled hexanary oligonucleotide primer(s) complementary to the unique mutation identifier sequences and/or the 5' upstream quintenary primer-specific portion are provided. The labeled oligonucleotide primers are hybridized onto nucleic acid molecules immobilized on the solid support to permit the immobilized nucleic acid molecules to be distinguished.

Another aspect of the present invention involves providing one or more sets of hexanary oligonucleotides comprising (a) a first hexanary oligonucleotide primer containing a tertiary extension product-specific sequence and (b) a second hexanary oligonucleotide primer containing a sequence from the unique mutation identifier sequences and/or the 5' upstream quintenary primer-specific portion of the corresponding second oligonucleotide primer in the quaternary oligonucleotide primer set. The quintenary extension products, the one set of hexanary oligonucleotide primers, and the polymerase are blended to form one or more hexanary polymerase chain reaction mixture(s). The hexanary polymerase chain reaction mixture(s) are subjected to two or more polymerase chain reaction cycles to form hexanary polymerase chain reaction extension products complementary to the quintenary extension products. The one or more hexanary polymerase chain reaction products are sequenced where one or more mutations are present.

The tertiary oligonucleotide primers can contain 2 unique bases on their 3' end, followed by a mononucleotide repeat sequence complementary to the dNTP used in the terminal transferase extension reaction, and a 5' upstream secondary primer-specific portion.

The quintenary extension product can be fragmented to generate fragments containing unique target-specific sequences of average length of 20-50 bases. In carrying out this embodiment, the quintenary polymerase chain reaction cycles are carried out in the presence of dUTP. As a result, uracil is incorporated in the quintenary extension product, on average every 20 to 50 bases. Fragmenting can be carried out with EndonucleaseV or with DNaseI. All non 5' end fragments of the quintenary extension product can be digested with exonuclease to achieve an enriched quantity of fragments containing approximately 20 to 50 bases adjacent to and including the site of the mismatch. The 5' fragments containing approximately 20 to 50 bases adjacent to and including the site of the mismatch are protected from exonuclease digestion by either a label or a 5' end blocking group.

Another aspect of the present invention relates to a method for identifying one or more mutant nucleotide target sequences differing by one or more single-base changes, insertions, or deletions, from a normal nucleotide target sequences. This involves providing one or more sample(s) potentially containing the normal nucleotide target sequences, one or more mutant nucleotide target sequences, or both. Also provided is a group of one or more primary oligonucleotide primer sets, each set characterized by (a) a first oligonucleotide primer, having a target-specific portion, and (b) a second oligonucleotide primer, having a target-specific portion. Only one of the primary oligonucleotide primers is provided with a label. A polymerase is provided, and the sample, the primary oligonucleotide primer sets, and the polymerase are blended to form one or more primary polymerase chain reaction mixture(s). The primary polymerase chain reaction mixture is subjected to one or more polymerase chain reaction cycles to form primary extension products complementary to the normal nucleotide target sequences and the mutant nucleotide target sequences present in the sample. The polymerase is inactivated, and the primary polymerase chain reaction mixture(s) is subjected to a process which converts the primary extension products to a single-stranded form and anneals the single-stranded primary extension products to form heteroduplexed products potentially comprising nucleic acid molecules which include nucleotide sequences from the normal nucleotide target sequences and from the mutant nucleotide sequences. An endonuclease, which preferentially nicks or cleaves heteroduplexed DNA at a location within one base away from mismatched base pairs, is provided, and the heteroduplexed products and the endonuclease are blended to form an endonuclease cleavage reaction mixture. The endonuclease cleavage reaction mixture is subjected to an endonuclease cleavage reaction so that the endonuclease preferentially nicks or cleaves the heteroduplexed products at a location within one base away from mismatched base pairs. A ligase is provided, and the endonuclease cleavage reaction mixture and the ligase are blended to form a ligase resealing reaction mixture. The ligase resealing reaction mixture is subjected to a ligase resealing reaction to seal the nicked heteroduplexed products at perfectly matched base pairs but with substantially no resealing of nicked heteroduplexed products at locations adjacent to mismatched base pairs. One or more tertiary oligonucleotide primers suitable for hybridization to the 5' end of a strand of the nicked heteroduplex products which have been sealed is provided, and the ligase resealing reaction mixture after resealing, the tertiary oligonucleotide primers, and a polymerase are blended to form a tertiary polymerase extension reaction mixture. The tertiary polymerase extension reaction mixture is incubated under conditions allowing for the tertiary oligonucleotide primers to hybridize to a strand of the nicked heteroduplex products which has been sealed and the polymerase to produce tertiary extension products. A blunt end linker and a ligase with blunt end activity are provided. The tertiary extension products, the blunt end linker, and the ligase with blunt end activity are blended to form a blunt end ligase reaction mixture. The blunt end ligase reaction mixture is incubated under conditions effective to ligate the blunt end linker to tertiary extension products and produce blunt end ligation products. A plurality of quaternary oligonucleotide primer sets, each set characterized by (a) a first quaternary oligonucleotide primer, having a blunt end ligation product-specific portion and a 5' upstream quintenary primer-specific portion, and (b) a second quaternary oligonucleotide primer, having a linker-specific portion, is provided. The blunt end ligation products, the quaternary oligonucleotide primer sets, and a polymerase are blended to form one or more quaternary polymerase chain reaction mixture(s). The one or more quaternary polymerase chain reaction mixture(s) is subjected to one or more polymerase chain reaction cycles to form a quaternary extension product. A quintenary oligonucleotide primer, having the same sequence as the 5' upstream portion of a first quaternary oligonucleotide primer, is provided, and the quintenary oligonucleotide primer, quaternary polymerase extension product, and a polymerase are blended to form a quintenary polymerase chain reaction mixture. The one or more quintenary polymerase chain reaction mixture is subjected to one or more polymerase chain reaction cycles to form a quintenary extension product. Products resulting from subjecting the one or more quintenary polymerase chain reaction mixture to one or more polymerase chain reaction cycles are separated by size or electrophoretic mobility or hybridization to capture probes attached to a solid support. The presence of the normal nucleotide target sequences and the one or more mutant nucleotide target sequences in the sample is detected by distinguishing the separated products resulting from the quintenary polymerase chain reaction.

FIG. 10 is a schematic diagram, illustrating an improved procedure for EndoV/Ligase mutation scanning assay with gene-specific array detection. Heteroduplexed DNA of one or more fragments is generated as described in FIGS. 4-7. An endonuclease (EndoV) is used to preferentially nick DNA one base to the 3' side of mismatches, while a ligase is used to reseal background nicks at perfect match regions. The EndoV and Ligase reactions may be performed in a single step. A downstream gene-specific primer is annealed to denatured fragments and extended to create a blunt end with newly generated 5' phosphate. A linker containing universal Un1 sequence is ligated unto this newly generated blunt end with T4 ligase. A gene-specific downstream primer containing a universal sequence (Un2) on the 5' end, phosphorylated Un2 primer, and fluorescently labeled Un1 primer are used to PCR amplify fragments using Taq DNA polymerase and dNTP's containing a low concentration of dUTP. The PCR products are then nicked one base to the 3' side of uracil bases using Endonuclease V. The nicked PCR products are digested using lambda exonuclease. Only the 5'-labeled single-stranded fragment containing approximately 20 to 50 bases of gene-specific sequence adjacent to the site of mismatch will remain. The labeled fragment(s) are then hybridized on an array containing tiling of gene sequences to identify the approximate position of mismatch. A separate procedure with opposite strand primers would be performed on an array containing complementary sequences to determine the presence of mismatches on the complementary strand. As shown in FIG. 10, fluorescent signal corresponding to bases 200-250 indicates presence of a mutation in the middle of Exon 1.

There are several ligase enzymes that demonstrate blunt end ligation activity. T4 ligase has strong blunt end activity, and this may be enhanced by addition of molecular crowding agents, such as PEG (Maniatis, T., *Molecular Cloning: A Laboratory Manual*, (2nd Ed.), section 1.53-1.73 (1989); Weiss, B. et al., *J. Biol. Chem.*, 243:4543-4555 (1968), which are hereby incorporated by reference in their entirety). Blunt end activity is needed to ligate a linker onto a newly generated phosphorylated 5' end that is liberated by EndoV cleavage 3' to the site of a mutation or polymorphism, and then rendered blunt end by extending a primer hybridized to that strand.

In this embodiment of the present invention, blocking oligonucleotide primers are added to the quintenary polymerase chain reaction mixture to suppress amplification of full length or other amplification products which would interfere with said detecting. The blocking oligonucleotide primers are comprised of tertiary extension product-specific portions upstream of the tertiary extension product-specific portion of the one or more first quaternary oligonucleotide primers. Suitable blocking oligonucleotide primers are comprised of PNA, 2'-o-methyl groups, and/or 5-propinyl-dU and 5-propinyl-dC containing oligonucleotides.

EXAMPLES

Example 1

Standard Procedure: PCR Amplification with Primers Fluorescently Labeled on their 5'-End with Tet and Fam All routine chemical reagents were purchased from Sigma Chemicals (St. Louis, Mo., USA) or Fisher Scientific (Fair-Lawn, N.J., USA). GeneScan-500 (TAMRA) size standard, GeneScan-500 LIZ™ size standard, Hi-Di formamide, polymer POP7 and PCR kits were purchased from Applied Biosystems Division of Perkin-Elmer Corporation (Foster City Calif.). Deoxyribonucleoside triphosphate (dNTPs), bovine serum albumin (BSA), ATP, were purchased from Boehringer-Mannheim (Indianapolis, Ind., USA). Proteinase K was purchased from QIAGEN (Valencia, Calif., USA). Deoxyoligonucleotides were ordered from Integrated DNA Technologies Inc. (Coralville, Iowa, USA) and Applied Biosystems Division of Perkin-Elmer Corporation (Foster City, Calif.). *Thermotoga maritima* Endonuclease V and Thermus species AK16D DNA ligase were purified as described (Huang et al., *Biochemistry* 40(30):8738-48 (2001); Tong et al., *Nucleic Acids Res.* 27(3):788-94 (1999), which are hereby incorporated by reference in their entirety). Genomic DNA was extracted from cell lines as described (Khanna et al., *Oncogene* 18(1):27-38 (1999), which is hereby incorporated by reference in its entirety). Cell lines HT29 contain the wild-type K-ras. For detecting K-ras mutations, genomic DNA was extracted from cell lines as described (Khanna et al., *Oncogene* 18(1):27-38 (1999), which is hereby incorporated by reference in its entirety). SW620 and SW480 contain the K-ras G12V (G->T) mutation.

Fluorescent group 6-Fam is (3',6'-dippivaloylfluoresceinyl)-6-carbox-amidohexyl)-1-O-(2-cyanoethyl)-(N,N-diisopropyl)-phosphor-amidite. Vic and Ned are patent pending dyes developed by ABI (Applied Biosystems, Foster, Calif.).

Genomic DNA was extracted from cell lines containing mutation R273H (G->A) in exon 8 of p53 gene (HT-29, SW480 or SW620 cell line), as well as a cell line containing wild-type p53 gene (LoVo cell line). PCR amplification of p53 exon 8 used forward and reverse gene-specific primers that were 5'-end fluorescently labeled with Tet and 6-Fam, respectively. DNA sequences of these primers, named Tet-p53ex8 11F and Fam-p53ex8 12R, respectively, are listed in Table 2. Wild-type and mutant genomic DNA were PCR amplified in a 50-μl reaction mixture containing 20 mM Tricine pH 8.7, 16 mM $(NH_4)_2SO_4$, 2.5 mM $MgCl_2$, 250 μM of each dNTP, 0.2 μM of the gene-specific primer pair, 5 units of AmpliTaq Gold (Applied Biosystems, Foster City, Calif.), and 150 ng genomic DNA. The PCR thermo-cycle conditions for p53exon 8 were as follows: 95° C. for 10 min, 35 cycles of 94° C. for 20 s, 60° C. for 30 s, 72° C. for 1 min, followed by a final extension step at 72° C. for 7 min. The two fluorescent groups Tet and 6-Fam appear green and blue, respectively, when visualized on the ABI-377 DNA sequencer. Differential labeling of the top and bottom strands is used to distinguish cleavage products from each strand independently.

TABLE 2

PCR primers used for analysis on the ABI-377 sequencer

| Gene | Exon | Primer name | Primer sequence |
|---|---|---|---|
| p53 | Exon 8 | Tet-p53ex8 11F | 5' Tet-CCCCGGACAGGTAGGACCTGATTTCCTTAC-3' (SEQ ID NO: 1) |
| | | Fam-p53ex8 12R | 5' Fam-CCCCGCTTCTTGTCCTGCTTGCTTAC-' (SEQ ID NO: 2) |

TABLE 2-continued

PCR primers used for analysis on the ABI-377 sequencer

| Gene | Exon | Primer name | Primer sequence |
|------|------|-------------|-----------------|
|      |      | p-p53ex8 11F | 5' p-CCCCGGACAGGTAGGAGCTGATTTCCTTAC-' (SEQ ID NO: 3) |
|      |      | p-p53ex8 12R | 5' p-CCCCGCTTCTTGTCCTGCTTGCTTAC-' (SEQ ID NO: 4) |

F = Forward primer
R = Reverse primer

Example 2

Standard Denaturation/Renaturation Procedure: Preparation of Fluorescently Labeled Heteroduplex DNA Substrates Aliquots (4 µl) of the p53 exon 8 PCR products were analyzed on a 2% agarose gel, and quantified using the Gel-Doc 2000 imager with Quantity One software (BioRad, Hercules, Calif.). Approximately equal ratios of wild-type PCR amplicons were mixed with mutant (R273H, G->A) PCR amplicons in a 12 µl final volume, with a total of ~1500 ng DNA. The wild-type control consisted of wild-type DNA PCR products alone in a 12 µl final volume (~1500 ng total DNA). In order to inactivate Taq DNA polymerase, 1 µl of proteinase K (20 mg/ml, Qiagen, Valencia, Calif.) was added to each PCR mixture, including the wild-type control, and incubated at 65° C. for 30 min. This was followed by a 10 min incubation at 80° C. to inactivate the proteinase K. PCR mixtures were then heated at 95° C. for 2 min, and gradually cooled down to room temperature in a GeneAmp PCR System 960 thermo-cycling machine (Applied Biosystems/Perkin-Elmer, Foster City, Calif.) using the following PCR program: 95° C. for 2 min, 95° C. for 15 s, followed by a 0.2° C. decrease in temperature every 15 s down to 45° C., and finally by 10 min at 25° C. Thus, denaturation/reannealing of the wild-type+mutant (R273H, G->A) p53 exon 8 PCR mixtures generates 50% of heteroduplexes (both G/T and A/C mismatches), as well as 50% of G:C homoduplexes, while denaturation/reannealing of the wild-type control leads to the formation of 100% of G:C homoduplexes. Similarly, denaturation/reannealing of the wild-type+mutant (G12V, G->T) K-ras exon 1 PCR mixtures generates 50% of heteroduplexes (both G/A and T/C mismatches), as well as 50% of G-C homoduplexes, while denaturation/reannealing of the wild-type control leads to the formation of 100% of G:C homoduplexes. This step was followed by the EndoV/Ligase cleavage/resealing reactions. The steps in this example are illustrated in FIG. 3.

Example 3

Performing the EndoV/Ligase Mutation Scanning Assay Under the Standard Conditions: Analysis on the ABI-377 Sequencer The EndoV/Ligase assay was performed under the standard two-step reaction conditions, (+EndoV, +Ligase reactions), as described below:
1. Half the volume (~6.5 µl) of each heteroduplex mixture, including the wild-type homoduplex control, was incubated for 40 min at 65° C. in a 20-µl reaction mixture containing 20 mM Hepes pH 7.5, 5 mM $MgCl_2$, 1 mM DTT, 2% glycerol, 5% DMSO, 1.5 M betaine and 1 µM EndoV.
2. Fifteen µl of each EndoV cleavage reaction mixture were then subjected to the Ligase reaction in a 20-µl final volume during a 30-min incubation at 65° C. This was done by adding 2 µl of 10×supplemental buffer (200 mM Tris pH 8.5, 12.5 mM $MgCl_2$, 500 mM KCl, 10 mM DTT, 200 µg/ml BSA), 1 µl of 20 mM NAD, and 2 µl of 30 nM Ligase.

In parallel, each heteroduplex mixture, including the wild-type homoduplex control, was subjected to the same protocol, except that both EndoV and ligase were replaced by water (-EndoV, -Ligase control reactions).

To terminate each Ligase reaction, 4-µl aliquots were mixed with equal volumes of stop-solution composed of 75% formamide and 25% (3% blue dextran, 50 mM EDTA), denatured at 95° C. for 1 min, and put on ice. Finally, 2.5-µl aliquots were loaded onto a 6% acrylamide/bisacrylamide (19:1) and 0.2 mm thick denaturing gel containing 6 M urea and electrophoresed for 2 h at 1500 V in TBE buffer (90 mM Tris-Borate, pH 8.3, 2 mM EDTA) at 45° C. in the ABI-377 sequencer. Data were analyzed using GeneScan analysis software version 3.1 (Applied Biosystems, Foster City, Calif.). At completion of the electrophoretic run, a gel image was displayed on the instrument monitor, with Tet- and Fam-labeled fragments appearing in green and blue, respectively.

Example 4

Lambda Exonuclease Procedure: PCR Amplification with a 5'-End (Tet- or Fam-) Fluorescently Labeled Primer and a 5'-Phosphorylated Primer The lambda exonuclease procedure is used to generate DNA heteroduplexes that are of only one type, i.e. G/T or A/C. This results in a reduction of the signal-to-noise background of the EndoV/Ligase mutation scanning assay. As previously described, genomic DNA was extracted from cell lines containing mutation R273H (G->A) in exon 8 of p53 gene (HT-29, SW480 or SW620 cell line), as well as from a cell line containing wild-type p53 gene (LoVo cell line). Both wild-type and mutant (R273H) genomic DNA were subjected to 2 parallel PCR amplifications. A first PCR amplification of p53 exon 8 used a forward 5'-end Tet-labeled primer and a reverse 5'-phosphorylated primer. In parallel, a second PCR amplification of p53 exon 8 used a forward 5'-phosphorylated primer and a reverse 5'-end Fam-labeled primer. DNA sequences of these primers, named Tet-p53ex8 11F, p-p53ex8 12R, p-p53ex8 11F, and Fam-p53ex8 12R, respectively, are listed in Table 2 (above). These steps are illustrated in FIG. 2.

The PCR reaction mixture (50 µl) contained 20 mM Tricine pH 8.7, 16 mM $(NH_4)_2SO_4$, 2.5 mM $MgCl_2$, 250 µM of each dNTP, 0.2 µM of the gene-specific primer pair, 5 units of AmpliTaq Gold (Applied Biosystems, Foster City, Calif.), and 150 ng genomic DNA. The PCR thermo-cycle conditions for p53exon 8 were as follows: 95° C. for 10 min, 35 cycles of 94° C. for 20 s, 60° C. for 30 s, 72° C. for 1 min, followed by a final extension step at 72° C. for 7 min.

Primers were phosphorylated on their 5'-end prior to PCR amplification by incubating 200 pmol of each primer (namely, p-p53ex8 11F or p-p53ex8 12R) with 10 units of T4 polynucleotide kinase (New England Biolabs, Beverly, Mass.) for 1 h at 37° C. in a 25 μl of reaction mixture containing 1× T4 polynucleotide kinase buffer (70 mM Tris-HCl pH 7.6, 10 mM $MgCl_2$, and 5 mM DTT) and 1 mM ATP. The enzyme was then heat inactivated for 20 min at 65° C., and small aliquots of the phosphorylation reaction were stored at −20° C. The two fluorescent groups Tet and Fam appear green and blue, respectively, when visualized on the ABI-377 DNA sequencer. Differential labeling of the top and bottom strands is used to distinguish cleavage products from each strand independently.

Example 5

Lambda Exonuclease Procedure: Preparation of Fluorescently-Labeled Heteroduplex DNA Substrates Aliquots (4 μl) of the p53 exon 8 PCR products were analyzed on a 2% agarose gel, and quantified using the Gel-Doc 2000 imager with Quantity One software (BioRad, Hercules, Calif.). Approximately equal ratios of the Tet-labeled wild-type p53 exon 8 PCR products were mixed with the Fam-labeled mutant p53 exon 8 (R273H G->A) PCR products in a 12 μl final volume, with a total of 1500 ng DNA (PCR mixture 1). Likewise, the Tet-labeled mutant p53 exon 8 PCR products were mixed with the Fam-labeled wild-type p53 exon 8 PCR products in another 12-μl reaction (PCR mixture 2). The wild-type control consisted of a mixture of Tet-labeled wild-type p53 exon 8 PCR products with Fam-labeled wild-type p53 exon 8 PCR products in a 12 μl final volume (~1500 ng total DNA).

In order to inactivate Taq DNA polymerase, 1 μl of proteinase K (20 mg/ml, Qiagen, Valencia, Calif.) was added to each PCR mixture, including the wild-type control, and incubated at 65° C. for 30 min. This was followed by a 10-min incubation at 80° C. to inactivate the proteinase K. PCR mixtures were then incubated at 37° C. for 1 h with 1 unit of lambda exonuclease, which degrades 5'-phosphorylated DNA. Lambda exonuclease was then heat inactivated by incubating the reaction at 75° C. for 10 min. Thus, digestion of the phosphorylated strands by lambda exonuclease was used to generate two complementary labeled strands that anneal to form 100% of heteroduplex DNA fragments. PCR mixture 1 contains heteroduplexes with a G/T mismatch, while PCR mixture 2 contains heteroduplexes with an A/C mismatch. Wild-type control leads to the formation of 100% of G:C homoduplexes. This step was followed by the EndoV/Ligase reaction.

When using fluorescent groups Vic and Ned, instead of Tet and Fam, respectively, preparation of heteroduplex DNA substrates was carried out as above, for both p53 exon 8 (R273H, G->A) and K-ras exon 1 (G12V, G->T) PCR amplicons. Consequently, the lambda exonuclease procedure applied to K-ras exon 1 (G12V, G->T) PCR amplicons was used to generate heteroduplexes with a G/A mismatch in PCR mixture 1, and heteroduplexes with an T/C mismatch in PCR mixture 2, while wild-type control led to the formation of 100% of G:C homoduplexes. The steps in this example are illustrated in FIG. 2.

Example 6

Improvement of Signal-to-Noise Ratio in the Detection of p53 exon 8 R273H Mutation by Using Lambda Exonuclease Procedure Prior to the EndoV/Ligase Reaction Exon 8 of p53 has always generated high levels of background cleavage under the standard conditions. Therefore, this gene was used as a model system to test conditions that improve the signal-to-noise ratio of the EndoV/ligase reaction.

Figure 13:
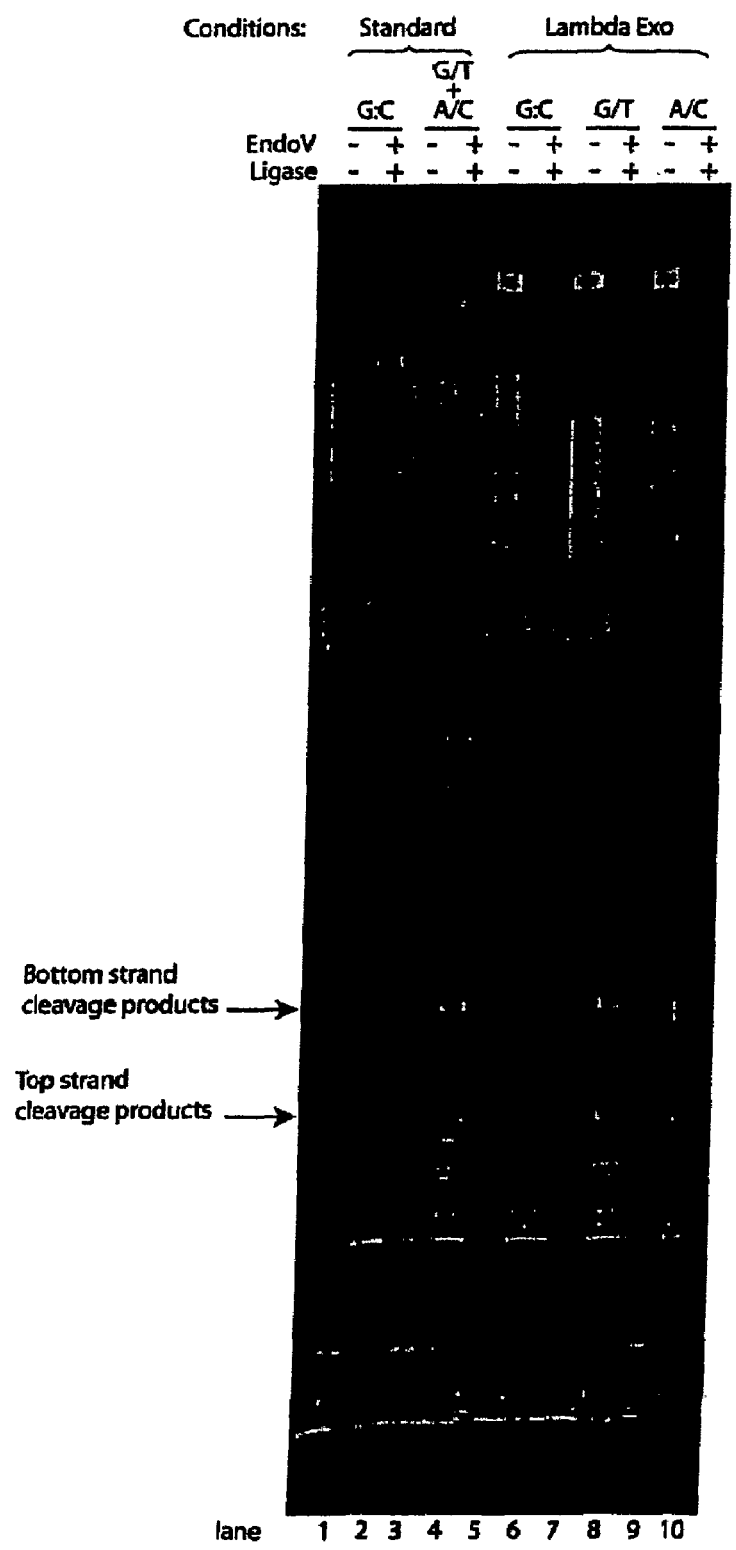
FIG. 13 is an electrophoretogram of EndoV/Ligase cleavage products of heteroduplexed DNA containing the p53 exon 8 R273H mutation. This figure illustrates an improvement of signal intensity as well as the signal-to-noise ratio when using the lambda exonuclease to generate pure G/T and A/C heteroduplexes, compared with the standard heat denaturation/renaturation, which generates both G/T and A/C heteroduplex mismatches as well as the G:C and A:T homoduplex matches. DNA from both wild-type and R273H mutant cell lines was individually PCR amplified using Tet- and Fam-labeled PCR primers for p53 exon 8. PCR products were mixed to allow for generating either homoduplexed or heteroduplexed substrates. For reactions requiring lambda exonuclease digestion, either the top or bottom PCR primer was phosphorylated on the 5' end. Each PCR mixture was either treated with EndoV/Ligase (EndoV (+) and Ligase (+)), or untreated (EndoV (−) and Ligase (−)), as a negative control. Lanes 1-4 show EndoV/Ligase reactions performed on DNA substrates that have undergone the standard denaturation/renaturation conditions (95° C. for 2 min, followed by gradual cooling from 95° C. to 45° C. over 1 hour). Lanes 5-10 show reactions performed on DNA substrates that were rendered single-stranded by lambda exonuclease, allowing the resultant complementary single strands to reanneal and form the heteroduplexes. Under the standard conditions, wild-type/mutant PCR mixtures contain heteroduplexes with G/T+A/C mismatches (lanes 3,4). Wild-type PCR fragments were used as controls (G:C match, lanes 1,2). Under the lambda exonuclease procedure, two distinct types of wild-type/mutant PCR mixtures were subjected to the EndoV reaction: heteroduplexes of top strand wild-type: bottom strand mutant (G/T mismatch, lanes 7,8) and heteroduplexes of top strand mutant: bottom strand wild-type (A/C mismatch, lanes 9,10). Wild-type PCR mixtures were used as controls (G:C match, lanes 5,6). Reaction mixtures were electrophoresed in a 6% denaturing polyacrylamide gel in the ABI-377 sequencer, using filter C setting. The green bands were generated from the cleavage of the Tet-labeled top strand, and the blue band were generated from the cleavage of the Fam-labeled bottom strand.
Figure 14:
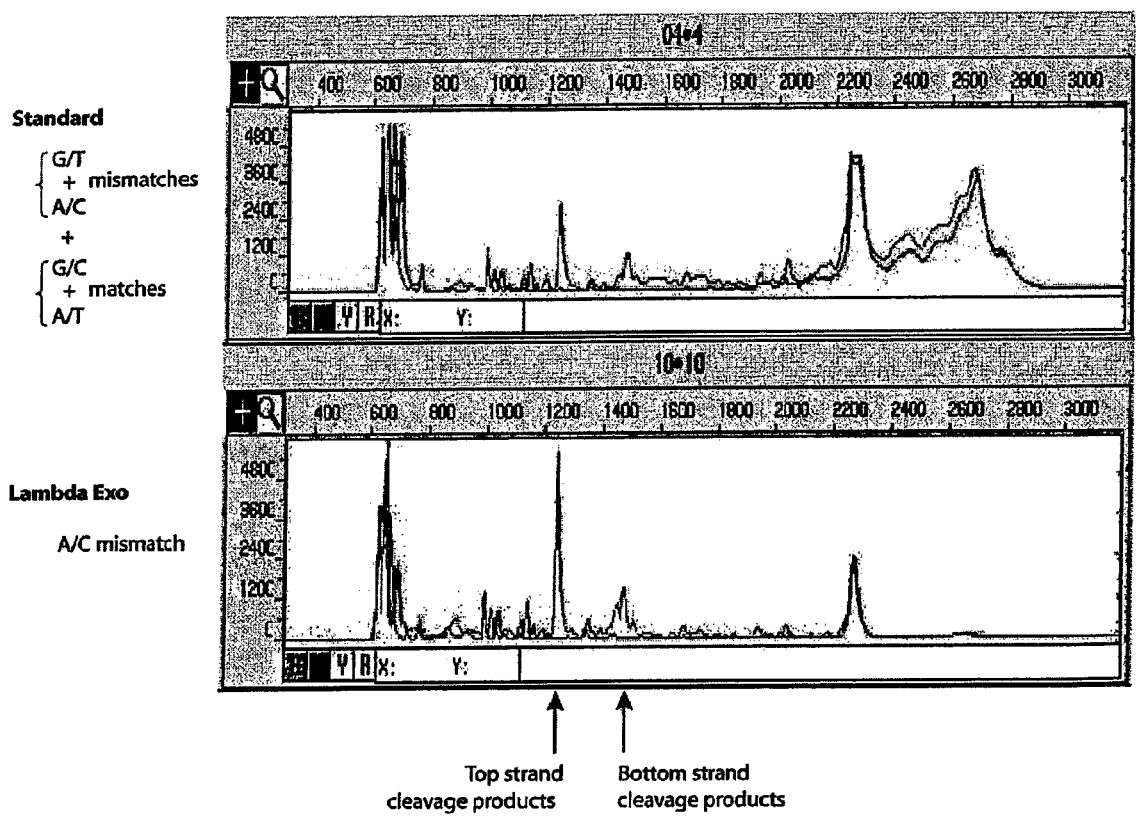
FIG. 14 presents the electrophoregrams corresponding to lanes 4 and 10 of FIG. 13. These traces provide quantitative data and were analyzed using GeneScan analysis software. The top and bottom strand EndoV cleavage products are indicated with green and blue arrows, respectively.

Exon 8 of p53 gene was PCR amplified with Tet- and Fam-labeled gene-specific primers, as described in Example 1. Wild-type and mutant (R273H) PCR products were then mixed to allow formation of heteroduplex DNA substrates using the standard procedure, as described in Example 2, and illustrated in FIG. 3. In parallel, p53 exon 8 was PCR amplified with a fluorescent primer and a 5'-phosphorylated one (and vice-versa), as described in Example 4. Wild-type and mutant (R273H) PCR products were then mixed to allow formation of heteroduplex DNA substrates using the lambda exonuclease procedure, as described in Example 5 and illustrated in FIG. 2. The EndoV/Ligase reactions were performed as described in Example 3. The gel image obtained from these experiments is presented in FIG. 13: standard conditions were run on lanes 1 through 4, including the wild-type control (G:C match) on lanes 1 and 2, while lambda exonuclease conditions were run on lanes 5 through 10, with the wild-type control on lanes 5 and 6. Top and bottom strand cleavage products are indicated with green and blue arrows, respectively. Each PCR mixture was subjected in parallel to an EndoV/Ligase reaction in the presence of EndoV and ligase, and in the absence of both EndoV and ligase, as a negative control. Wild-type G:C match, as well as G/T and A/C mismatches (i.e. [Wild-type+Mutant] mixtures) are marked on top of the lanes. Quantitative data corresponding to lanes 4 and 10—electrophoregrams derived from GeneScan analysis—are illustrated in FIG. 14. Data analysis demonstrated that the signal intensity of cleavage products (A/C mismatch) was increased by 3.1-fold and 6.9-fold for Tet and Fam signal, respectively, as compared to the standard conditions. In addition, Tet and Fam signal-to-noise ratios were increased by 3.1- and 2.3-fold, respectively. Thus, these data show that lambda exonuclease procedure significantly improves both signal intensity and signal-to-noise ratio.

Example 7

PCR Amplification with Universal Primers Fluorescently-Labeled on their 5'-End with Vic and Ned Genomic DNA was extracted from cell lines containing mutations in exon 1 of K-ras gene (codon 12) or exon 8 of p53 gene (codon 273). HT-29 cell line contains the wild-type K-ras gene, while SW480 and SW620 contain pure G12V (G->T) mutation. LoVo cell line contains wild-type p53 gene, while HT-29 SW480 and SW620 cell line contain the R273H (G->A) mutation.

PCR amplification of K-ras exon 1 was performed using two primer pairs: 1—forward and reverse universal primers VicUniEV5F and NedUniEV6R, that are fluorescently-labeled on their 5'-end with Vic and Ned, respectively; 2—forward and reverse unlabeled gene-specific primers, F161 and R162, which harbor universal tails that are just 3-bp shorter than the universal primer sequence. DNA sequences of these primers are listed in Table 3. Universal primers VicUniEV5F and NedUniEV6R have a reversed linkage label, i.e. 3'-fluorescent group-5'-universal primer sequence-3'. Wild-type and mutant genomic DNA were each subjected in a 50-μl mixture to "universal" PCR in the conditions described below.

TABLE 3

PCR primers used for analysis on the ABI-3730 DNA analyzer

| Gene | Exon | Primer name | Primer sequence | |
|---|---|---|---|---|
| Universal | | VicUniEV1F | 5' CGC(C-c6-Vic)GTCACGACACGAAAAC-3' | (SEQ ID NO: 5) |
| Universal | | NedUniEV2R | 5' CGC(C-c6-Ned)GTCACGACACGAAACA-3' | (SEQ ID NO: 6) |
| Universal | | p-UniEV1F | 5' p-CGCCGTCACGACACGAAAAC-3' | (SEQ ID NO: 7) |
| Universal | | p-UniEV2R | 5' p-CGCCGTCACGACACGAAACA-3' | (SEQ ID NO: 8) |
| Universal | | VicUniEV5F | 3'-Vic-5'-5'-CCGCCGTCACGACACGAAAAC-3' | (SEQ ID NO: 9) |
| Universal | | NedUniEV6R | 3'-Ned-5'-5'-CCGCCGTCACGACACGAAACA-3' | (SEQ ID NO: 10) |
| Universal | | p-UniEV5F | 5' p-CCGCCGTCACGACACGAAAAC-3' | (SEQ ID NO: 11) |
| Universal | | p-UniEV6R | 5' p-CCGCCGTCACGACACGAAACA-3' | (SEQ ID NO: 12) |
| K-ras | exon 1 | F161 | 5' CGTCACGACACGAAAACATAGTGTATTAACCTTATGTGTGACATGTTC-3' | (SEQ ID NO: 13) |
| | | R162 | 5' CGTCACGACACGAAACACAAAATGGTGAGAGAAACCTTTATCTGTATC-3' | (SEQ ID NO: 14) |
| p53 | exon 6 | F167 | 5' CGTCACGACACGAAAACCTCTGATTCCTCACTGATTGCTCTTA-3' | (SEQ ID NO: 15) |
| | | R168 | 5' CGTCACGACACGAAACAGGCGACTGACAACCACCCTTAAC-3' | (SEQ ID NO: 16) |
| | exon 8 | F173 | 5' CGTCACGACACGAAAACCAGGGTGGTTGGGAGTAGATG-3' | (SEQ ID NO: 17) |
| | | R174 | 5' CGTCACGACACGAAACAGGTGATAAAAGTGAATCTGAGGCATAAC-3' | (SEQ ID NO: 18) |
| | exons 8-9 | p53ex8F | 5'CGTCACGACACGAAAACTGTGGCTTCTCCTCACCTAC-3' | (SEQ ID NO: 19) |
| | | p53ex9R | 5'CGTCACGACACGAAACAGCCCCAATTGCAGGTAAAAC-3' | (SEQ ID NO: 20) |

F = Forward primer
R = Reverse primer

Similar to K-ras amplification, PCR amplification of p53 exon 8 was performed using forward and reverse universal primers VicUniEV5F and NedUniEV6R, and forward and reverse unlabeled gene-specific primers, F173 and R174. Alternatively, PCR amplification of p53 exon 8 was performed using forward and reverse universal primers VicUniEV1F and NedUniEV2R, and forward and reverse unlabeled gene-specific primers, F173 and R174. VicUniEV1F and NedUniEV2R are internally labeled with the fluorescent group—Vic or Ned—attached to the C6 of the fourth base (Cytosine 4). Internal labeling combined with a CG-rich 5'-end turns out to minimize non-specific cleavage of the dyes by EndoV. DNA sequences of these primers are listed in Table 3. Wild-type and mutant genomic DNA were each subjected to a 50-μl "universal" PCR. The "universal" PCR reaction mixture contained 20 mM Tricine pH 8.7, 16 mM $(NH_4)_2SO_4$, 2.5 mM $MgCl_2$, 250 μM of each dNTP, 0.2 μM of the universal primer pair, 0.02 μM of the gene-specific primer pair, 5 units of AmpliTaq Gold (Applied Biosystems, Foster City, Calif.), and 150 ng genomic DNA. Thermo-cycle conditions of the "universal" PCR were as follows: 95° C. for 10 min, 20 cycles of 94° C. for 30 s, 65° C. for 1 min, 72° C. for 1 min (gene-specific amplification), 30 cycles of 94° C. for 30 s, 55° C. for 1 min, 72° C. for 1 min (universal amplification), followed by a final extension step at 72° C. for 7 min. The two fluorescent groups Vic and Ned appear green and yellow, respectively, when visualized on the ABI 3730 fluorescence-based DNA analyzer. Differential labeling of the top and bottom strands allows to distinguish cleavage products from each strand independently.

Example 8

PCR Amplification with Universal Primers: One 5'-End (Vic or Ned) Fluorescently Labeled Primer and one 5'-Phosphorylated Primer Genomic DNA was extracted from cell lines containing mutations in exon 1 of K-ras gene (codon 12) or exon 8 of p53 gene (codon 273). HT-29 cell line contains the wild-type K-ras gene, while SW480 and SW620 contain pure G12V (G->T) mutation. LoVo cell line contains wild-type p53 gene, while HT-29 SW480 and SW620 cell lines contain the R273H (G->A) mutation.

For K-ras exon 1 amplification, both wild-type and mutant (G12V, G->T) genomic DNA were subjected in parallel to 2 "universal" PCR amplifications, each of which used 2 primer pairs:

The 1$^{st}$ "universal" PCR used: 1—forward and reverse universal primers VicUniEV5F and p-UniEV6R, the former fluorescently-labeled with Vic on its 5'-end, the latter 5'-phosphorylated; 2-forward and reverse unlabeled gene-specific primers, F161 and R162, which harbor universal tails that are just 3-bp shorter than the universal primer sequence.

The 2$^{nd}$ "universal" PCR used: 1—forward and reverse universal primers p-UniEV5F and NedUniEV6R, the former 5'-phosphorylated, the latter fluorescently-labeled with Ned on its 5'-end; 2—forward and reverse unlabeled gene-specific primers, F161 and R162.

DNA sequences of these primers are listed in Table 3. Universal primers VicUniEV5F and NedUniEV6R have a reversed linkage label, i.e. 3'-[fluorescent group]]-5'-[universal primer sequence]-3'. The "universal" PCR conditions were identical to those described in Example 7.

Similar to K-ras PCR amplification, p53 exon 8 was amplified in 2 separate "universal" PCR, each of which used 2 primer pairs:

The 1$^{st}$ "universal" PCR used: 1—forward and reverse universal primers VicUniEV5F and p-UniEV6R; 2—forward and reverse unlabeled gene-specific primers, F173 and R174, which harbor universal tails that are just 3-bp shorter than the universal primer sequence, The 2$^{nd}$ "universal" PCR used: 1—forward and reverse universal primers p-UniEV5F and NedUniEV6R; 2—forward and reverse unlabeled gene-specific primers, F173 and R174.

Alternatively, p53 exon 8 was amplified in 2 other separate "universal" PCR:
   The $1^{st}$ one using forward and reverse universal primers VicUniEV1F and p-UniEV2R, and forward and reverse primers F173 and R174
   The $2^{nd}$ one using forward and reverse universal primers p-UniEV1F and NedUniEV2R, and forward and reverse primers F173 and R174.

VicUniEV1F and NedUniEV2R are internally labeled with the fluorescent group—Vic or Ned—attached to the C6 of the fourth base (Cytosine 4). Internal labeling combined with a CG-rich 5'-end turns out to minimize non-specific cleavage of the dyes by EndoV. DNA sequences of these primers are listed in Table 3. Wild-type and mutant genomic DNA were each subjected in a 50-µl mixture to "universal" PCR. The "universal" PCR conditions were identical to those described in Example 7.

Primers were phosphorylated on the 5'-end prior to PCR amplification by incubating 200 pmol of each primer (namely, p-UniEV5F, p-UniEV6R, p-UniEV1F, or p-UniEV2R) with 10 units of T4 polynucleotide kinase (New England Biolabs, Beverly, Mass.) for 1 h at 37° C. in a 25 µl-reaction volume containing 1× T4 polynucleotide kinase buffer (70 mM Tris-HCl pH 7.6, 10 mM $MgCl_2$, and 5 mM DTT) and 1 mM ATP. The enzyme was then heat inactivated for 20 min at 65° C., and small aliquots of the phosphorylation reaction were stored at −20° C. The two fluorescent groups Vic and Ned appear green and yellow, respectively, when visualized on the ABI 3730 fluorescence-based DNA analyzer. Differential labeling of the top and bottom strands is used to distinguish cleavage products from each strand independently.

Example 9

Performing EndoV/Ligase Mutation Scanning Assay Under the Standard Conditions—Analysis on the ABI 3730 DNA Analyzer The EndoV/Ligase assay was performed under the standard two-step reaction conditions: the EndoV cleavage reaction, followed by the ligase reaction (+EndoV, +Ligase reactions), as described below:
   1—Half the volume (~6.5 µl) of each PCR mixture, including the wild-type control, was incubated for 40 min at 65° C. in a 20-µl reaction mixture containing 20 mM Hepes pH 7.5, 5 mM $MgCl_2$, 1 mM DTT, 2% glycerol, 5% DMSO, 1.5 M betaine and 1 µM EndoV.
   2—Fifteen µl of each EndoV cleavage reaction mixture was then subjected to the Ligase reaction in a 20-µl final volume during a 30-min incubation at 65° C. This was done by adding 2 µl of 10× supplemental buffer (200 mM Tris pH 8.5, 12.5 mM $MgCl_2$, 500 mM KCl, 10 mM DTT, 200 µg/ml BSA), 1 µl of 20 mM NAD, and 2 µl of 30 DM Ligase.

In parallel, each PCR mixture, including the wild-type control, was subjected to the same protocol, except that both EndoV and ligase were replaced by water (-EndoV, -ligase control reactions). Finally, the reaction was terminated by addition of EDTA to a final concentration of 10 mM. This inhibited any further EndoV cleavage activity in the capillary. One-µl aliquots of the reaction mixtures were denatured at 95° C. for 2 minutes in 9 µl Hi-Di formamide along with 0.4 µl GeneScan-500 LIZ Size Standard (essential for sizing electrophoresed DNA fragments in the 35-500 bp range), and run on the ABI 3730 fluorescence-based capillary electrophoresis instrument (Applied Biosystems, Foster City, Calif.). The electrophoresis was carried out for 1200 seconds at 15 kV in POP-7 polymer at 60° C. At completion of the electrophoretic run, a virtual gel image was displayed with ABI collection software, v1.0, with Vic- and Ned-labeled fragments appearing in green and yellow, respectively, while LIZ-labeled Size Standard fragments were in the orange color. Data analysis was achieved using Gene Mapper fragment analysis software v3.0 (Applied Biosystems, Foster City, Calif.). Ultimately, realigning and rearranging the order of lanes on the virtual gel image was performed with Gel Render software, which was developed in our laboratory.

Example 10

Preparation of Pure Vic-/Ned-Labeled Heteroduplex DNA Substrates Using the "Split Label, Denaturation/Renaturation" Procedure PCR amplifications of p53 exon 8 were carried out according to the "universal" PCR strategy, using 2 primer pairs, as described in both Examples 7 and 8. Aliquots (4 µl) of the p53 exon 8 PCR products were analyzed on a 2% agarose gel, and quantified using the Gel-Doc 2000 imager with Quantity One software (BioRad, Hercules, Calif.). Approximately equal yields of the Vic-labeled wild-type p53 exon 8 PCR products were mixed with the Ned-labeled mutant p53 exon 8 (R273H G->A) PCR products in a 12 µl final volume, with a total of ~1500 ng DNA (PCR mixture 1). Likewise, the Vic-labeled mutant p53 exon 8 PCR products were mixed with the Ned-labeled wild-type p53 exon 8 PCR products in another 12-µl reaction (PCR mixture 2). The wild-type control consisted of a mixture of Vic-labeled wild-type p53 exon 8 PCR products with Ned-labeled wild-type p53 exon 8 PCR products in a 12 µl final volume (~1500 ng total DNA). In order to inactivate Taq DNA polymerase, 1 µl of proteinase K (20 mg/ml, Qiagen) was added to each PCR mixture, including the wild-type control, and incubated at 65° C. for 30 min. This was followed by a 10-min incubation at 80° C. to inactivate the proteinase K. PCR mixtures were then heated at 95° C. for 2 min, and gradually cooled down to room temperature in a GeneAmp PCR System 960 thermo-cycling machine (Perkin-Elmer) using the following PCR program: 95° C. for 2 min, 95° C. for 15 s, followed by a 0.2° C. decrease in temperature every 15 s down to 45° C., and finally by 10 min at 25° C. Thus, denaturation/reannealing of the [wild-type+mutant] p53 exon 8 PCR mixtures was used to generate two complementary labeled strands that anneal to form 100% of heteroduplex DNA fragments: PCR mixture 1 contains heteroduplexes with a G/T mismatch, while PCR mixture 2 contains heteroduplexes with an A/C mismatch. Wild-type control leads to the formation of 100% of G:C homoduplexes. This step was followed by the EndoV/Ligase reaction. The steps in this example are illustrated in FIG. 5.

Example 11

Lambda Exonuclease Procedure on p53 Exon 8 and K-ras Exon 1 PCR Fragments as Substrates Using the PCR Universal Strategy PCR amplifications of K-ras exon 1 and p53 exon 8 were carried out according to the "universal" PCR strategy, using 2 primer pairs, as described in both Examples 7 and 8. Briefly, K-ras exon 1 and p53 exon 8 were PCR amplified with Vic- and Ned-labeled universal primers, using the universal strategy described in details in Example 7. The two fragments are about 300 and 350 bp, respectively. Then, for each gene, wild-type and mutant PCR products were mixed to allow formation of heteroduplex DNA substrates using the standard procedure, as described in Example 2, and illustrated in FIG. 4. In parallel, K-ras exon 1 and p53 exon 8 were PCR amplified with a fluorescent universal primer and a 5'-phosphorylated one (and vice-versa), as described in Example 8. Wild-type and mutant PCR products were then mixed to allow formation of heteroduplex DNA substrates using the lambda exonuclease procedure, as described in Example 5. The EndoV/Ligase reactions were performed as described in Example 9 and illustrated in FIG. 6.

Figure 15:
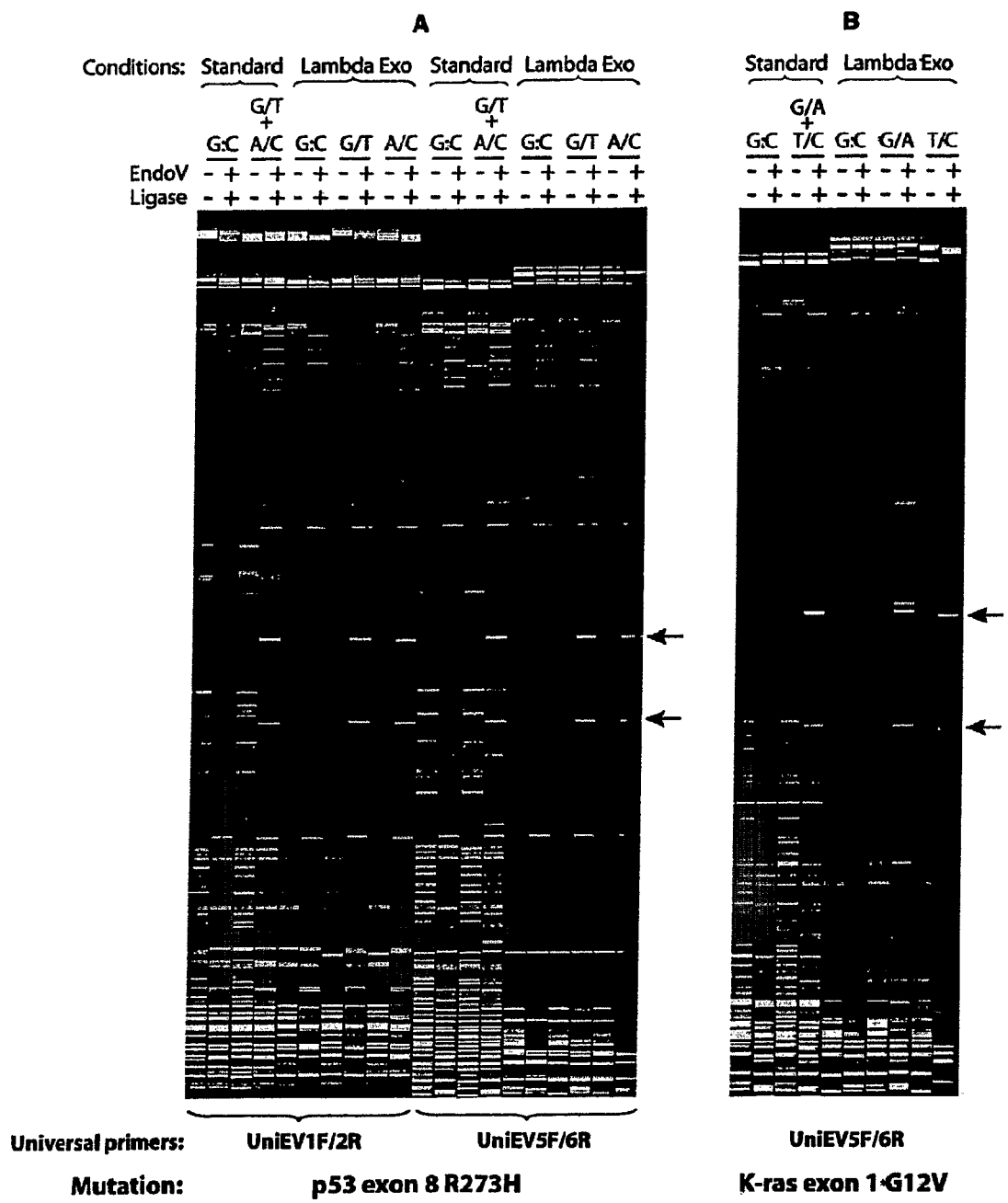
FIGS. 15A and B are electrophoretograms of EndoV/Ligase cleavage products obtained on heteroduplexed DNA containing the p53 exon 8 R273H mutation and the K-ras G12V mutation. Vic- and Ned-labeled universal primers were used in conjunction with gene-specific primers to amplify both wild-type and mutant p53 exon 8 and K-ras exon 1 fragments, respectively, for generating heteroduplexes using denaturation/renaturation. A phosphorylated universal primer and either Vic- or Ned-labeled universal primers were used in conjunction with gene-specific primers to amplify both wild-type and mutant p53 exon 8 and K-ras exon 1 fragments, respectively, when using lambda exonuclease to generate single strands, where complementary single strands reanneal to generate heteroduplexes. Standard heat denaturation/renaturation and lambda exonuclease procedures were performed in parallel to generate both heteroduplexed and (control) homoduplexed DNA substrates. Each PCR mixture was either treated with EndoV/Ligase (EndoV (+) and Ligase (+)), or untreated (EndoV (−) and Ligase (−)), as a negative control.
In FIG. 15B, the results obtained on K-ras exon 1 G12V mutation are displayed, when using VicUniEV5F and NedUniEV6R PCR primers. For the lambda exonuclease experiment, one of the labeled universal primers was replaced with a phosphorylated primer to allow for digestion of that strand. Under the standard denaturation/renaturation conditions, wild-type/mutant PCR mixtures contain heteroduplexes with G/A+T/C mismatches. Wild-type PCR fragments were used as controls (G:C match). With the lambda exonuclease procedure, two distinct types of wild-type/mutant PCR mixtures were subjected to the EndoV reaction: heteroduplexes of top strand wild-type with bottom strand mutant (G/A mismatch) and heteroduplexes of top strand mutant with bottom strand wild-type (T/C mismatch). Wild-type PCR mixtures were used as controls (G:C match). Reaction mixtures were electrophoresed on the ABI 3730 fluorescence-based capillary electrophoresis instrument (Applied Biosystems, Foster City, Calif.). At completion of the electrophoretic run, a virtual gel image was displayed on the instrument monitor, with Vic- and Ned-labeled fragments appearing in green and yellow, respectively. Data analysis was achieved using Gene Mapper fragment analysis software.

FIG. 15A represents the gel image obtained from the p53 exon 8 data, when using the 2 different sets of universal primers. FIG. 15B displays the K-ras exon 1 gel image when using primer set UniEV5F/EV6R. Top and bottom strand cleavage products are indicated with green and blue arrows, respectively. As in previous figures, wild-type G:C match, as well as G/T and A/C mismatches (from wild-type+mutant mixtures) are marked on top of the lanes for p53 exon 8 (R273H, G->A); wild-type G:C match. G/A and T/C mismatches (from wild-type+mutant mixtures) are marked on top of the lanes for K-ras exon 1 (G12V, G->T). As observed on the p53 and K-ras gel images, background cleavage is dramatically reduced in the Lambda Exonuclease conditions as compared to the standard conditions, independent of whether the UniEV1F/EV2R or the UniEV5F/EV6R primer set is used.

Example 12

Lambda Exonuclease Procedure Applied to p53 Exon 8 and p53 Exons 8-9 Fragments Amplified by the PCR Universal Strategy p53 exon 8 was amplified according to the "universal" PCR strategy, using 2 primer pairs, as described in Example 7: 1—forward and reverse universal primers VicUniEV5F and NedUniEV6R; 2—forward and reverse unlabeled gene-specific primers, F173 and R174. Then, heteroduplex DNA substrates were prepared using the standard denaturation/renaturation procedure as described in Example 2.

In parallel, p53 exon 8 was amplified in 2 separate "universal" PCR, each of which used 2 primer pairs, as described in Example 8:
 The 1$^{st}$ "universal" PCR used: 1—forward and reverse universal primers VicUniEV5F and p-UniEV6R; 2—forward and reverse unlabeled gene-specific primers, F173 and R174, which harbor universal tails that are just 3-bp shorter than the universal primer sequence.
 The 2$^{nd}$ "universal" PCR used: 1—forward and reverse universal primers p-UniEV5F and NedUniEV6R; 2—forward and reverse unlabeled gene-specific primers, F173 and R174.

Heteroduplex DNA substrates were prepared using the lambda exonuclease procedure as described in Example 5 and illustrated in FIG. 6. Alternatively, heteroduplex DNA fragments were prepared following the "split label, denaturation/renaturation" procedure described in Example 10 and illustrated in FIG. 5.

Similar to p53 exon 8 amplification, a fragment encompassing p53 exons 8-9 was PCR amplified, using a new set of gene-specific primers: p53ex8F and p53ex9R (Table 3), which generated a 591-bp PCR fragment containing the R273H mutation. Preparation of heteroduplex Dna substrates was carried out using both the standard and the lambda exonuclease procedure. The EndoV/Ligase assay was performed under the standard conditions described in Example 9

Figure 16:
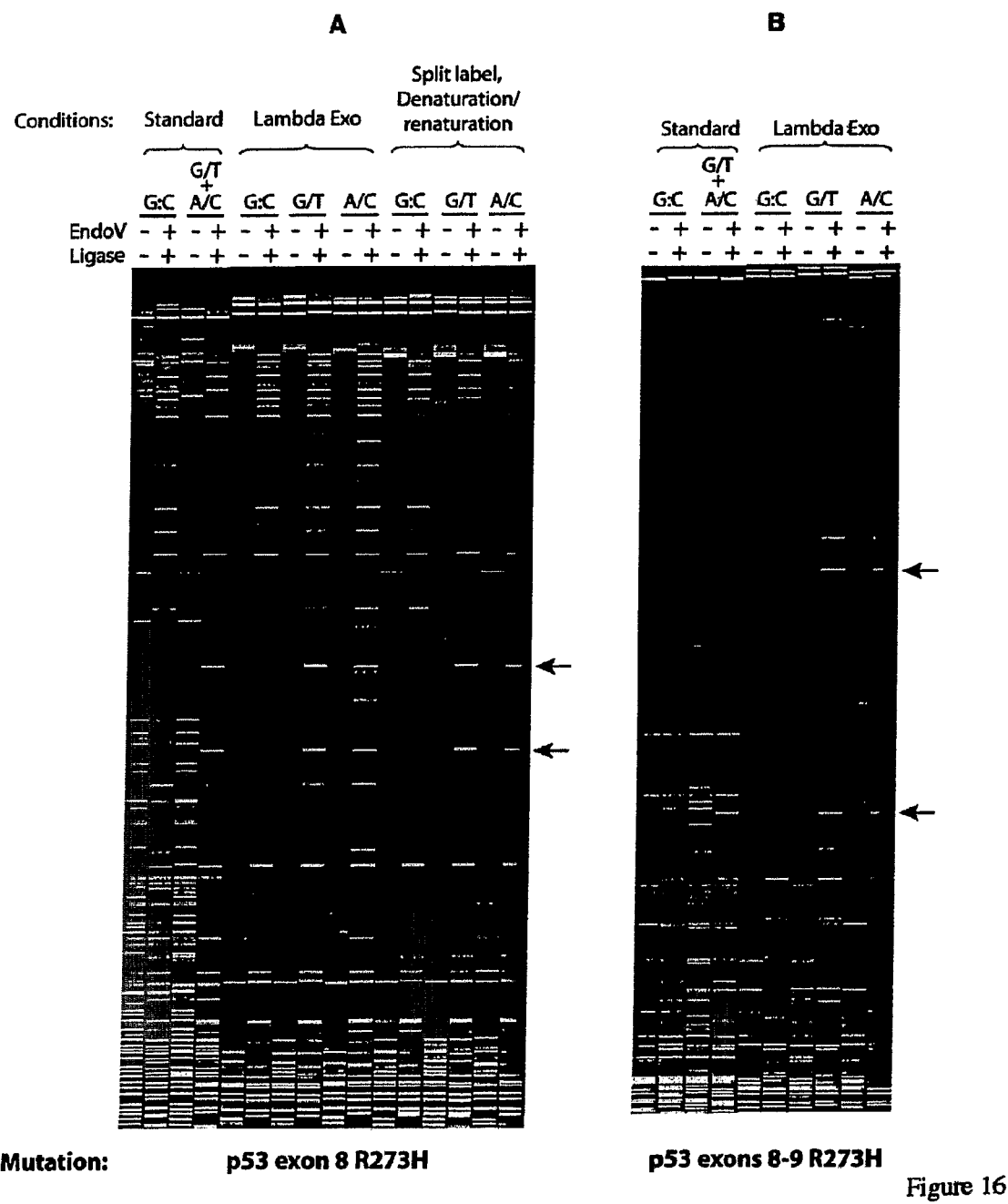
FIG. 16 shows a comparison of different heteroduplexing methods when using Universal PCR primers (VicUniEV5F/NedUniEV6R), and p53 exon 8 and exons 8-9 fragments (R273H mutation) as substrates: a standard denaturation/reannealing method (see FIG. 4), a lambda exonuclease procedure (see FIG. 6), and a "split label, denaturation/renaturation" procedure (see FIG. 5). Each PCR mixture was either treated with EndoV/ligase (EndoV (+) and Ligase (+)), or untreated (EndoV (−) and Ligase (−)), as a negative control.

Results are illustrated in FIG. 16. Top and bottom strand cleavage products are indicated with green and blue arrows, respectively. Wild-type G:C matched bases, as well as G/T and A/C mismatches (i.e. the [wild-type+mutant] mixtures) are marked on top of the lanes. As observed FIG. 16A, background noise was significantly attenuated under the lambda exonuclease conditions as compared to the standard conditions. Furthermore, for both G/T and A/C mismatches, top and bottom strand cleavage products were detected in the lambda exonuclease procedure, while only the top strand cleavage product was visible under the standard conditions. These data show once again that the lambda exonuclease procedure is more effective than the standard one in mutation detection by EndoV/Ligase mutation scanning assay. In FIG. 16B, three different methods for preparing p53 exon 8 PCR (R273H) heteroduplexed fragments are compared: (i) the standard procedure, (ii) the lambda exonuclease procedure, and (iii) the "split label denaturation/renaturation" procedure. Surprisingly, the data revealed that the "split label, denaturation/renaturation" procedure did not lead to higher background cleavage than the lambda exonuclease procedure. This suggested that the reduction of nonspecific cleavage in the lambda exonuclease procedure was mainly due to the use of half as many fluorescently labeled molecules as in the standard method. Likewise, the advantage of the alternate "Denaturation/renaturation" procedure is that only one labeled heteroduplex is formed at a time. Finally, when PCR amplifying fragments using both Vic and Ned labeled primers simultaneously in the same reaction (as is done with the standard procedure), a higher number of background fragments are observed in the PCR product lanes, and these add to the overall background observed after EndoV cleavage, even though they are unrelated to the EndoV cleavage step (first 4 lanes of both FIG. 16A and FIG. 16B).

Example 13

Test of Additives Tetramethylene Sulfoxide and Tetramethylene Sulfone as Organic Solvents to Enhance the EndoV Cleavage Reaction Genomic DNA from the cell line SW620 containing homozygous p53 exon 8 mutation R273H was used as the mutant templates. Genomic DNA from the cell line Lovo containing wild-type DNA in p53 exon 8 was used as wild-type DNA control. PCR primers were labeled with ((3',6'-dippivaloylFuoresceinyl)-6-carbox-amidohexyl)-1-O-(2-cyanoethyl)-(N,N-diisopropyl)-phosphor-amidite (6-Fam) or 4,7, 2',7'-tetrachloro-(3',6'-dippivaloyl-uoresceinyl)-6-carboxamidohexyl-1-O— (2-cyanoethyl)-(N,N-diisopropyl)-phosphoramidite (Tet).

The primer sequences are as followed:

```
p53 exon8 forward sequence:
                                    (SEQ ID NO: 21)
TET-5'-TETCCCGGACAGGTAGGACCTGATTTCCTTAC-3' p53 exon8 reverse sequence:
                                    (SEQ ID NO: 22)
6 FAM-5'-CCCCGCTTCTTGTCCTGCTTGCTTAC-3'
```

PCR reaction was carried out in a 50 µl of mixture containing 10 mM Tris-HCl, pH 8.3, 50 mM KCl, 2.5 mM MgCl$_2$, 0.25 mM dNTP, 10 pmol of each primer, 150 ng of wild type genomic DNA, 5 U AmpliTaq DNA polymerase. The PCR program is as follows: 95° C. for 1 min, then 5 U of AmpliTaq DNA polymerase was added, followed by 35 cycles of 94° C.

for 20 sec., 68° C. for 30 sec. and 72° C. for 1 minute, then followed by final extension of at 72° C. for 7 minutes.

Control homoduplex DNA was generated by denaturing and reannealing wild-type PCR products. Heteroduplex DNA was generated by denaturing and reannealing a mixture of 50% wild-type PCR products and 50% mutant PCR products. The mixtures were incubated in a PCR machine with a PCR program of 95° C. for 2 min to denature the DNA, followed by gradual cooling from 95° C. to 45° C. for one hour to reanneal the strands. The steps in this procedure are illustrated in FIG. 3.

Figure 18:
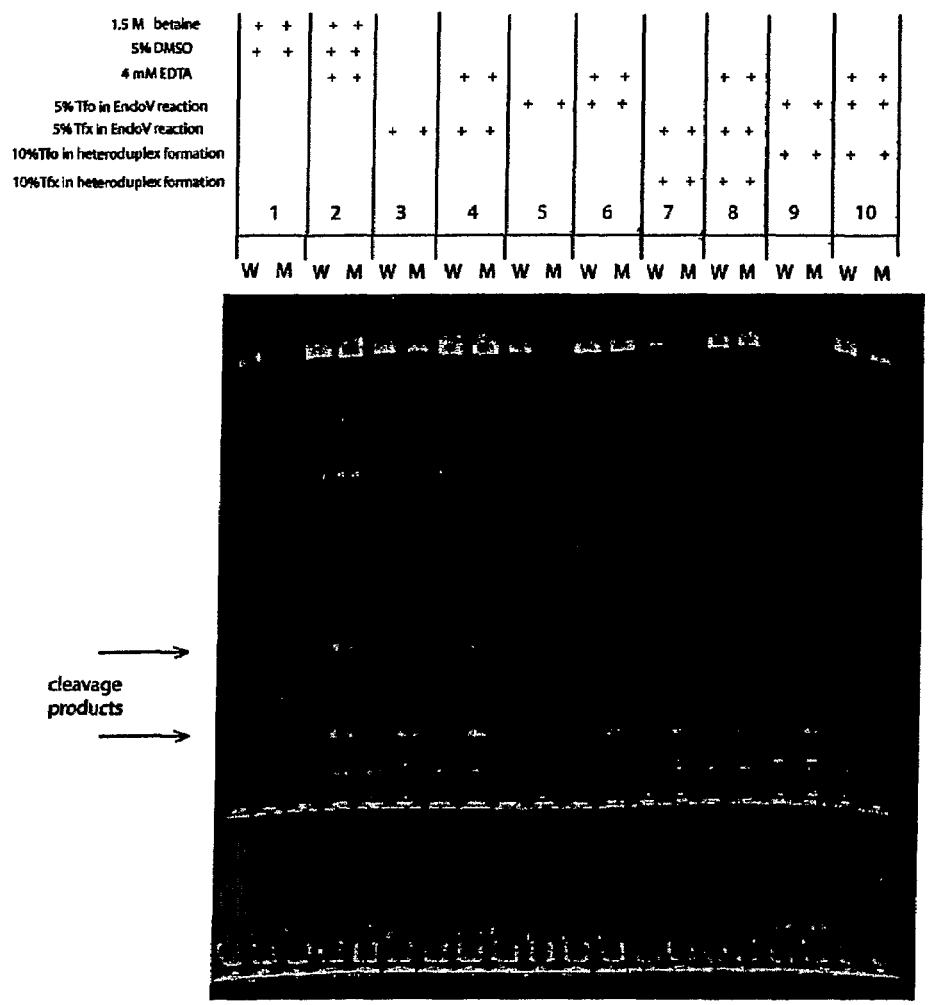
FIG. 18 is an electrophoretogram of EndoV cleavage products of heteroduplexed DNA containing the p53 R73H mutation in the presence of tetramethylene sulfone or tetramethylene sulfoxide. Symbols: W is the PCR fragment amplified from DNA template containing wild-type p53 gene exon 8; M is the mixture of 50% wild-type p53 exon 8 PCR fragments and 50% PCR fragments amplified from DNA template containing the R273H mutation in exon 8. Under "standard conditions," the mixtures were denatured at 95° C. for 2 min, followed by gradually reducing the temperature from 95° C. to 45° C. for one hour to allow for reannealing. EndoV reaction was carried out in a 20 µl of mixture containing 10 mM Hepes pH 7.5, 5 mM $MgCl_2$, 7 µl of duplex DNA, 1 µM EndoV, and chemical additives at 65° C. for 40 min. The standard additives are 5% DMSO and 1.5 M betaine.

The EndoV reaction was carried out in a 20 µl reaction mixture containing 10 mM Hepes pH 7.5, 5 mM $MgCl_2$, 7 µl of duplex DNA, 1 µM EndoV, chemical additives at 65° C. for 40 min. The standard additives are 5% DMSO and 1.5 M betaine. In FIG. 18, conditions 3, 4, 7, and 8, 5% tetramethylene sulfoxide was added to replace DMSO and betaine in the EndoV reaction buffer. In conditions 5, 6, 9, and 10, 5% tetramethylene sulfone was added to replace DMSO and betaine in the PCR reaction mixture. In conditions 7 and 8, 10% tetramethylene sulfoxide was added in the mixture of heteroduplex formation, while in conditions 9 and 10, 10% tetramethylene sulfone was added in the mixture prior to forming heteroduplexes. The ligation step was omitted in this experiment. The reaction conditions are as follows:

Condition 1: Standard conditions for generating heteroduplexes (95° C., 2 min., slow cool to 45° C. over 1 hour) and EndoV reactions (5% DMSO and 1.5 M betaine).

Condition 2: 4 mM EDTA (final concentration) was added during the heteroduplex formation incubation step.

Condition 3: 5% tetramethylene sulfoxide was added during the EndoV cleavage step.

Condition 4: 4 mM EDTA was added during the heteroduplex formation incubation step. 5% tetramethylene sulfoxide was added during the Endo cleavage step.

Condition 5: 5% tetramethylene sulfone was added during the EndoV cleavage step.

Condition 6: 4 mM EDTA was added during the heteroduplex formation incubation step, 5% tetramethylene sulfone was added during the EndoV cleavage step.

Condition 7: 10% tetramethylene sulfoxide was added during the heteroduplex formation incubation step. 5% tetramethylene sulfoxide was present during the EndoV cleavage step.

Condition 8: 10% tetramethylene sulfoxide and 4 mM EDTA were added during the heteroduplex formation incubation step. Final concentration of 5% tetramethylene sulfoxide was present in the EndoV reaction mixture.

Condition 9: 10% tetramethylene sulfone was added during the heteroduplex formation incubation step. Final concentration of 5% tetramethylene sulfone was present during the EndoV cleavage step.

Condition 10: 10% tetramethylene sulfone and 4 mM EDTA were added during the heteroduplex formation incubation step. Final concentration of 5% tetramethylene sulfone was present during the EndoV cleavage step.

The EndoV reaction was terminated by adding equal volumes of GeneScan stop solution (50 mM EDTA, 1% blue dextran and 80% formamide). After denaturing at 94° C. for 1 min, 3 ml of the mixtures were loaded onto a 6% acrylamide/bisacrylamide (19:1) and 0.2 mm thick denaturing gel containing 6M urea and electrophoresed for 1 h at 1000 V in TBE buffer (90 mM Tris-Borate, pH 8.3, 2 mM EDTA) at 45° C. in an ABI-377 sequencer. Results were analyzed using the Genescan analysis program (Applied Biosystems).

From the gel image (see FIG. 18), for the even numbered conditions, i.e. 2, 4, 6, 8, and 10, 4 mM EDTA was present in the mixture during the heteroduplex formation incubation step. The amount of cleavage products observed in the even numbered conditions is always higher than their corresponding yields in the odd numbered conditions (in which EDTA is absent). This result suggests that adding 4 mM EDTA during heteroduplex formation enhances the intensity of mutation signals.

The electrophoretogram result also show that adding 5% tetramethylene sulfoxide, or tetramethylene sulfone in the EndoV reaction mixture without betaine and DMSO gives reasonable signals compared with the standard condition with betaine and DMSO (FIG. 18, conditions 3-6). Adding 10% tetramethylene sulfoxide, or tetramethylene sulfone in the mixture of heteroduplex formation, and 2% tetramethylene sulfoxide, or tetramethylene sulfone in EndoV reaction mixture also generates reasonable mutation signals (FIG. 18, conditions 8-10). Consequently, 5% tetramethylene sulfoxide, or tetramethylene sulfone can be used as an additive to replace 1.5M betaine and 5% DMSO in the EndoV reaction.

Example 14

Test of Different 5' Modified Primers to Evaluate Resistance to EndoV Cleavage

Genomic DNA from cell line SW620 containing homozygous p53 exon 8 mutation R273H was used as mutant templates. Genomic DNA isolated from the LoVo cell line contains wild-type DNA of p53 exon 8 and was used as the wild-type DNA control template. Internally-labeled primers for p53 exon 8 were synthesized by ABI (Applied Biosystems, Foster, Calif.). The sequences of each primer are listed in Table 5.

Fluorescent group 6-Fam is (3',6'-dippivaloylfuorescéinyl)-6-carbox-amidohexyl)-1-O-(2-cyanoethyl)-(N,N-di-isopropyl)-phosphor-amidite. Vic and Ned are dyes developed by ABI (Applied Biosystems, Foster City, Calif.).

The modified primers were used to amplify p53 exon 8 from wild type cell line genomic DNA and from cell line genomic DNA containing pure p53 exon 8 R273H.

Each set of PCR reactions was carried out separately on wild-type DNA and DNA containing the R273H mutation.

The 1st set of PCR reactions were carried out in a 50 µl of reaction mixture containing 20 mM Tricine pH 8.7, 16 mM $(NH_4)_2SO_4$, 2.5 mM $MgCl_2$, 0.25 mM dNTP, 10 pmol VICp53Ex8-F72 and NED p53Ex8—R74, 100 ng genomic DNA from Lovo cell line or SW620, 5 U AmpliTaq DNA polymerase. The mixture was incubated in a PCR machine at 95° C. for 2 min, then AmpliTaq DNA polymerase was added. The PCR program is 35 cycles of 94° C. for 20 second, 68° C. for 30 second and 72° C. for 1 minute followed by final extension at 72° C. for 7 minutes.

The 2nd set PCR reactions were carried out in the same mixture and conditions except that 10 pmol primer Vic p53Ex8-F76 and Ned p53Ex8—R78 were used.

The 3rd PCR reaction was carried out in the same mixture and conditions except that 10 pmol primers Vic p53Ex8-F92 and Ned p53Ex8—R94 were used.

TABLE 4

Different modifications on primers of p53 exon 8.

| Primer name | Primer Sequences | |
|---|---|---|
| VIC p53Ex8-F72 | 5' VIC-(2'OMeC)(2'OMeC)CGCCGCAGGGTGGTTGGGAGTAGATG-3' | (SEQ ID NO: 23) |
| NED p53Ex8-R74 | 5'NED(2'OMeC)(2'OMeC)CGCCGCGGTGATAAAAGTGAATCTGAGGCATAAC-3' | (SEQ ID NO: 24) |
| VIC p53Ex8-F76 | 5' VIC-CGCCGCAGGGTGGTTGGGAGTAGATG-3' | (SEQ ID NO: 25) |
| NED p53Ex8-R78 | 5' NED-CGCCGCGGTGATAAAAGTGAATCTGAGGCATAAC-3' | (SEQ ID NO: 26) |
| VIC p53Ex8-F92 | 5' CCGC(C-c6-VIC)GCAGGGTGGTTGGGAGTAGATG-3' | (SEQ ID NO: 27) |
| NED p53Ex8-R94 | 5' CCGC(C-c6-NED)GCGGTGATAAAAGTGAATCTGAGGCATAAC-3' | (SEQ ID NO: 28) |

1 µl of Proteinase K (20 mg/ml) (QIAGEN, Valencia, Calif.) was added into every 12 µl of PCR products at 65° C. for 30 min to inactivate AmpliTaq DNA polymerase. Proteinase K was inactivated by incubating at 85° C. for 15 min.

Homoduplex DNA control was generated by denaturing and reannealing wild-type PCR products alone. Heteroduplex DNA was generated by denaturing and reannnealing the mixture containing 50% wild-type PCR products and 50% PCR products containing homozygous p53 R273H mutation. The mixtures were denatured at 95° C. for 2 min, followed by gradually reducing the temperature from 95° C. to 45° C. for one hour to allow for reannealing. The steps of this example are illustrated in FIG. 3.

The EndoV mutation assay was carried out in a 20 µl of mixture containing 10 mM Hepes (pH 7.5), 5 mM $MgCl_2$, 5% DMSO, 1.5 M betaine, 1 µM EndoV and 7 µl of homoduplex or heteroduplex PCR products at 65° C. for 40 min. The reaction was terminated by adding 0.1 volume (2 µl) of 100 mM EDTA. One µl of cleavage products was mixed with 8.5 µl of Hi-Di formamide (Applied Biosystems, Foster City, Calif.) and 0.5 µl of LIZ labeled GeneScan-500 LIZ size standard (Applied Biosystems, Foster City, Calif.). After denaturing at 95° C. for 2 min and cooling down on ice, the mixture was loaded on a ABI 3730 DNA sequencer for electrophoresis in polymer POP7 under 15 kV voltage, 1200 sec running time, 60° C. oven temperature. The gel image was visualized with ABI collection software.

There are two sets of experiments. In one set of experiment, the EndoV reaction was terminated by adding 0.1 volume (2 µl) 100 mM EDTA, in the other set, the reaction was not terminated. On the capillary electrophoresis image, each sample has three lanes. The first lane is the electrophoresis result of PCR products without addition of EndoV. The second lane is EndoV cleavage products without EDTA termination, and the third lane is the EndoV cleavage products with EDTA termination (see FIG. 19). The results indicate that for the primers with EndoV resistant sequence, and resistant sequence plus 2'O methylated C, the fluorescent intensity of the PCR substrate without EDTA termination is much weaker than that with EDTA termination (see FIGS. 19A and B). On the other hand, for the primer with internal labeling, the fluorescence intensity of the PCR substrates without EDTA termination is almost the same as that with EDTA termination (FIG. 19C).

The results indicate that primers containing a 5' "resistant sequence, CGCCGC" or 2-'O methyl-C backbone (see FIGS. 19A and B) were still being cleaved by EndoV. It is noteworthy that the intensity of substrates in the absence of EDTA termination of the EndoV reaction is much weaker than the intensity with EDTA terminations (in FIGS. 19A and B, compare 3rd lane with 2nd lane). For internally-labeled primers (in FIG. 19C, compare 2nd lane and 3rd lane), the overall intensities of signals are almost the same in the absence of the EDTA termination as in the presence of the EDTA termination. This demonstrates that primers with internal labels are resistant to cleavage by EndoV (See FIG. 19C).

Example 15

Comparison of EndoV Cleavage Products with Internally-Labeled Universal Primers and the Universal Primer in which the Linkage Between the Vic or Ned Label and the 5' end of Primer is Reversed, i.e. 3'-Vic-5'-5'-primer-3'.

This experiment is designed to demonstrate universal primer labeling of PCR fragments and compare resistance to cleavage between internally labeled primers and reversed labeled primers.

The universal primers are listed in Table 3. Vic-UniEV1F and Ned-UniEV2R are internally-labeled universal primers. Vic-UniEV5F and Ned-UniEV6R are universal primers in which the base of Vic and Ned and the 5' end of primer is 3' to 5' reversed. The gene-specific primers for p53 exon 6 are listed as F167 and R168, and listed in Table 3.

For PCR reaction with internally-labeled universal primers, DNA fragments of p53 exon 6 were amplified in a 50 µl reaction mixture containing 20 mM Tricine pH 8.7, 16 mM $(NH_4)_2SO_4$, 2.5 mM $MgCl_2$, 1 pmol F167 and R168, 10 pmol Vic-UniEV1F and Ned-UniEV2R, 5 U AmpliTaqGold DNA polymerase, 100-150 ng genomic DNA from clinical samples. The PCR program is as follows: 95° C. for 10 min, 20 cycles of 94° C. for 30 sec, 65° C. for 1 min, 72° C. for 1 min, followed by 30 cycles of 94° C. for 30 sec, 55° C. for 1 min, 72° C. for 1 min. The final extension is 72° C. for 7 min.

For PCR reaction with universal primers in which the base of Vic and Ned and the 5' end of primer is 3' to 5' reversed. DNA fragments of p53 exon 6 were amplified in a 50 µl of reaction mixture containing 20 mM Tricine pH 8.7, 16 mM $(NH_4)_2SO_4$, 2.5 mM $MgCl_2$, 1 pmol of primer F161 and R162, 10 pmol Vic-UniEV5F and Ned-UniEV6R, 5 U AmpliTaqGold DNA polymerase, 100-150 ng genomic DNA from clinical samples. The PCR program is as follows: 95° C. for 10 min, 20 cycles of 94° C. for 30 sec, 65° C. for 1 min, 72° C. for 1 min, followed by 30 cycles of 94° C. for 30 sec, 55° C. for 1 min, 72° C. for 1 min. The final extension is 72° C. for 7 min.

Homoduplex DNA control was generated by denaturing and re-annealing wild type PCR products alone. Heteroduplex DNA was generated by denaturing and reannealing the mixture containing 50% wild-type PCR products and 50% PCR products containing homozygous p53 Q192Ter or Y205F mutation. The mixtures were denatured at 95° C. for 2 min, followed by gradually reducing the temperature from 95° C. to 45° C. for one hour to allow for reannealing. The steps of this procedure are illustrated in FIG. 4.

The EndoV reactions on heteroduplex and homoduplex DNA substrates, with internally labeled primers or reversed linkage primers, were carried out under standard conditions. Since this experiment was designed to determine if mutation cleavage products could be distinguished even in a high background, the ligation step was omitted. EndoV reaction was carried out at 65° C. for 40 min in a 20 µl reaction mixture containing 10 mM Hepes pH 7.5, 5 mM $MgCl_2$, 5% DMSO, 1.5 M betaine, 7 µl of heteroduplex or homoduplex DNA and 1 µM EndoV. The reaction was terminated by adding 2 µl of 100 mM EDTA. One µl of cleavage products was mixed with 8.5 µl of Hi-Di formamide (Applied Biosystems, Foster City, Calif.) and 0.5 µl of LIZ labeled ABI GeneScan-500 LIZ size standard. The mixture was heated at 95° C. for 2 min and cooled down on ice and loaded in an ABI 3730 DNA sequencer for electrophoresis. The electrophoresis was performed with POP7 polymer under 15 kV voltage, 1200 sec running time, 60° C. oven temperature. The array image was displayed using the ABI collection software and analyzed with the GeneMapper software version 3.0 (Applied Biosystems, Foster City, Calif.).

In the gel image of EndoV reactions on PCR fragments generated by either set of universal primers (see FIGS. 20A and B), the cleavage products were easily visualized (indicated by arrows). Using internally-labeled primers, there are two high molecular weight artifacts that migrate at around 600 bp (see FIG. 20A). For the reversed linkage labeled primers, there were very low molecular weight cleavage products running near the bottom of the gel (see FIG. 20B). These products are not present in the gel image with internally-labeled primers, suggesting that EndoV can cleave the fluorescent group from the 5' end of the reversed linkage primer, but it cannot cleave the fluorescent group from the 5' end of the internally labeled primers. Nevertheless, both universal primer sets provide strong signal that is easily distinguished from background, even in the absence of a ligation-resealing step.

Example 16

Demonstration of Mutation Scanning of the K-Ras Exon1, p53 Exons 6, 7, and 8 with Internally Labeled Primers Cell line genomic DNA SW620 containing homozygous p53 exon 8 mutation R273H was used as mutant templates. Cell line genomic DNA Lovo containing wild-type DNA in p53 exon 8 was used as wild-type DNA control. Using internally-labeled primers as PCR primers, DNA from several clinical samples was PCR amplified in K-ras exon1, p53 exon 5, 6, 7 and 8. The PCR primer sequences are listed in Table 5.

TABLE 5

Sequence of internal labeled PCR primers.

| Amplified region | Direction | primer name | Primer sequences | |
|---|---|---|---|---|
| k-ras exon 1 | forward | VIC K-rasEx1-F102 | TCCGC (C-c6-VIC) | GCATAGTGTATTAACCTTATGTGTGACATGTTC (SEQ ID NO: 29) |
| | reverse | NED K-rasEx1-R104 | CTCGGC (C-c6-NED) | CGCAAAATGGTCAGAGAAACCTTTATCTGTATC (SEQ ID NO: 30) |
| p53 exon 5 | forward | VIC p53Ex5-F106 | TCCGC (C-c6-VIC) | GCTGTTCACTTGTGCCCTGACTTTC (SEQ ID NO: 29) |
| | reverse | NED p53Ex5-R108 | CTCGGC (Cc6-NED) | CGCCCAGCTGCTCACCATCGCTATC (SEQ ID NO: 30) |
| p53 exon 6 | forward | VIC p53Ex6-F110 | TCCGC (C-c6-VIC) | GCCTCTGATTCCTCACTGATTGCTCTTA (SEQ ID NO: 31) |
| | reverse | NED p53Ex6-R112 | CTCGGC (C-c6-NED) | CGGCCACTGACAACCACCCTTAAC (SEQ ID NO: 32) |
| p53 exon 7 | forward | VIC p53Ex7-F114 | TCCGC (C-c6-VIC) | GCTGGGCGACAGAGCGAGATTCCATC (SEQ ID NO: 33) |
| | reverse | NED p53Ex7-R116 | CTCGGC (C-c6-NED) | CGTGGATGGGTAGTAGTATGGAAGAAATC (SEQ ID NO: 34) |
| p53 exon 8 | forward | VIC p53Ex8-F118 | TCCGC (C-c6-VIC) | GCAGGGTGGTTGGGAGTAGATG (SEQ ID NO: 35) |
| | reverse | NED p53Ex8-R120 | CTCGGC (C-c6-NED) | CGGTGATAAAAGTGAATCTGAGGCATAAC (SEQ ID NO: 36) |

PCR reactions were carried out in a 50 µl reaction mixture containing 20 mM Tricine pH 8.7, 16 mM $(NH_4)_2SO_4$, 2.5 mM $MgCl_2$, 0.25 mM dNTP, 10 pmol of each primer, 150 ng of wild type genomic DNA or mutant DNA, 5 U AmpliTaq DNA polymerase.

For amplification of K-ras exon 1: The PCR mixture was the same as above except that the primers were 10 pmol Vic-K-ras Ex1-F102, and Ned-K-ras Ex1-R104. Genomic DNA from HT29 cell line was used as wild-type DNA. Genomic DNA from cell line SW620 containing G12V was used as mutant DNA. PCR conditions are as follows: 95° C. for 1 m, then 5 U of AmpliTaq DNA polymerase was added, followed by 35 cycles of 94° C. for 20 second, 65° C. for 30 second and 72° C. for 1 minute, then followed by final extension at 72° C. for 7 minutes.

For amplification of p53 exon 5: The PCR mixture was the same above except that the primers were 10 pmol Vic-p53Ex5-F106, and Ned-p53Ex5—R108. DNA from tumor samples containing the p53H179Y mutation was used as mutant DNA. DNA from normal tissue from the same patient was used as wild-type DNA. The PCR program is 95° C. for 1 minute, then 5 U of AmpliTaq DNA polymerase was added, followed by 35 cycles of 94° C. for 20 second, 68° C. for 30 second and 72° C. for 1 minute, then followed by final extension at 72° C. for 7 minutes.

For amplification of p53 exon 6: The PCR mixture was the same above except that the primers were 10 pmol Vic-p53Ex6-F110, and Ned-p53Ex6—R112. DNA from tumor samples containing Q192Ter and Y205F were used as mutant DNA. DNA from normal tissue from the same patient was used as wild-type DNA. The PCR program is 95° C. for 1 minute, then 5 U of AmpliTaq DNA polymerase was added, followed by 35 cycles of 94° C. for 20 second, 68° C. for 30 second and 72° C. for 1 minute, then followed by final extension of at 72° C. for 7 minutes.

For amplification of p53 exon 7: The PCR mixture was the same as above except that the primers were 10 pmol Vic-p53Ex7-F114, and Ned-p53Ex7—R116. DNA from tumor samples containing R248Q was used as mutant DNA. DNA from normal tissue from the same patient was used as wild-type DNA. The PCR program is 95° C. for 1 minute, then 5 U of AmpliTaq DNA polymerase was added, followed by 35 cycles of 94° C. for 20 second, 63° C. for 30 second and 72° C. for 1 minute, then followed by final extension at 72° C. for 7 minutes.

For amplification of p53 exon 8: The PCR mixture was the same as above except that the primers were 10 pmol Vic-p53Ex8-F118, and Ned-p53Ex8—R120. Genomic DNA from cell line SW620 containing R273H was used as mutant DNA. Genomic DNA from cell line LoVo was used as wild-type control. The PCR program is 95° C. for 1 minute, then 5 U of AmpliTaq DNA polymerase was added, followed by 35 cycles of 94° C. for 20 second, 68° C. for 30 second and 72° C. for 1 minute, then followed by final extension at 72° C. for 7 minutes.

1 μl of proteinase K (QIAGEN, 20 mg/ml) was added into 12 μl of PCR products to inactivate Taq DNA polymerase. The mixture was incubated at 65° C. for 30 min to inactivate Taq DNA polymerase and then 85° C. for 15 min to inactivate proteinase K.

Homoduplex DNA control was generated by denaturing and re-annealing wild-type PCR products alone. Heteroduplex DNA was generated by denaturing and reannnealing the mixture containing 50% wild-type PCR products and 50% PCR products containing homozygous p53 R273H mutation. The mixtures were denatured at 95° C. for 2 min, followed by gradually reducing the temperature from 95° C. to 45° C. for one hour to allow for reannealing. The steps of this example are illustrated in FIG. 3.

The EndoV reaction on heteroduplex and homoduplex DNA samples with internally-labeled primers or reverse linkage labeled primers were carried out under standard conditions. Since this experiment was designed to determine if mutation cleavage products could be distinguished even in a high background, the ligation step was omitted. EndoV reaction was carried out at 65° C. for 40 min in a 20 μl reaction mixture containing 10 mM Hepes pH 7.5, 5 mM MgCl$_2$, 5% DMSO, 1.5 M betaine, 7 μl of heteroduplex or homoduplex DNA and 1 μM EndoV. The reaction was terminated by adding 2 μl of 100 mM EDTA. 1 μl of cleavage products was mixed with 8.5 μl of Hi-Di formamide (Applied Biosystems, Foster City, Calif.) and 0.5 μl of LIZ-labeled ABI GeneScan-500 LIZ size standard. The mixture was heated at 95° C. for 2 min and cooled down on ice and loaded in an ABI 3730 DNA sequencer for electrophoresis. The electrophoresis was carried out with POP7 polymer under 15 kV voltage, 1200 sec running time, 60° C. oven temperature. The array image was shown in the ABI collection software and analyzed with the GeneMapper software version 3.0 (Applied Biosystems, Foster City, Calif.). Since ABI 3730 DNA sequencer is a capillary electrophoresis instrument. The EndoV cleavage products in the each capillary has its own unique mobility; there are some small mobility differences among all capillaries. The cleavage products of same molecular weight are not aligned with each other. A software program (called Gel Render) can automatically realign the gel image of cleavage products in each capillary, so that the cleavage product of the same molecular weight migrate at same position. This assists in identifying mutations visually on the capillary array image.

By comparing cleavage products from mutant DNA with wild-type DNA, it was shown that using internally-labeled primers, mutations of K-ras G12V, p53H179Y, Q192Ter, Y205F, R248Q and R273H in these samples can be significantly detected after electrophoresis of cleavage products in a 3730 DNA sequencer. (See FIG. 21).

Example 17

Optimization of Buffer Conditions of Mutation Detection by Tma EndoV/Ligase when Using Heteroduplex p53 Exon 8 PCR Fragments as Substrates Exon 8 of p53 has always generated high levels of background cleavage under the standard conditions. Therefore, this gene was used as a model system to test conditions that improve the signal-to-noise ratio of the EndoV/Ligase reaction. In these experiments, various Tricine buffer conditions, I through IV, were tested in the EndoV/Ligase reaction, each of them including sub-conditions (A through H), and compared to the standard EndoV cleavage conditions (i.e. Hepes pH 7.5 buffer).

p53 exon 8 was amplified in 2 separate "universal" PCR, each of which used 2 primer pairs, as described in Example 8:

The 1$^{st}$ "universal" PCR used: 1—forward and reverse universal primers VicUniEV1F and p-UniEV2R; 2—forward and reverse unlabeled gene-specific primers, F173 and R174, which harbor universal tails that are just 3-bp shorter than the universal primer sequence, The 2$^{nd}$ "universal" PCR used: 1—forward and reverse universal primers p-UniEV1F and NedUniEV2R; 2—forward and reverse unlabeled gene-specific primers, F173 and R174.

A 350-bp PCR fragment was amplified as described in Example 11. Heteroduplexed DNA substrates were prepared using the "split label, denaturation/renaturation" procedure described in Example 10 and illustrated in FIG. 5. As a reference, the EndoV/Ligase reaction was performed under the standard buffer conditions (two-step reaction), previously described in Example 9.

Condition I-E was carried out as follows:
1—Half the volume (~6.5 μl) of each PCR mixture, including the wild-type control, was incubated for 60 min at 65° C. in a 20-μl reaction containing 20 mM Tricine pH8, 5 mM MgCl$_2$, 1 mM DTT, 5% DMSO, 1.5 M betaine, 2% glycerol, and 1 μM EndoV.
2—Fifteen μl of each EndoV cleavage reaction were then subjected to the ligase reaction in a 20-μl final volume during a 60-min incubation at 65° C. This was done by adding 2 μl of 10× supplemental buffer (400 mM Tricine pH8, 12.5 mM MgCl$_2$, 100 mM DTT, 200 μg/ml BSA), 1 μl of 100 mM NAD, and 2 μl of 60 nM Ligase.

Condition III-E was carried out as follows:
1—Half the volume (~6.5 μl) of each PCR mixture, including the wild-type control, was incubated for 60 min at 65° C. in a 20-41 reaction containing 40 mM Tricine pH8, 5 mM MgCl$_2$, 1 mM DTT, 5% DMSO, 1.5 M betaine, 2% glycerol, and 1 μM EndoV.

2—Fifteen μl of each EndoV cleavage reaction were then subjected to the ligase reaction in a 20-μl final volume during a 60-min incubation at 65° C. This was done by adding 2 μl of 10× supplemental buffer (400 mM Tricine pH8, 12.5 mM MgCl$_2$, 10 mM DTT, 200 μg/ml BSA), 1 μl of 100 mM NAD, and 2 μl of 60 nM ligase.

In addition to sub-condition E, a few other sub-conditions were tested within conditions I and III:

A: 1st incubation with EndoV for 60 min, no 2nd incubation

B: 1st incubation with EndoV for 60 min, 2nd incubation with ligase buffer only for 30 min C: 1st incubation with EndoV for 60 min, 2nd incubation with ligase buffer+ligase for 30 min D: 1st incubation with EndoV for 60 min, 2nd incubation with ligase buffer only for 60 min Condition II-H was carried out as follows:

1—Half the volume (~6.5 μl) of each PCR mixture, including the wild-type control, was incubated for 60 min at 65° C. in a 20-4 μl reaction containing 20 mM Tricine pH8, 5 mM MgCl$_2$, 5 mM DTT, 5% DMSO, 1.5 M betaine, 2% glycerol, in the presence of 1 μM EndoV, 6 nM Ligase and 5 mM NAD.

2—Fifteen μl of each [EndoV+Ligase] reaction were then incubated for 60-min at 65° C. in a 20-μl final volume. This was done by adding 2 μl of 10× supplemental buffer (400 mM Tricine pH8, 12.5 mM MgCl$_2$, 62.5 mM DTT, 200 μg/ml BSA) and 3 μl H$_2$O.

Condition IV-H was carried out as follows:

1—Half the volume (~6.5 μl) of each PCR mixture, including the wild-type control, was incubated for 60 min at 65° C. in a 20 μl reaction containing 40 mM Tricine pH8, 5 mM MgCl$_2$, 5 mM DTT, 5% DMSO, 1.5 M betaine, 2% glycerol, in the presence of 1 μM EndoV, 6 nM Ligase and 5 mM NAD.

2—Fifteen μl of each [EndoV+Ligase] reaction were then incubated for 60-min at 65° C. in a 20-μl final volume. This was done by adding 2 μl of 10× supplemental buffer (400 mM Tricine pH8, 12.5 mM MgCl$_2$, 62.5 mM DTT, 200 μg/ml BSA) and 3 μl H$_2$O.

In addition to sub-condition H, sub-conditions F and G were tested within conditions II and IV:

F: 1st incubation with EndoV+Ligase for 60 min, no 2nd incubation

G: 1st incubation with EndoV+Ligase for 60 min, 2nd incubation with Ligase buffer for 30 min To summarize, conditions I and III were "classical" two-step procedures (1—EndoV, 2-Ligase), while conditions II and IV represented two-step procedures combining both enzymes in the first incubation step (1-[EndoV+Ligase], 2-Ligase buffer). Each PCR mixture, including the wild-type control, was subjected to these various conditions.

Cleavage of both Vic-labeled top strand and Ned-labeled bottom strand was observed on the ABI 3730 fluorescence-based DNA analyzer and the amount of cleavage product was quantified using Gene Mapper fragment analysis software (Applied Biosystems, Foster City, Calif.). Table 6 shows the quantitative data obtained in tested conditions I-E, II-H, III-E, and IV-H as well as in the standard conditions.

The data clearly indicate that all tested conditions give a significant improvement in signal intensity over the standard conditions (see last two columns for fold-improvement in signal). When comparing the signal-to-noise ratios for both G/T and A/C mismatches, it appears that the values obtained from the combined {1—[EndoV+Ligase], 2-Ligase buffer} two-step procedures II-H and IV-H are significantly higher than those of the corresponding {1-EndoV, 2-Ligase} "classical" two-step procedures I-E and III-E, respectively. For instance, the signal-to-noise ratios for the Vic-labeled top cleavage product in conditions III-E and IV-H are 6.3 and 13.6, respectively.

Results are shown in FIG. 22. Top and bottom strand cleavage products are pointed out with green and blue arrows, respectively. Wild-type G-C match, as well as G/T and A/C mismatches (from wild-type+mutant mixtures) are marked on top of the lanes. In addition, details of the incubation conditions are indicated on top of each lane. At the bottom of the gel image, are indicated the lanes encompassed by conditions I through IV. Consistent with quantitative data from Table 6, the gel image discloses a dramatic reduction in the background cleavage under the combined [EndoV+Ligase] conditions as compared to the "classical" two-step conditions. Therefore, the combined [EndoV+Ligase] procedure was retained for further optimization, in particular condition IV-H (40 mM Tricine), which overall gave better fold-improvement in signal than condition II (20 mM Tricine).

TABLE 6

Detecting p53 R273H mutation with the EndoV/Ligase mutation scanning assay: Comparison of various buffer conditions

| Condition | Fragment name | Fragment size (bp) | [G:T] mismatch | [A:C] mismatch | Signal/Noise ratio [G:T] | Signal/Noise ratio [A:C] | Fold improvement in Signal [G:T] | Fold improvement in Signal [A:C] |
|---|---|---|---|---|---|---|---|---|
| Standard | VIC signal | 158 | 650 | 1519 | >4.3 | 4.7 | | |
| 1. EndoV | VIC bgrd | 144 | <150 | 326 | | | | |
| 2. Ligase | NED signal | 194 | 809 | 953 | >5.4 | >6.3 | | |
| | NED bgrd | 115 | <150 | <150 | | | | |
| I-E | VIC signal | 158 | 6352 | 16720 | 4.5 | 9.9 | 9.8 | 11.0 |
| 1. EndoV | VIC bgrd | 144 | 1415 | 1686 | | | | |
| 2. Ligase | NED signal | 194 | 5889 | 7436 | 3.6 | 3.6 | 7.3 | 7.8 |
| | NED bgrd | 115 | 1635 | 2041 | | | | |
| II-H | VIC signal | 158 | 4376 | 16078 | 7.0 | 15.0 | 6.7 | 10.6 |
| 1. EndoV + Lig. | VIC bgrd | 144 | 621 | 1071 | | | | |
| 2. Buffer | NED signal | 194 | 3794 | 6578 | 5.7 | 10.1 | 4.7 | 6.9 |
| | NED bgrd | 115 | 672 | 649 | | | | |

TABLE 6-continued

Detecting p53 R273H mutation with the EndoV/Ligase mutation scanning assay:
Comparison of various buffer conditions

| III-E | VIC signal | 158 | 7726 | 19299 | 3.3 | 6.3 | 11.9 | 12.7 |
|---|---|---|---|---|---|---|---|---|
| 1. EndoV | VIC bgrd | 144 | 2349 | 3086 | | | | |
| 2. Ligase | NED signal | 194 | 7313 | 9402 | 1.6 | 1.8 | 9.0 | 9.9 |
| | NED bgrd | 115 | 4706 | 5302 | | | | |
| IV-H | VIC signal | 158 | 6263 | 16758 | 8.4 | 13.6 | 9.6 | 11.0 |
| 1. EndoV + Lig. | VIC bgrd | 144 | 748 | 1231 | | | | |
| 2. Buffer | NED signal | 194 | 5249 | 7337 | 7.2 | 9.9 | 6.5 | 7.7 |
| | NED bgrd | 115 | 727 | 739 | | | | |

| | | |
|---|---|---|
| Standard conditions: | [40 min] | 1- 1x EndoV buffer = 20 mM Hepes pH 7.5, 5 mM MgCl2, 1 mM DTT, 5% DMSO, 1.5 M Betain, 2% glycerol, with 1 µM EndoV |
| | [30 min] | 2- 1x Ligase buffer = 20 mM Tris pH 8.5, 1.25 mM MgCl2, 50 mM KCl, 1 mM DTT, 20 µg/ml BSA, with 3 nM Ligase + 1 mM NAD |
| Condition I-E: | [60 min] | 1- 1x EndoV buffer = 20 mM Tricine pH 8, 5 mM MgCl2, 1 mM DTT, 5% DMSO, 1.5 M Betain, 2% glycerol, with 1 µM EndoV |
| | [60 min] | 2- 1x Ligase buffer = 40 mM Tricine pH 8, 1.25 mM MgCl2, 10 mM DTT, 20 µg/ml BSA, with 6 nM Ligase + 5 mM NAD |
| Condition II-H: | [60 min] | 1- 1x EndoV buffer = 20 mM Tricine pH 8, 5 mM MgCl2, 5 mM DTT, 5% DMSO, 1.5 M Betain, 2% glycerol, with 1 µM EndoV + 6 nM Ligase + 5 mM NAD |
| | [60 min] | 2- 1x Ligase buffer = 40 mM Tricine pH 8, 1.25 mM MgCl2, 6.25 mM DTT, 20 µg/ml BSA |
| Condition III-E: | [60 min] | 1- 1x EndoV buffer = 40 mM Tricine pH 8, 5 mM MgCl2, 1 mM DTT, 5% DMSO, 1.5 M Betain, 2% glycerol, with 1 µM EndoV |
| | [60 min] | 2- 1x Ligase buffer = 40 mM Tricine pH 8, 1.25 mM MgCl2, 10 mM DTT, 20 µg/ml BSA, with 6 nM Ligase + 5 mM NAD |
| Condition IV-H: | [60 min] | 1- 1x EndoV buffer = 40 mM Tricine pH 8, 5 mM MgCl2, 5 mM DTT, 5% DMSO, 1.5 M Betain, 2% glycerol, with 1 µM EndoV + 6 nM Ligase + 5 mM NAD |
| | [60 min] | 2- 1x Ligase buffer = 40 mM Tricine pH 8, 1.25 mM MgCl2, 6.25 mM DTT, 20 µg/ml BSA |

Example 18

Comparing One-Step Incubation Versus Two-Step Incubation Procedure in the Tma EndoV/Ligase Mutation Scanning Assay A second approach to improving the assay involved the comparison of the standard EndoV/ligase procedure, a combined [EndoV+Ligase] two-step procedure (condition V-H), and a single-step procedure carried out in a 20-µl reaction volume (condition VI-J). p53 exon 8 was amplified in 2 separate "universal" PCR, each of which used 2 primer pairs, as described in Example 8:

The $1^{st}$ "universal" PCR used: 1—forward and reverse universal primers VicUniEV1F and p-UniEV2R; 2—forward and reverse unlabeled gene-specific primers, F173 and R174, which harbor universal tails that are just 3-bp shorter than the universal primer sequence, The $2^{nd}$ "universal" PCR used: 1—forward and reverse universal primers p-UniEV1F and NedUniEV2R; 2—forward and reverse unlabeled gene-specific primers, F173 and R174.

A 350-bp PCR fragment was amplified as described in Example 11. Heteroduplex DNA substrates were prepared using the "split label, denaturation/renaturation" procedure described in Example 10 and illustrated in FIG. 5. As a reference, the EndoV/Ligase reaction was performed under the standard buffer conditions (two-step reaction: [1-EndoV, 2-Ligase]), previously described in Example 10 (FIG. 23). In parallel, each PCR mixture, including the wild-type control, was subjected to 2 other sub-conditions: [1-EndoV, 2—no Ligase] and [1-EndoV, no step 2].

Condition V-H was carried out as follows:
1—Half the volume (~6.5 µl) of each PCR mixture, including the wild-type control, was incubated for 60 min at 65° C. in a 20-µl reaction containing 40 mM Tricine pH8, 5 mM MgCl$_2$, 5 mM DTT, 5% DMSO, 1.5 M betaine, 2% glycerol, in the presence of 500 nM EndoV, 6 nM ligase and 5 mM NAD.

2—Fifteen µl of each [EndoV+ligase] reaction were then incubated for 60-min at 65° C. in a 20-µl final volume. This was done by adding 2 µl of 10× supplemental buffer (400 mM Tricine pH8, 12.5 mM MgCl$_2$, 62.5 mM DTT, 200 µg/ml BSA) and 3 µl H$_2$O.

In addition to sub-condition H, sub-condition F was tested within condition V:
F: 1st incubation with EndoV+Ligase for 60 min, no 2nd incubation Condition VI-J consisted of incubating for 120 min at 65° C. half the volume (~6.5 µl) of each PCR mixture, including the wild-type control, in a 20-µl reaction containing 80 mM Tricine pH8, 5 mM MgCl$_2$, 5 mM DTT, 5% DMSO, 1.5 M betaine, 2% glycerol, with 500 µnM EndoV, 6 mM Ligase and 5 mM NAD (single-step procedure).

In addition to sub-condition J, sub-condition I was tested within conditions VI:
J: 1st incubation with EndoV+Ligase for 120 min, no 2nd incubation Each PCR mixture, including the wild-type control, was subjected to these various conditions. Cleavage of both Vic-labeled top strand and Ned-labeled bottom strand was observed on the ABI 3730 fluorescence-based DNA analyzer and the amount of cleavage product was quantified using Gene Mapper fragment analysis software (Applied Biosystems, Foster City, Calif.).

As shown in Table 7, the signal for either G/T or A/C mismatch was increased in a similar way under both tested conditions in comparison with the standard conditions:

namely, the improvement in Vic signal was 4.3-fold for both conditions V-H and VI-J for the G/T mismatch, and was 5.4- and 4.9-fold for conditions V-H and VI-J, respectively, for the A/C mismatch. The gel image was illustrated in FIG. 23. Top and bottom strand cleavage products are indicated with green and blue arrows, respectively. Wild-type G:C match, as well as G/T and A/C mismatches (from [Wild-type+Mutant] mixtures) are marked on top of the lanes. In addition, details of the incubation conditions are indicated on top of each lane. At the bottom of the gel image, are indicated the lanes encompassed by conditions: Standard, V-H, and VI-J. As confirmed by the quantitative data, the background cleavage resulting from incubating the heteroduplexed substrate with both EndoV and ligase in the same reaction was significantly reduced compared to the standard conditions. The data demonstrate that both one-step and two-step procedures give approximately equivalent results in improving signal intensity and signal-to-noise ratio.

The 1$^{st}$ "universal" PCR used: 1—forward and reverse universal primers VicUniEV1F and p-UniEV2R; 2—forward and reverse unlabeled gene-specific primers, F173 and R174, which harbor universal tails that are just 3-bp shorter than the universal primer sequence.

The 2$^{nd}$ "universal" PCR used: 1—forward and reverse universal primers p-UniEV1F and NedUniEV2R; 2—forward and reverse unlabeled gene-specific primers, F173 and R174.

A 350-bp PCR fragment was amplified as in Example 11. Heteroduplex DNA substrates were prepared using the "split label, denaturation/renaturation" procedure described in Example 10 and illustrated in FIG. 5.

Condition V was carried out as described in Example 18.

Condition VII was similar to condition V, except that 1 mM NAD was used instead of 5 mM.

Condition VI is described in Example 18.

TABLE 7

Detecting p53 R273H mutation with the EndoV/Ligase mutation scanning assay: Comparison of one-step versus two-step incubation procedure

| Condition | Fragment name | Fragment size (bp) | [G:T] mismatch | [A:C] mismatch | Signal/Noise ratio [G:T] | Signal/Noise ratio [A:C] | Fold improvement in Signal [G:T] | Fold improvement in Signal [A:C] |
|---|---|---|---|---|---|---|---|---|
| Standard | VIC signal | 158 | 650 | 1519 | >4.3 | 4.7 | | |
| 1. EndoV | VIC bgrd | 144 | <150 | 326 | | | | |
| 2. Ligase | NED signal | 194 | 809 | 953 | >5.4 | >6.3 | | |
| | NED bgrd | 115 | <150 | <150 | | | | |
| V-H | VIC signal | 158 | 2796 | 8276 | 5.6 | 13.3 | 4.3 | 5.4 |
| 1. EndoV + Lig. | VIC bgrd | 144 | 501 | 622 | | | | |
| 2. Buffer | NED signal | 194 | 2701 | 3650 | >18 | 8.2 | 3.3 | 3.8 |
| | NED bgrd | 115 | <150 | 446 | | | | |
| VI-J | VIC signal | 158 | 2792 | 7493 | 6.8 | 11.8 | 4.3 | 4.9 |
| 1. EndoV + Lig. | VIC bgrd | 144 | 410 | 633 | | | | |
| | NED signal | 194 | 2768 | 4503 | >18 | >30 | 3.4 | 4.7 |
| | NED bgrd | 115 | <150 | <150 | | | | |

| Standard conditions: | [40 min] | 1- 1x EndoV buffer = 20 mM Hepes pH 7.5, 5 mM MgCl2, 1 mM DTT, 5% DMSO, 1.5 M betaine, 2% glycerol, with 1 μM EndoV |
| --- | --- | --- |
| | [30 min] | 2- 1x Ligase buffer = 20 mM Tris pH 8.5, 1.25 mM MgCl2, 50 mM KCl, 10 mM DTT, 20 μg/ml BSA, with 3 nM Ligase + 1 mM NAD |
| Condition V-H: | [60 min] | 1- 1x EndoV buffer = 40 mM Tricine pH 8, 5 mM MgCl2, 5 mM DTT, 5% DMSO, 1.5 M betaine, 2% glycerol, with 500 nM EndoV + 6 nM Ligase + 5 mM NAD |
| | [60 min] | 2- 1x Ligase buffer = 40 mM Tricine pH 8, 1.25 mM MgCl2, 6.25 mM DTT, 20 μg/ml BSA |
| Condition VI-J: | [120 min] | 1x EndoV/Ligase buffer = 80 mM Tricine pH 8, 5 mM MgCl2, 5 mM DTT, 5% DMSO, 1.5 M betaine, 2% glycerol, with 500 nM EndoV + 6 nM Ligase + 5 mM NAD |

Example 19

Comparison of Two NAD Concentrations in Tma EndoV/Ligase Mutation Scanning Assay for Both One-Step and Two-Step Incubation Procedures The effect of the ligase co-factor NAD was also examined for heteroduplex PCR fragments containing p53 exon 8 R273H mutation. NAD concentration was tested on both combined [EndoV+Ligase] two-step procedures (conditions VII and VIII) and single-step procedures (conditions IX and X). p53 exon 8 was amplified in 2 separate "universal" PCR reaction, each of which used 2 primer pairs, as described in Example 8:

Condition VIII was similar to condition VI, except that 1 mM NAD was used instead of 5 mM.

Cleavage of both Vic-labeled top strand and Ned-labeled bottom strand was observed on the ABI 3730 fluorescence-based DNA analyzer and the amount of cleavage product was quantified using Gene Mapper fragment analysis software (Applied Biosystems, Foster City, Calif.). Results (Table 8) show that overall the signal-to-noise ratios are slightly higher at 1 mM NAD than at 5 mM NAD. For the A/C mismatch data, the Vic signal-to-noise ratios are 13.4- and 10.1-fold for conditions VII and VIII (1 mM NAD), as opposed to 6.8- and 5.6-fold for conditions V and VI (5 mM NAD). A similar trend is observed for G/T mismatch, although much less dramatic. Therefore, the subsequent experiments were carried out under the one-step procedure using 1 mM NAD.

TABLE 8

Comparing two NAD concentrations in the EndoV/Ligase mutation scanning assay for both one-step and two-step incubation procedures

| Condition | Fragment name | Fragment size (bp) | [G:T] mismatch | [A:C] mismatch | Signal/Noise ratio [G:T] | Signal/Noise ratio [A:C] |
|---|---|---|---|---|---|---|
| V | VIC signal | 158 | 3319 | 6789 | 3.4 | 6.8 |
| 1. EndoV + Lig. | VIC bgrd | 144 | 982 | 1003 | | |
| 2. Buffer | NED signal | 194 | 3395 | 3758 | >22.6 | >25 |
| | NED bgrd | 115 | <150 | <150 | | |
| VI | VIC signal | 158 | 868 | 2732 | 2.4 | 5.6 |
| 1. EndoV + Lig. | VIC bgrd | 144 | 361 | 488 | | |
| 2. Buffer | NED signal | 194 | 1184 | 2214 | >7.9 | >14.8 |
| | NED bgrd | 115 | <150 | <150 | | |
| VII | VIC signal | 158 | 2997 | 13792 | 4.4 | 13.4 |
| EndoV + Lig. | VIC bgrd | 144 | 680 | 1028 | | |
| | NED signal | 194 | 2717 | 7426 | 3.1 | >49 |
| | NED bgrd | 115 | 867 | <150 | | |
| VIII | VIC signal | 158 | 1688 | 5066 | 3.6 | 10.1 |
| EndoV + Lig. | VIC bgrd | 144 | 464 | 503 | | |
| | NED signal | 194 | 1611 | 3989 | 2.7 | 6.9 |
| | NED bgrd | 115 | 601 | 581 | | |

Condition V: [60 min] 1- 1x EndoV buffer = 40 mM Tricine pH 8, 5 mM MgCl2, 5 mM DTT, 5% DMSO, 1.5 M betaine, 2% glycerol, with 500 nM EndoV + 6 nM Ligase + 5 mM NAD
[60 min] 2- 1x Ligase buffer = 40 mM Tricine pH 8, 1.25 mM MgCl2, 6.25 mM DTT, 20 µg/ml BSA Condition VII: [60 min] 1- 1x EndoV buffer = 40 mM Tricine pH 8, 5 mM MgCl2, 5 mM DTT, 5% DMSO, 1.5 M betaine, 2% glycerol, with 500 nM EndoV + 6 nM Ligase + 1 mM NAD
[60 min] 2- 1x Ligase buffer = 40 mM Tricine pH 8, 1.25 mM MgCl2, 6.25 mM DTT, 20 µg/ml BSA Condition VI: [120 min] 1x EndoV/Ligase buffer = 80 mM Tricine pH 8, 5 mM MgCl2, 5 5 mM DTT, 5% DMSO, 1.5 M betaine, 2% glycerol, with 500 nM EndoV + 6 nM Ligase + 5 mM NAD Condition VIII: [120 min] 1x EndoV/Ligase buffer = 80 mM Tricine pH 8, 5 mM MgCl2, 5 mM DTT, 5% DMSO, 1.5 M betaine, 2% glycerol, with 500 nM EndoV + 6 nM Ligase + 1 mM NAD Example 20

Detection of K-Ras G12V Mutation in an Excess of Wild-Type DNA

In order to determine the sensitivity of the EndoV/Ligase mutation scanning assay under the optimized single-step conditions, PCR fragments containing K-ras exon 1 G12V mutation were used as templates, and the mutation detection abilities of the assay were assessed in different ratios of mutant-to-wild-type DNA ranging from 1:1 to 1:100.

Genomic DNA was extracted from cell lines containing mutation G12V in exon 1 of K-ras gene (codon 12). HT-29 cell line contains the wild-type K-ras gene, while SW480 and SW620 contain pure G12V (G->T) mutation. For K-ras exon 1 amplification, both wild-type and mutant (G12V, G->T) genomic DNA were subjected in parallel to 2 "universal" PCR amplifications, each of which used 2 primer pairs:

The $1^{st}$ "universal" PCR used: 1—forward and reverse universal primers VicUniEV1F and p-UniEV2R, the former fluorescently labeled with Vic on its 5'-end, the latter 5'-phosphorylated; 2-forward and reverse unlabeled gene-specific primers, F161 and R162, which harbor universal tails that are just 3-bp shorter than the universal primer sequence.

The $2^{nd}$ "universal" PCR used: 1—forward and reverse universal primers p-UniEV1F and NedUniEV2R, the former 5'-phosphorylated, the latter fluorescently labeled with Ned on its 5'-end; 2—forward and reverse unlabeled gene-specific primers, F161 and R162.

DNA sequences of these primers are listed in Table 3 VicUniEV1F and NedUniEV2R are internally-labeled with the fluorescent group—Vic or Ned—attached to the C6 of the fourth base (Cytosine 4). Wild-type and mutant genomic DNA were each subjected to a 50-µl "universal" PCR reaction. The "universal" PCR conditions were identical to those described in Example 7. Preparation of heteroduplex DNA substrates was performed using the "split label, denaturation/renaturation" procedure described in Example 10 and illustrated in FIG. 5. However, PCR fragments containing the G12V mutation were mixed with wild-type PCR fragments in the ratio of mutant-to-wild type of 1:1, 1:5, 1:10, 1:20, 1:50, and 1:100. The total amount of PCR fragments was held constant (~1500 ng).

The EndoV/Ligase assay conditions consisted of incubating for either 1 h or 2 h at 65° C. half the volume (~6.5 µl) of each PCR mixture, including the wild-type control, in a 20-µl reaction containing 80 mM Tricine pH 8, 5 mM MgCl$_2$, 5 mM DTT, 5% DMSO, 1.5 M betaine, 2% glycerol, with 1 µM EndoV, 12 nM ligase and 1 mM NAD (single-step procedure).

Cleavage of both Vic-labeled top strand and Ned-labeled bottom strand was observed on the ABI 3730 fluorescence-based DNA analyzer and the amount of cleavage product was quantified using Gene Mapper fragment analysis software (Applied Biosystems, Foster City, Calif.).

Figure 25:
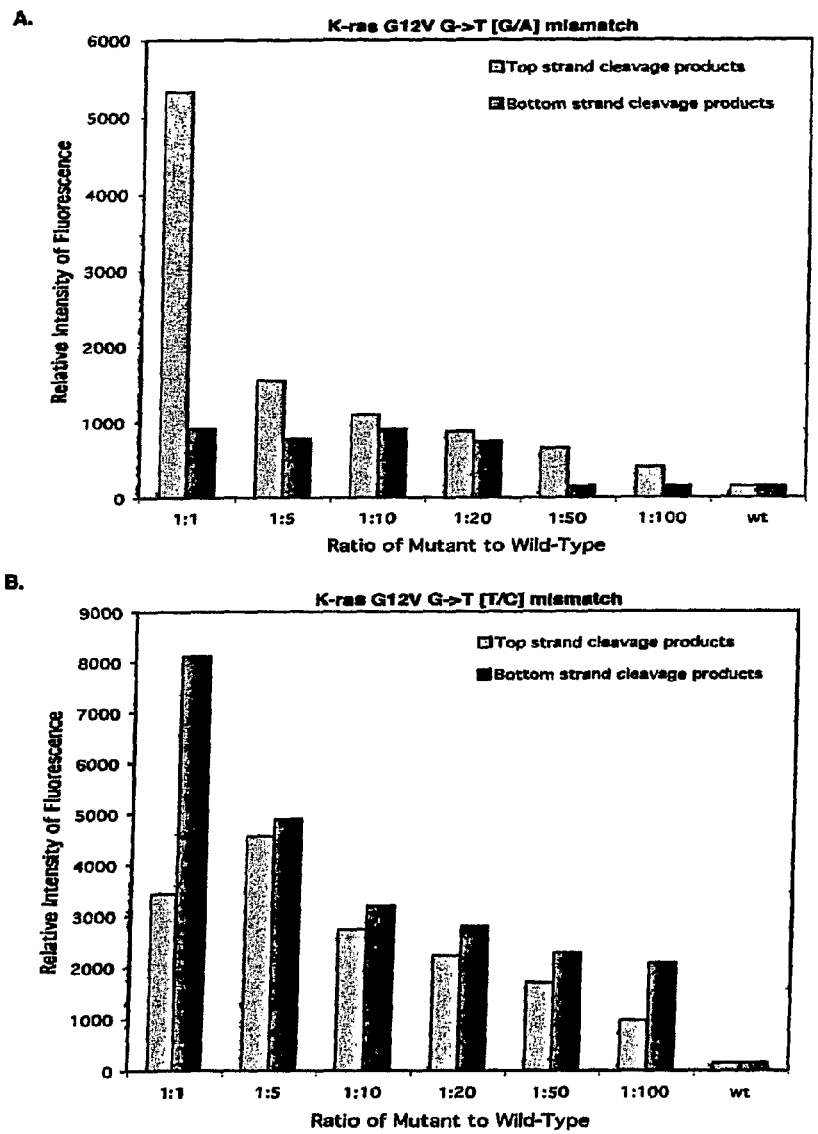

Table 9 shows the quantitative data obtained for the different ratios of mutant-to-wild type DNA. Results indicate that the optimized EndoV/Ligase mutation scanning assay is able to distinguish cleavage signals from background signals in mutant-to-wild type DNA ratios of up to 1:100 for both strands of the T/C mismatch. As for the G/A mismatch, both strands can be distinguished at 1:20, and one strand still provides signal above background at 1:100. Results are illustrated in FIG. 24. FIG. 25 displays graphs representing the amount of cleavage products obtained from the different ratios of mutant-to-wild type DNA, for both G/A (FIG. 25A) and T/C mismatch (FIG. 25B). The peak area was measured by Gene Mapper fragment analysis software and was used for determining the relative fluorescence intensity, after normalizing all values to the GeneScan-500 LIZ Size Standard (the peak area corresponding to the 200-bp DNA fragment was arbitrarily chosen as a reference). Bars indicate the relative fluorescence intensity with their respective mutant-to-wild type ratios: blue bars for the top strand cleavage products, pink bars for the bottom strand cleavage products. The mutation, nucleotide change and mismatch are indicated on top of each graph. These results show that the present assay can distinguish cleavage in 3 out of 4 strands at a sensitivity of 1:100 (mutant-to-wild type DNA).

The 1st "universal" PCR used: 1—forward and reverse universal primers VicUniEV1F and p-UniEV2R; 2—forward and reverse unlabeled gene-specific primers, F173 and R174, which harbor universal tails that are just 3-bp shorter than the universal primer sequence, The 2nd universal" PCR used: 1—forward and reverse universal primers p-UniEV1F and NedUniEV2R; 2—forward and reverse unlabeled gene-specific primers, F173 and R174.

VicUniEV1F and NedUniEV2R are internally-labeled with the fluorescent group—Vic or Ned—attached to the C6 of the fourth base (Cytosine 4). DNA sequences of these primers are listed in Table 3. Wild-type and mutant genomic DNA were each subjected to a 50-μl "universal" PCR. The "universal" PCR conditions were identical to those described in Example 7. Preparation of heteroduplex DNA substrates was performed using the "split label, denaturation/renaturation" procedure described in Example 10 and illustrated in

TABLE 9

Sensitivity of the EndoV/Ligase scanning assay on K-ras G12V

| Ratio of mutant to wild-type | Fragment name | Fragment size (bp) | [G:A] mismatch | [T:C] mismatch | Signal/Noise ratio [G:A] | Signal/Noise ratio [T:C] |
|---|---|---|---|---|---|---|
| 1 to 1 | VIC signal | 133 | 5328 | 3436 | 12.0 | >22.9 |
|  | VIC bgrd | 164 | 445 | <150 |  |  |
|  | NED signal | 174 | 5594 | 8122 | 6.1 | 6.5 |
|  | NED bgrd | 177 | 912 | 1243 |  |  |
| 1 to 5 | VIC signal | 133 | 1546 | 4568 | 4.4 | 6.3 |
|  | VIC bgrd | 164 | 354 | 727 |  |  |
|  | NED signal | 174 | 4096 | 4904 | 5.3 | 3.7 |
|  | NED bgrd | 177 | 773 | 1337 |  |  |
| 1 to 10 | VIC signal | 133 | 1094 | 2749 | 2.1 | >18.3 |
|  | VIC bgrd | 164 | 515 | <150 |  |  |
|  | NED signal | 174 | 2951 | 3216 | 3.3 | 3.5 |
|  | NED bgrd | 177 | 903 | 920 |  |  |
| 1 to 20 | VIC signal | 133 | 880 | 2235 | >5.9 | 4.7 |
|  | VIC bgrd | 164 | <150 | 472 |  |  |
|  | NED signal | 174 | 1781 | 2804 | 2.4 | >18.7 |
|  | NED bgrd | 177 | 742 | <150 |  |  |
| 1 to 50 | VIC signal | 133 | 658 | 1707 | 1.5 | >11.4 |
|  | VIC bgrd | 164 | 447 | <150 |  |  |
|  | NED signal | 174 | 635 | 2292 | >4.2 | 2.6 |
|  | NED bgrd | 177 | <150 | 880 |  |  |
| 1 to 100 | VIC signal | 133 | 404 | 966 | >2.7 | >6.4 |
|  | VIC bgrd | 164 | <150 | <150 |  |  |
|  | NED signal | 174 | <150 | 2090 | ND | >13.9 |
|  | NED bgrd | 177 | <150 | <150 |  |  |

Incubation conditions: 1× EndoV/Ligase buffer = 80 mM Tricine pH 8, 5 mM MgCl2, 5 mM DTT, 5% DMSO, 1.5 M betaine, 2% glycerol, with 1 μM EndoV + 12 nM Ligase + 1 mM NAD [120 min]

Example 21

Detection of p53 R273H Mutation in an Excess of Wild-Type DNA

Similar experiments to those described in Example 20 were conducted on PCR fragments containing p53 exon 8 R273H mutation. Genomic DNA was extracted from cell lines containing mutations in exon 8 of p53 gene (codon 273). LoVo cell line contains wild-type p53 gene, while HT-29 SW480 and SW620 cell line contain the R273H (G->A) mutation. Similar to K-ras PCR amplification in Example 16, p53 exon 8 was amplified in 2 separate "universal" PCR, each of which used 2 primer pairs:

FIG. 5. However, PCR fragments containing the R73H mutation were mixed with wild-type PCR fragments in the ratio of mutant-to-wild type of 1:1, 1:5, 1:10, 1:20, 1:50, and 1:100. The total amount of PCR fragments was held constant (~1500 ng).

The EndoV/Ligase assay conditions consisted of incubating for either 1 h or 2 h at 65° C. half the volume (~6.5 μl) of each PCR mixture, including the wild-type control, in a 20-μl reaction containing 80 mM Tricine pH 8, 5 mM MgCl2, 5 mM DTT, 5% DMSO, 1.5 M betaine, 2% glycerol, with 1 μM EndoV, 12 nM ligase, and 1 mM NAD (single-step procedure).

Cleavage of both Vic-labeled top strand and Ned-labeled bottom strand was observed on the ABI 3730 fluorescence-based DNA analyzer and the amount of cleavage product was quantified using Gene Mapper fragment analysis software (Applied Biosystems, Foster City, Calif.).

TABLE 10

Sensitivity of the EndoV/Ligase scanning assay on p53 R273H

| Ratio of mutant to wild-type | Fragment name | Fragment size (bp) | [G:T] mismatch | [A:C] mismatch | Signal/Noise ratio [G:T] | Signal/Noise ratio [A:C] |
|---|---|---|---|---|---|---|
| 1 to 1 | VIC signal | 158 | 3153 | 13602 | 3.6 | 9.3 |
|  | VIC bgrd | 144 | 868 | 1466 |  |  |
|  | NED signal | 194 | 2451 | 9277 | 2.4 | 9.6 |
|  | NED bgrd | 115 | 1021 | 967 |  |  |
| 1 to 5 | VIC signal | 158 | 1685 | 9046 | 1.9 | 6.6 |
|  | VIC bgrd | 144 | 871 | 1371 |  |  |
|  | NED signal | 194 | 3424 | 3169 | >22.8 | 2.5 |
|  | NED bgrd | 115 | <150 | 1284 |  |  |
| 1 to 10 | VIC signal | 158 | 1266 | 4603 | 2.7 | 5.0 |
|  | VIC bgrd | 144 | 461 | 929 |  |  |
|  | NED signal | 194 | 1606 | 1997 | 1.5 | 1.5 |
|  | NED bgrd | 115 | 1053 | 1354 |  |  |
| 1 to 20 | VIC signal | 158 | 1525 | 2729 | 1.8 | 3.4 |
|  | VIC bgrd | 144 | 857 | 807 |  |  |
|  | NED signal | 194 | 1625 | 1028 | 1.4 | 1.0 |
|  | NED bgrd | 115 | 1140 | 1038 |  |  |
| 1 to 50 | VIC signal | 158 | 1258 | 1418 | 1.6 | 2.0 |
|  | VIC bgrd | 144 | 799 | 709 |  |  |
|  | NED signal | 194 | <150 | 992 | ND | 0.9 |
|  | NED bgrd | 115 | 1101 | 1100 |  |  |
| 1 to 100 | VIC signal | 158 | 542 | <150 | 0.9 | ND |
|  | VIC bgrd | 144 | 615 | 1697 |  |  |
|  | NED signal | 194 | <150 | <150 | ND | ND |
|  | NED bgrd | 115 | 652 | 1931 |  |  |

Incubation conditions: 1x EndoV/Ligase buffer = 80 mM Tricine pH 8, 5 mM MgCl2, 5 mM DTT, 5% DMSO, 1.5 M betaine, 2% glycerol, with 1 µM EndoV + 12 nM Ligase + 1 mM NAD [120 min]

The results in Table 10 indicate that the assay is able to distinguish cleavage signals from background signals in mutant-to-wild type DNA ratios of up to 1:20. However, it is noteworthy that while the cleavage signal is significantly above background for the G/T mismatch (1.8- and 1.4-fold for Vic and Ned signals, respectively), and for the A-C mismatch Vic signal (3.4-fold), the signal-to-noise ratio is only equal to 1 for the A/C mismatch Ned signal, which is right below the criterion of significance.

Figure 27:
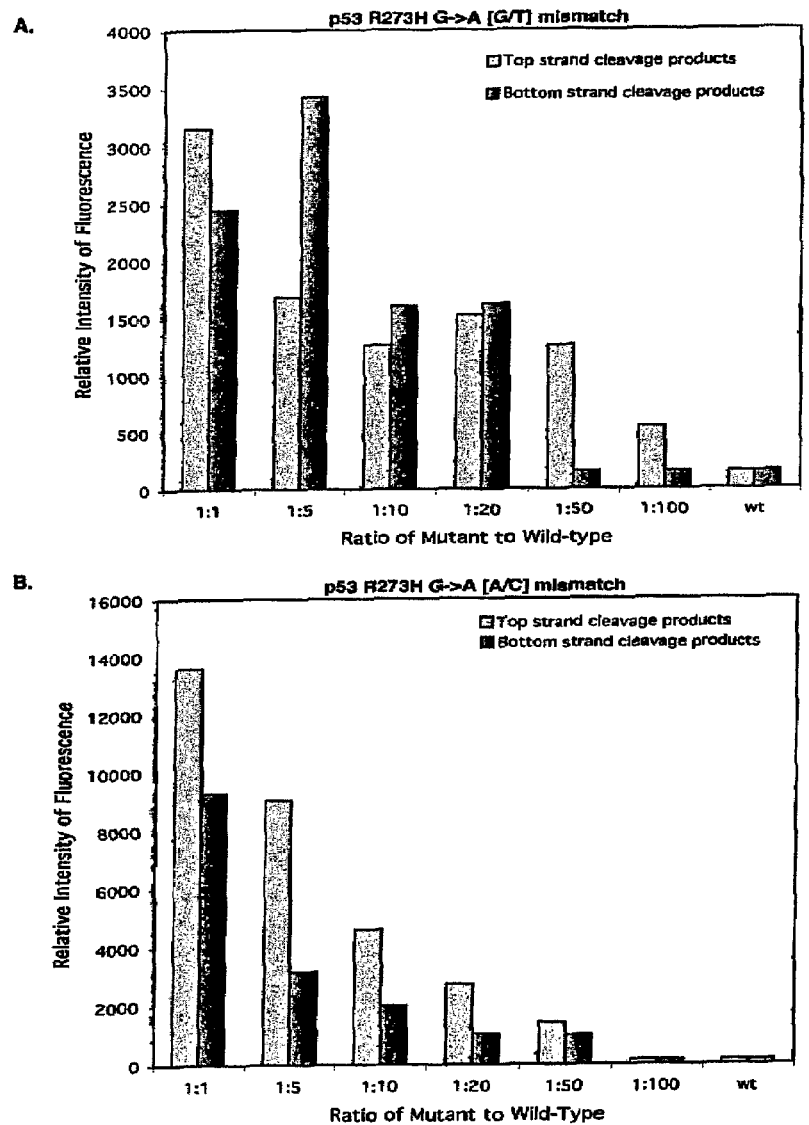

The gel image is also depicted in FIG. 26. FIG. 27 displays graphs representing the amount of cleavage products obtained from the different ratios of mutant-to-wild type, for both G/T (FIG. 27A) and A/C mismatch (FIG. 27B). DNA. Results indicate that the optimized EndoV/Ligase mutation scanning assay is able to distinguish cleavage signals from wild-type signals in mutant-to-wild type DNA ratios of up to 1:20 for both strands of the G/T mismatch, and up to 1:100 for the G strand. For the A/C mismatch, both strands can be distinguished at 1:50. The peak area was measured by Gene Mapper fragment analysis software and was used for determining the relative fluorescence intensity, after normalizing all values to the GeneScan-500 LIZ Size Standard (the peak area corresponding to the 200-bp DNA fragment was arbitrarily chosen as a reference). Bars indicate the relative fluorescence intensity with their respective mutant-to-wild type ratios: blue bars for the top strand cleavage products, pink bars for the bottom strand cleavage products. The mutation, nucleotide change and mismatch are indicated on top of each graph. These results show that the present assay can distinguish cleavage in 3 out of 4 strands at a sensitivity of 1:50 (mutant-to-wild type DNA) for p53 exon 8.

This application presents a significantly improved EndoV/Ligase mutation scanning assay that was achieved by separating the substrate preparation step (DNA amplification, heteroduplex formation), from the mutation query step (EndoV/Ligase), and from the mutation detection step (separation by capillary electrophoresis or hybridization onto the chip). This orthogonal approach allows for optimization of each component separately to achieve maximum signal-to-noise discrimination in the integrated system.

For the purposes of illustrating the ideas below, one PCR amplicon will be considered at a time. However, the concept is intended for use with multiple PCR amplicons (ultimately hundreds to thousands). These amplicons are generated separately and subsequently pooled, or multiplexed (e.g. using the PCR/PCR protocol), or by combining the two approaches.

Figure 1:
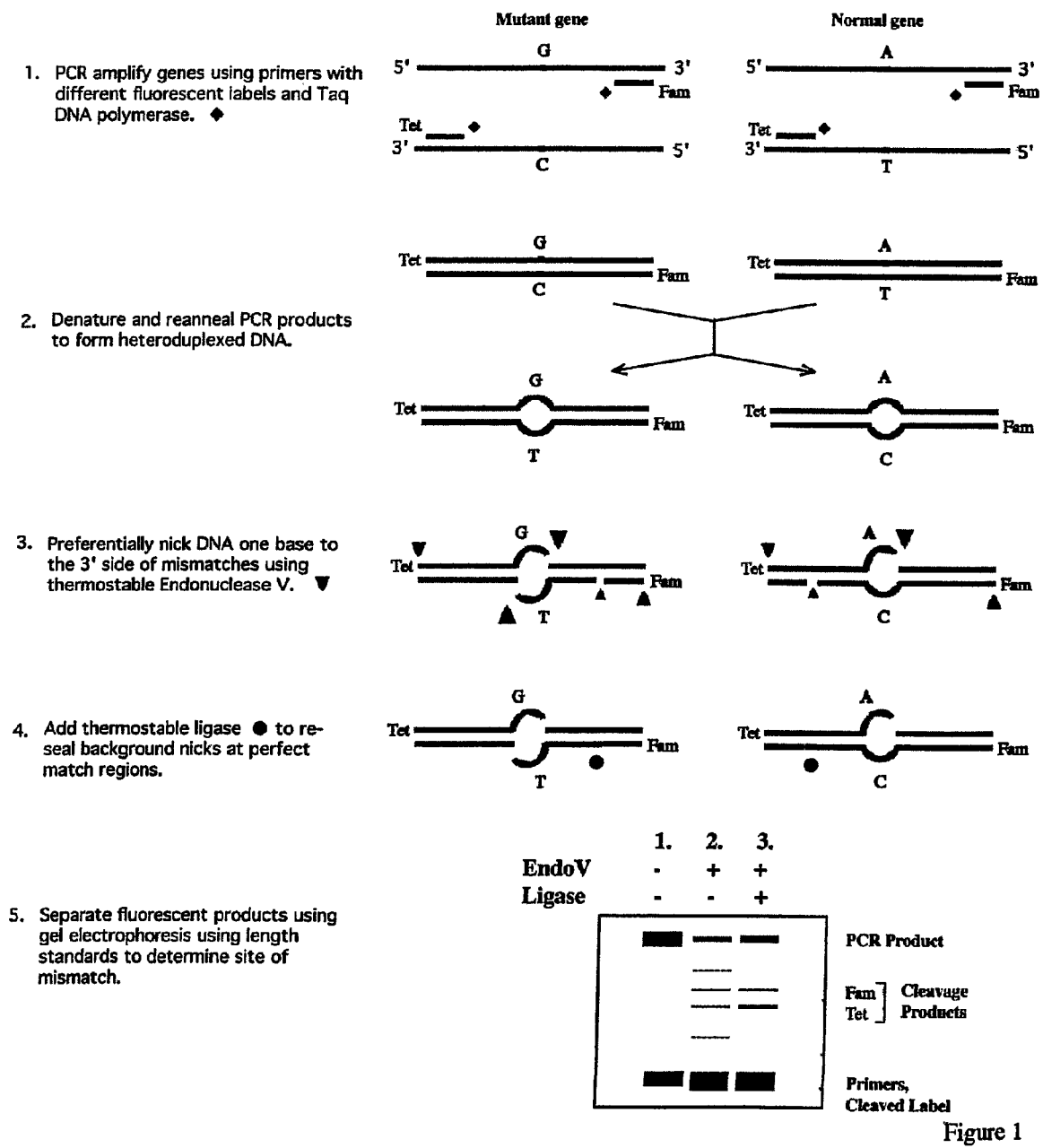
FIG. 1 is a schematic drawing, illustrating a prior art procedure for the EndoV/Ligase mutation scanning assay with detection of fragments by gel electrophoresis.

The EndoV/Ligase mutation scanning assay generates a number of unique products (See FIG. 1). In the standard electrophoresis-based assay, the presence of a mutation is scored by appearance of a unique length product containing a fluorescent label at the 5' end. In the array-based readout methods described herein, a mutation is scored by either: (i) presence of a newly generated 3'OH, and the adjacent unique bases of upstream sequence, (ii) presence of a newly generated 5'phosphate, and the adjacent unique bases of downstream sequence, or (iii) presence of a newly generated 3'OH, and unique bases of upstream sequence, as displayed on a universal array. Such an assay should ideally avoid false-positives due to short fragments generated by EndoV near the ends, and false-negatives due to weak activity of EndoV on one or the other strand for mutations in certain GC rich sequences.

Cleavage/Ligation/Capillary Electrophoresis

After PCR products are treated with a standard denaturation/renaturation step, four potential reannealed products can form: (i) top strand mutant: bottom strand wild-type heteroduplex, (ii) top strand mutant: bottom strand mutant homoduplex, (iii) top strand wild-type: bottom strand wild-type homoduplex, and (iv) top strand wild-type: bottom strand mutant heteroduplex. Only two of these products can generate signal that would indicate the presence of a mutation or polymorphism, while the other two products could only generate signal that adds to the background noise. For example, when generating heteroduplexes from wild-type and mutant sequence representing a G→A transition mutation, the four products contain two mismatches (A/C, G/T) and two matches (A:T, G:C) respectively.

One approach to improving signal-to-noise is to generate heteroduplexed sequences that are of only one type, i.e. pure A/C mismatch. This may be achieved by a number of procedures that selectively capture one strand, or selectively remove one strand. For example, mutant DNA may be PCR amplified with the top strand primer containing a fluorescent label, and the bottom strand primer phosphorylated at the 5' end. Simultaneously, wild-type DNA is PCR amplified with the top strand primer phosphorylated, and the bottom strand primer containing a fluorescent label at the 5' end. When these two products are combined and the phosphorylated strands digested away using lambda exonuclease, the resultant single strands may reanneal to form a heteroduplex of top strand mutant: bottom strand wild-type (FIG. 2, see also FIG. 6). Improved signal-to-noise is achieved when using lambda exonuclease to generate heteroduplexed substrates (See FIGS. 13-16).

It has previously been demonstrated that addition of DMSO (5%) and betaine (1.0 to 1.5M) significantly enhances cleavage of heteroduplexed PCR fragments (Huang et al, *Oncogene* 21(12):1909-21 (2002), which is hereby incorporated by reference in its entirety). In order to test whether other additives also enhance EndoV cleavage, the use of tetramethylene sulfoxide and tetramethylene sulfone were explored. Tetramethylene sulfone was shown to enhance PCR product yields when amplifying template DNA with a high GC content (Chakrabarti, R., et al., *Gene,* 274(1-2):293-8 (2001), which is hereby incorporated by reference in its entirety). Tetramethylene sulfoxide has a similar chemical group as DMSO (dimethyl sulfoxide) (See FIG. 17).

The two chemicals were added either during heteroduplex formation or EndoV cleavage reaction, or in both reactions. In addition, EDTA was also added during the hybridization step. A detailed description of these experiments is provided in Example 13, (see FIG. 18). It was demonstrated that 5% tetramethylene sulfoxide, or 5% tetramethylene sulfone may be used instead of 1.5M betaine and 5% DMSO during the EndoV reaction. This provides a broader range of buffer conditions to optimize simultaneous EndoV cleavage and ligase resealing, as demonstrated below.

Preventing Loss of 5' Label During EndoV Mutation Scanning Assays

One drawback of the method shown in FIG. 1 is that when products were separated by capillary electrophoresis two unanticipated bands appeared: a broad yellow band that migrates at about 94 bases (Ned), and a broad green band that migrates at about 102 bases (Vic) (See FIG. 3 for schematic illustration). Extensive controls revealed that these products were dependent on the presence of EndoV, yet were removed by filtration with a 10 kDa cutoff. These bands are thus most likely a cleavage product containing the 5' fluorescent label, a phosphate group (to provide charge) and most likely, an additional base. These bands created two problems for the standard EndoV/Ligase assay: (1) The two cleaved label bands would interfere with detection of an authentic band arising from a mutation that migrated in the same position, and (2) The loss of signal significantly reduced the ability to distinguish true signal (arising from cleavage at a mutation) from noise (arising from cleavage at a matched position). (While loss of signal due to cleavage of the Fam or Tet label used with gel electrophoresis detection on an ABI 377 was previously observed, the cleaved label migrated near the labeled primer on the standard gel, and thus was not such a serious problem). Finally, it was observed that the EndoV retained activity and cleaved the 5' label off heteroduplexed fragments, even within the capillary during electrophoresis (despite having been denatured in formamide).

To avoid loss of signal due to EndoV cleavage of label off the 5' end, a number of modified labeled primers were evaluated (See FIG. 3). These modifications include:

1. Two 2'O-methylated C were inserted between the label and the 5' end of the primers.
2. A sequence, CGCCGC, was added at 5' end of the primer. This sequence has been shown to be refractory to EndoV cleavage when positioned in the middle of a fragment (Huang, J., et al., *Oncogene,* 21(12):1909-21 (2002), which is hereby incorporated by reference in its entirety).
3. Both two 2'O-methylated C and an EndoV resistant sequence (CGCCGC) were added at 5' end of the primer.
4. An C-c6-Vic (or Ned) was inserted at the $4^{th}$ or $5^{th}$ position from the 5' end within the resistant sequence (e.g. CGC(C-c6-Ned)G). This primer design is also referred as internally-labeled primer. Vic and Ned are fluorescent groups developed at ABI (Applied Biosystems, Foster City, Calif.).
5. The Vic or Ned label is attached in the reverse orientation, i.e. 3'-Vic-5'-5' gene-specific oligonucleotide 3'.

Figure 20:
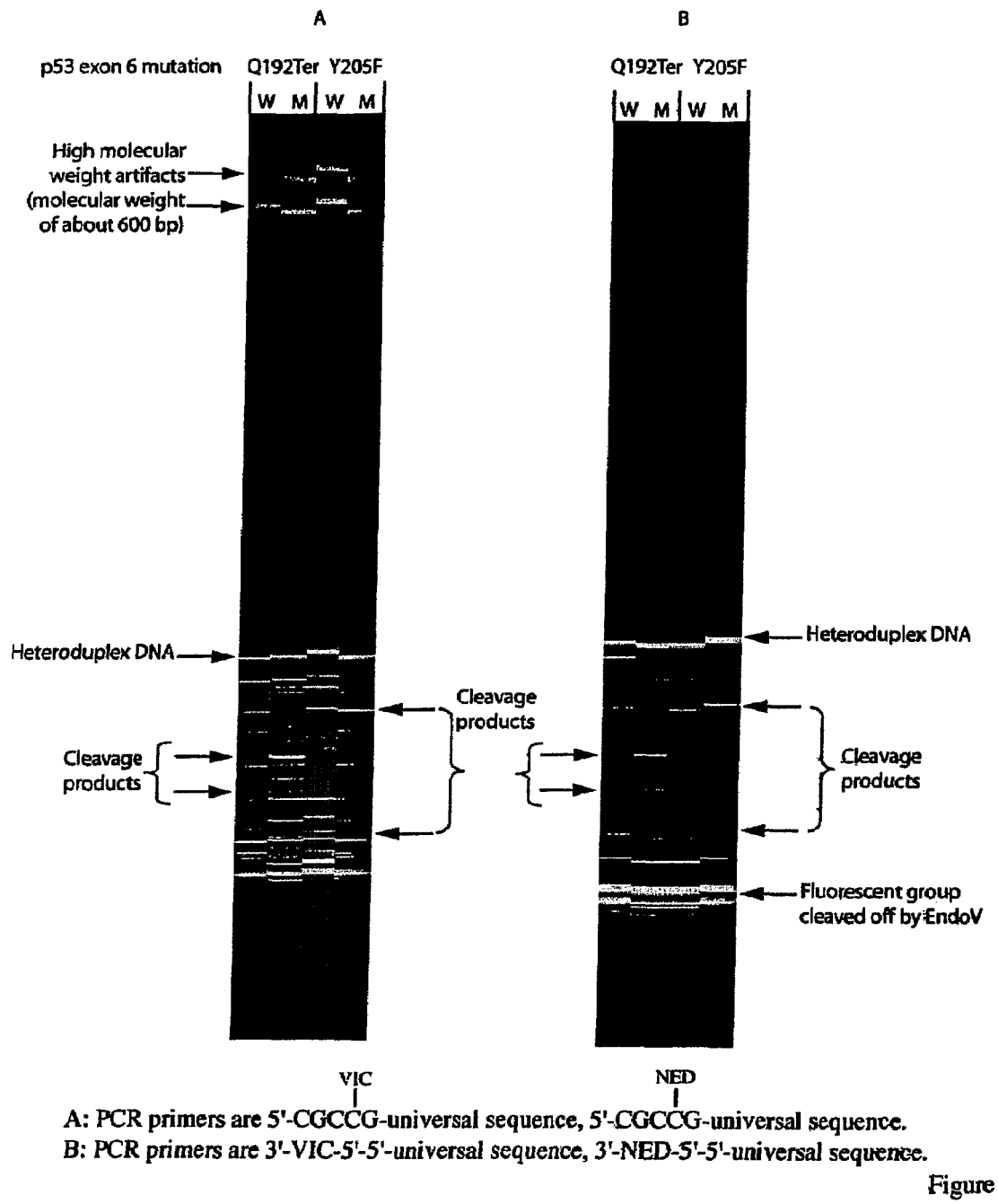

In addition, EDTA was included in the formamide to remove the metal cofactor, and assure no activity after the reaction was terminated. Only the internally-labeled primers were fully resistant to EndoV cleavage (FIG. 19 and Example 14). However, these also gave a higher molecular weight artifact that migrated around 600 bp (FIG. 20). Use of 3'-label 5-5' oligonucleotide primers eliminated the higher molecular weight artifact, however, some of the label was still cleaved by EndoV (see Example 15). Both internal label and reversed linkage modifications solved the label cleavage problem, provided excellent signal, and were used for subsequent experiments with universal primers.

Using internally-labeled primers as PCR primers, DNA from several clinical samples that have mutations in K-ras exon1, p53 exon 5, 6, 7 and 8 were amplified. The EndoV reactions were carried out under standard conditions (See Example 16). Since this experiment was designed to determine if mutation cleavage products could be distinguished even in a high background, the ligation step was omitted. Compared with cleavage products from wild type PCR products, it was shown that using internal labeled primers, mutations in these samples can be significantly detected after electrophoresis of cleavage products in a 3730 DNA sequencer (See FIG. 21 and Example 16).

Heteroduplex Formation and Higher Throughput EndoV Mutation Scanning Assays

The EndoV assay is sensitive enough to distinguish one mutant sequence in a 20-fold excess of unaltered DNA. This is useful when attempting to find the presence of a low abundance mutation in an excess of wild-type DNA. Further, the method is amenable to pooling of different DNA samples from various patients to look for the appearance of a new mutation. It is also amenable to pooling many different exons or genes, and determining the presence of a mutation in a single sample.

Tumor samples are often limiting in DNA. Thus, it may be prudent to pre-amplify DNA prior to performing individual EndoV mutation scanning assays. This may be achieved using whole genome amplification under conditions where the average fragment size generated is larger than the amplicon size required for the EndoV reaction. Another approach is to generate a representation of the sample, for example by cleaving it with a restriction endonuclease, ligating on linkers, and amplifying a defined size class of fragments. The advantage of a representational amplification is that a single primer pair amplifies multiple fragments for further analysis. However, the fragment(s) to be assayed ultimately need to be present within the representation.

If the genes or regions to be queried are known, they may be amplified together, herein termed a "directed-representational amplification". Here, gene-specific primers are synthesized containing the same universal primer sequence on their 5' end. These primers are pooled and used at low concentration to PCR amplify multiple fragments together for a limited number of cycles. Although use of large numbers of primers in a single PCR reaction runs the risk of amplifying unwanted products, their yields will be no greater than desired products since the PCR cycles are limited. Further, these extra fragments are equivalent to extra fragments in a whole genome or representational amplification. The principles of representational or directed-representational amplification also hold for amplification of fragments from cDNA.

Subsequently, one or more fragments of genomic or a representation of genomic target DNA are PCR amplified using a low concentration of gene-specific/universal primers and Taq polymerase (See FIG. 4). In the same or a subsequent reaction, a high concentration of labeled universal primers are present, containing the same sequence and additional marker bases on their 3' end. The PCR reaction is continued at a lower temperature and the labeled fragments predominate. Since the two universal primers share the same sequence, primer dimers do not amplify. The unique marker bases on the 3' end assure that each universal primer amplifies (and labels) only the intended strand. In a separate (or the same) reaction, PCR amplifies normal DNA as above. Products are denatured and renatured to generate labeled heteroduplexed fragments. The reaction may be performed with only one universal primer labeled at a time, herein termed "split label, denaturation/ renaturation" as illustrated in FIG. 5. Alternatively, the PCR amplification may be performed with neither universal primer labeled, for subsequent array detection.

Gene-specific/universal primers and universal primers have been designed so they can amplify the desired target in a single homogeneous reaction. The gene-specific portion of the gene-specific/universal primer is designed to have a Tm-value of about 70-72° C. (calculated using Oligo 6.0 software). The universal portion of the gene-specific/universal primer is slightly shorter than full-length universal primer, and designed to have a Tm-value of about 56-57° C. (calculated using Oligo 6.0 software). The universal primers were designed to have the same sequence on their 5' portions, (about 18 bases, differing only in the fluorescent label if present) and either a 3' CA or 3' AC sequence. These 3' differences assure that each universal primer amplifies (and labels) only the intended strand. (See Examples 7 and 8 and Table 3).

In the PCR reaction to prepare EndoV substrates, the initial gene-specific portion of the amplification takes place at a higher temperature, such that the gene-specific/universal primers can amplify genomic DNA or their own fragments (i.e. 94° C. 30 sec, 65° C. 1 min, 72° C. 1 min, 20 cycles). Subsequently, the temperature is lowered to allow the universal primers to bind and extend the initial PCR products, and cycling can be continued, either at the lower temperature (i.e. 94° C. 30 sec, 55° C. 1 min, 72° C. 1 min, 30 cycles). There may be advantages to raising the temperature again after a few initial cycles to increase the efficiency of the second PCR as explained below. (i.e. 94° C. 30 sec, 55° C. 1 min, 72° C. 1 min, 5 cycles, followed by 94° C. 30 sec, 65° C. 1 min, 72° C. 1 min, 20 cycles).

In a standard PCR reaction, the two primers are different, so each primer hybridizes uniquely to its own site. In PCR/ PCR where the universal primer is identical throughout, a single primer hybridizes to both sites. However, for the EndoV reaction, the universal primers have unique 3' ends to assure that they only extend on the correct strand. (The 5' side is kept identical or mostly identical such that it prevents primer dimer formation). With two primers able to hybridize to either sequence, but only one of the two able to extend correctly, the yields from the PCR reaction will be reduced. The level of reduction is a function of the efficiency of hybridizing to the correct site. If there is no discrimination between the two binding events, the efficiency will be at or around 50% and, if the 3' end of the primer contributes significantly to the efficiency of binding (as would occur when the cycling temperature approaches the primer Tm value), then the efficiency will be higher (about 70% to 90%).

For example, to obtain a billion-fold amplification with normal PCR takes 30 cycles. Below are the number of cycles required with 2 universal primer PCR (number of cycles required for given efficiency): 53 cycles with 50% efficiency; 45 cycles with 60% efficiency; 40 cycles with 70% efficiency; 36 cycles with 80% efficiency; and 33 cycles with 90% efficiency.

To calculate the theoretical amount of amplification, the formula for standard PCR is: Amplification=$(2X)^N$, where X is the efficiency of a single cycle, and N is the number of cycles.

For X=1, N=10; Amplification=1024

For X=1, N=20; Amplification=1,048, 576

To calculate the theoretical amount of amplification, the formula for 2 primer PCR is: Amplification=$((1+\%\text{ efficiency})X)^N$, where X is the efficiency of a single cycle, % efficiency is the % of correct primer binding to correct site, and N is the number of cycles. For example:

For X=1, efficiency=50%, N=10; Amplification=57.66=58

For X=1, efficiency=80%, N=10; Amplification=357.0

For X=1, efficiency=50%, N=20; Amplification=3325

For X=1, efficiency=80%, N=20; Amplification=127,482

Thus, the universal PCR amplification scheme described above achieves the aim of avoiding primer dimers, allowing for multiplexed amplification of many fragments, and uniquely labeling each strand. The primer sets and universal primers may be used together in a single homogeneous reaction, but the design requires more amplification cycles than a standard PCR reaction.

The above approaches generate both heteroduplex and homoduplex DNA. To generate only heteroduplex DNA, PCR amplify one or more fragments of target DNA using a low concentration of gene-specific/universal primers and Taq DNA polymerase, as illustrated in FIG. 6. In the same or a subsequent reaction, a high concentration of one labeled and one phosphorylated universal primers are present, containing the same sequence and additional marker bases on their 3' ends. The PCR reaction is continued at a lower temperature and the labeled fragments predominate. Since the two universal primers share the same sequence, primer dimers do not amplify. The unique marker bases on the 3' end assure that each universal primer amplifies (and labels) only the intended strand. In a separate reaction, PCR amplify normal DNA as above, but switch which universal primer is labeled and which contains the phosphate group. The two PCR products are mixed and treated with lambda exonuclease to digest the phosphorylated primers and products, allowing the remaining strands to form heteroduplexed DNA. Reverse primer sets to generate the complementary heteroduplex set. The formation of heteroduplexed DNA from newly generated single strands may be aided by use of additional buffer supplements such as cationic detergents or proteins such as single-strand binding protein and/or RecA, that are known to promote hybridization reactions. The reaction may be performed with only one universal primer labeled at a time (as illustrated in FIG. 5), or with neither universal primer labeled, for subsequent array detection.

For the array experiments, it may be necessary to assure that all single-stranded or incomplete PCR products or partially heteroduplexed fragments are removed. To achieve this, PCR amplify one or more fragments of target DNA using a low concentration of gene-specific/universal primers and Taq DNA polymerase (FIG. 7). In the same or a subsequent reaction, a high concentration of phosphorylated universal primers containing the same sequence and additional marker based on their 3' end, are present. The PCR reaction is continued at a lower temperature and the phosphorylated fragments predominate. Since the two universal primers share the same sequence, primer dimers do not amplify. The unique marker bases on the 3' end assure that each universal primer amplifies (and labels) only the intended strand. In a separate reaction, PCR amplify normal DNA as above, using universal primers containing additional bases on their 5' ends. Denature and renature products to generate heteroduplexed fragments with asymmetrical "sticky ends". Linkers with corresponding overhangs are ligated with T4 ligase, only to the correct heteroduplexed ends. Companion linkers may be used that ligate to ends containing an additional 3' A, often added to the ends of PCR products by Taq DNA polymerase. The linkers contain blocking groups to render the heteroduplexed DNA resistant to a subsequent exonuclease digestion. Either 3'→5' exonucleases (such as *E. coli* ExoI and ExoIII), or 5'→3' exonuclease (such a lambda exonuclease) or both types may be used. Since the heteroduplexes generated have non-identical overhangs, a separate or the same reaction contains linkers for protection of the complementary heteroduplex.

In all of the above procedures, it should be noted that one of the primers may contain a capture group (such as biotin), allowing for capture of a specific strand, and release of the complement in solution (e.g. by either heat or base denaturation). Mixing a captured wild-type strand with a soluble mutant strand (in a neutral pH solution) would allow for formation of heteroduplexes. These heteroduplexes may be captured and purified with streptavidin coated para-magnetic beads.

To summarize the above approaches, they allow for simultaneous amplification of one or more fragments to create substrates suitable for EndoV mutation scanning. This allows for several types of pooling reactions. The most straightforward is to PCR amplify a number of samples and then pool the products (for example, in groups of 3 to 10) before EndoV mutation scanning. Since the probability that a new mutation or polymorphism is in the identical place in all samples is very small, the screen should find a new mutation. If the DNA is very clean, and/or accurately quantified, the samples may be pooled prior to PCR amplification. An alternative approach is to amplify half of the samples with the Top strand labeled, and the other half with the bottom strand labeled. These two sets are combined and heteroduplexed either by denaturation/renaturation, or using lambda exonuclease to generate pure heteroduplexed fragments. Simultaneously, the second half samples are amplified with the top strand being labeled and combined with the first half of samples having the bottom strand labeled. Again, the probability that a new mutation or polymorphism will be present in all the samples is very small. However, one can now look at twice the number of samples per lane as previously.

The above approaches are based on identifying mutations within the same target region per lane for multiple samples, where the frequency of mutation or polymorphism is significantly less than the number of samples pooled into a given lane. The limit of sensitivity for the assay is determined by the ability to detect the mutant signal above the cumulative background signal from the other (wild-type) samples. In a different approach, multiple regions of target DNA from a single sample are co-amplified, such that all the fragments are approximately the same length. In this approach, each fragment generates background signal, but that background signal will be randomly distributed such that a mutation signal would be easily distinguished. One variation of this idea is to divide the target gene or area into consecutive regions (e.g. exons and intron junction sequences) of 600 bases or less. A first multiplexed PCR reaction amplifies the odd numbered regions, while a second multiplexed PCR reaction amplifies the even numbered regions. This allows for use of primers that generate fragments that may contain some overlaps, such that large exon sequences are still fully covered in either the even or odd set of PCR products.

In all of the aforementioned approaches, appropriate controls are needed to distinguish common polymorphisms from new polymorphisms and mutations. In addition, once a mutation signal is detected, one needs to scan and then sequence the individual samples or fragments from the pool to pinpoint the mutation.

Single Step Cleavage/Ligation Reactions

Endonuclease V recognizes some perturbation from perfectly double-stranded DNA that allows for cleavage of the phosphate backbone. Given the wide range of substrates that are recognized and cleaved by this enzyme, ranging from apurinic sites to uracil-containing sites to insertions, deletions, and mismatches, it is difficult to predict what type of perturbation will be strongly cleaved under a given set of conditions. To assure cleavage of the more refractory mismatches, organic solvents and other additives are used to help push the phosphate backbone towards a cleavable conformation. These conditions in turn allow for normal homoduplexed DNA to be cleaved at specific sites. In some cases, the normal sequence is cleaved even more efficiently than a refractory mismatch such as the R273H mutation in p53.

Examples 17 and 18 (See FIGS. 22 and 23, as well as Tables 6 and 7) demonstrate that judicial choice of conditions will allow accumulation of the desired fragment length for a mismatched site in excess of a background signal from the matched site, even though the later is cleaved more effectively than the former under the optimal buffer conditions. This condition may be achieved by adding ligase concurrently with the Endonuclease V. Although matched sites are cleaved more efficiently, they are also religated more efficiently, and, consequently, the weaker signal at the mismatched site has an opportunity to accumulate. Buffer conditions and enzyme concentrations need to be optimized such that products arising from mismatch cleavage/resealing accumulate more rapidly than products arising from match cleavage/resealing. For these conditions to be met, the rate constants of the four reactions in the given buffer need to satisfy the following equations:

$$k_{MmCleavage} - k_{MmLig} > k_{MCleavage} - k_{MLig}$$

and $$k_{MmCleavage} - k_{MmLig} > 0$$

Where:
$k_{MmCleavage}$=rate of Mismatch cleavage
$k_{MCleavage}$=rate of Match cleavage
$k_{MmLig}$=rate of Mismatch ligation
$k_{MLig}$=rate of Match ligation Although individual ligation and cleavage rates were not directly determined, several homogeneous conditions that allowed for the above equations to hold were determined (See FIGS. 22 and 23 and Tables 6 and 7).

These modifications significantly enhance the overall mutation signal and the signal-to-noise ratio. For example, signal improved from 4.7 to 12.7-fold over standard conditions, and signal-to-noise improved from a range of 4.3-6.3 up to 15-fold (Tables 6 and 7). Consequently, the improved method is sensitive enough to identify mutations or polymorphisms, wherein the ratio of the mutant nucleic acid sequence to the normal target nucleotide sequence is in a range of 1:1 up to 1:100. It was demonstrated that enhanced cleavage in at least ¾ strands of the G/A and T/C mismatch for K-ras G12V mutation up to 1:100 (Example 20, FIGS. 24 and 25, Table 9) and enhanced cleavage in at least ¾ strands of the G/T and A/C mismatch for the p53 Exon 8 R273H mutation up to 1:50 (Example 21, FIGS. 26 and 27, Table 10) can be achieved.

Cleavage/Ligation/Microarray

A number of different schemes may be considered for detecting the presence of new mutations using either gene-specific or universal arrays (FIGS. 8-11).

In general, heteroduplexes are formed between test and normal DNA as illustrated in FIGS. 4-8. The test DNA may be genomic DNA, cDNA, or a PCR amplification from either of these initial sources. The normal DNA may be either no additional DNA (i.e. the test DNA sample also contains normal DNA, as in a cancer sample that contains both tumor and stromal cells), cloned DNA, or a PCR amplification of genomic or cDNA. If needed, the heteroduplexed DNA is capped and captured using a solid support, such as capture of a ligated biotinylated linker by streptavidin coated para-magnetic beads. The heteroduplexed DNA is treated with EndoV and inappropriate nicks resealed with ligase (FIGS. 8-11, Steps 1 & 2). Three subsequent variations may be used to capture the newly generated 3'OH or 5' phosphate. In the first variation, the 3'OH end is tailed with terminal transferase, and the newly generated fragment PCR amplified using a labeled primer and an upstream phosphorylated primer (FIGS. 8 and 9). In a second variation, a downstream primer is annealed and extended to create a blunt end with the newly generated 5' phosphate. A linker is ligated onto this blunt end using T4 ligase. The newly generated fragment is PCR amplified using a labeled linker primer and a downstream phosphorylated primer (FIG. 10). In these two variations, the PCR amplification step incorporates dUTP, allowing for nicking at these positions with EndoV. Digestion with lambda exonuclease now removes all fragments of DNA except the labeled fragment and adjacent unique gene-specific sequences. These fragments are hybridized to an array of sequential 50-mers across the gene sequence. In a third variation, the 3'OH end is tailed with terminal transferase as above, and the newly generated fragment is PCR amplified with gene-specific primers that are encoded with zipcode sequences. This allows for detection of fragments on a universal array (FIGS. 11 and 12).

Three alternative approaches may be used for generating dozens to hundreds to thousands of heteroduplexed DNA fragments for array detection: (i) fragments amplified individually in 96 or 384 micro-well plates and then pooled; (ii) fragments amplified in groups using the gene-specific/universal primers as described above; and (iii) PCR amplified control fragments hybridized directly to genomic DNA or genomic DNA that has undergone a few rounds of amplification. The first approach has the advantage of being able to control the amount and quality of PCR amplified fragment for each region being queried. The second approach has the advantage of reducing the number of PCR reactions while still generating good yields for each fragment.

The third approach for generating heteroduplexed DNA has the possible pitfall of obtaining hybridizations from gene family members that subsequently lead to false signal. For this reason, a few rounds of PCR amplification with primers to intronic regions unique to the correct gene is favored, while recognizing the caveat that PCR amplification increases the risk of generating spurious background mutations. If PCR errors create too high a background for chip-based detection, the excess normal strand may be generated from a clone. As an alternative, a unique restriction site adjacent to the test gene and a linker capture procedure may be used as described above. The third approach may be modified to include a representational amplification of either genomic or cDNA sample. A number of representations would be analyzed separately to avoid cross hybridization of family members, with the assumption that family members from closely related genes (i.e. K-ras, H-ras, and N-ras) would be in different representations. Protein such as RecA, ssb, and hnRNP or reagents such as cationic detergents known to accelerate DNA hybridization may also be used (Pontius, B. W., et al., *Proc Natl Acad Sci USA*, 88(18):8237-41 (1991), Pontius, B. W., et al., *Proc Natl Acad Sci USA*, 87(21):8403-7 (1990) which are hereby incorporated by reference in their entirety).

Capturing EndoV PCR Amplified Products on Tiled Gene-Specific Arrays.

The first scheme is based on capturing and amplifying unique DNA containing the site of the mutation through a newly generated 3'OH end. Heteroduplexed DNA is formed, and DNA preferentially nicked one base to the 3' side of mismatches using thermostable Endonuclease V (FIG. 8). Thermostable ligase is added to reseal background nicks at perfect match regions. The endonuclease and ligation reactions may be performed in a single step. The newly generated 3'OH is tailed (e.g. with dGTP) using terminal transferase. A set of 12 poly dC8 primers containing 2 unique bases on the 3' end (AA, AG, AT, CA, CG, CT, GA, GG, GT, TA, TG, TT), unique identifier sequences (E1-E12), and a universal sequence (Un1) on the 5' end are added, and hybridized primers extended with Taq DNA polymerase. Use of 2 unique bases on the 3' strand provides specificity in extension on the template that may be difficult to achieve with a primer ending in polydC, as well as providing a scoring for a particular base present at the mismatch. The extension products are PCR amplified with gene-specific upstream primer containing a universal sequence (Un2) on the 5' end, phosphorylated Un2 primer, and fluorescently-labeled Un1 primer, using Taq DNA polymerase and dNTP's containing a low concentration of dUTP. Incorporation of uracil into the PCR products allows use of Endonuclease V to nick the DNA. Nicked PCR products are subsequently digested from the 5' end using lambda exonuclease. Only the 5' labeled single-stranded fragment containing approximately 20 to 50 bases of gene-specific sequence adjacent to and including the site of mismatch will remain. This is necessary to generate a small fragment containing a label that can be localized to a defined region of sequential complementary oligonucleotides (i.e. 50-60 base long oligonucleotides) that tile the length of the exon fragments. Labeled fragments are hybridized on an array containing tiling of gene sequences to identify approximate position of mismatch. A separate procedure with opposite strand primers would be performed on an array containing complementary sequences to determine presence of mismatches on the complementary strand.

The procedure may be expanded to include multiple regions (i.e. exons) of a target sequence (FIG. 9). Here, multiple nicked sites may be tailed with terminal transferase and extended with poly dC containing extension primers. The extension products are PCR amplified with multiple gene-specific upstream primer containing a universal sequence (Un2) on the 5' end, phosphorylated Un2 primer, and fluorescently labeled Un1 primer, using Taq DNA polymerase and dNTP's. Blocking oligonucleotides just upstream of each gene-specific primer are used to assure that the desired PCR products are the dominant products. The PCR products are rendered single-stranded with lambda exonuclease and then hybridized on an array containing tiling of gene sequences (i.e. exons) to identify which regions (i.e. exons) contain mismatches.

When using Endonuclease V to nick the DNA (as in FIG. 8), it may be advantageous to use a label reporter group that is not easily cleaved by EndoV. Alternative approaches for generating the labeled single-stranded fragment containing 20 to 50 bases would not require incorporation of dUTP during the PCR step. These include treating the PCR products with limiting amounts of DNaseI, or incorporating low levels of ribonucleotides and treating with heat or base.

The mutation containing fragment(s) may be sequenced individually from the PCR products, by re-amplifying with a gene-specific primer and a primer containing unique E1 and Un1 sequence. (Other amplifications would use primers with unique E2-E12 sequences on the 3' end of a Un1 sequence.) Alternatively, the set of 12 poly dC primers containing 2 unique bases on the 3' end could contain 12 unique zipcodes on the 5' end. The fragment is PCR amplified via one of 12 zipcode primers (either blocked or not phosphorylated on the 5' end) and a phosphorylated upstream gene-specific primer. After fragmentation with EndoV and digestion, the 5' fragment containing the gene-specific sequence and the zip-code sequence is hybridized to the tiled array. The zipcode sequence provides a unique region that may capture a complementary oligonucleotide containing a reporter group. The reporter group may be labeled with a fluorescent dye, with a unique quantum dot (i.e. Q-dot), or labeled with a combination of fluorescent groups or Q-dots such that all 12 possible zipcode sequences corresponding to the 12 different 2 base combinations would be distinguished. The advantage of identifying the precise two bases at the mutation site is: (i) improved signal-to-noise in distinguishing authentic mutation from background cleavage; (ii) improved ability to distinguish mutation from common polymorphism within the adjacent 50 bases; and (iii) ability to determine zipcode sequences to use for subsequent PCR amplification and sequencing.

Alternative detection motifs, such as tagging the 3'OH end with amino-allyl deoxyuridine (Sigma), for subsequent coupling to monofunctional NHS-ester Cy3 or Cy5 may be used. Recently developed signal amplification of targets hybridized to microarrays may obviate the need for the zipcode-PCR steps. Such commercially available methods include biotinylation of target, staining with streptavidin phycoerythrin (SAPE), staining with antibody cross-linked with biotin, and a second SAPE staining (Affymetrix), as well as 3D dendrimer labeling systems (Genisphere). The 3D dendrimer labeling system may be modified to take advantage of unique zipcode sequences. Zipcode complements may also be labeled with Q-dots. Such Q-dot labeling may either use 12 individual and uniquely fluorescing Q-dots, or a smaller number of Q-dots used in combinations that allow unambiguous distinction of any combination of the 12 signals. It was also noted that in these schemes, fragmentation may be achieved by incorporating a chain terminator such as a dideoxynucleotide, such that the average extension product length, including the zipcode primer, is about 50 bases.

The second scheme is based on capturing and amplifying unique DNA adjacent to the site of the mutation through a newly generated 5' phosphate end (FIG. 10). Heteroduplexes are cleaved with EndoV and background nicks resealed with ligase. The endonuclease and ligation reactions may be performed in a single step. Subsequently, downstream gene-specific primer(s) are annealed and extended to create blunt end with newly generated 5' phosphate. Linker containing Un1 sequence is ligated onto the blunt end with T4 ligase. Fragments are PCR amplified with gene-specific downstream primer containing a universal sequence (Un2) on the 5' end, phosphorylated Un2 primer, and fluorescently labeled Un1 primer, using Taq DNA polymerase, and dNTP's containing a low concentration of dUTP. Incorporation of uracil into the PCR products allows use of Endonuclease V to nick the DNA. Subsequently, the nicked PCR products are digested from the 5' end using lambda exonuclease. Only the 5' labeled single-stranded fragment containing approximately 20 to 50 bases of gene-specific sequence one base beyond the site of mismatch will remain. Labeled fragments are hybridized on an array containing tiling of gene sequences to identify approximate position of mismatch. The fragments may also be identified through the alternative labeling schemes outlined above.

A second set of primers and complementary arrays would be used to detect cleavage events on the opposite strand for each fragment. This is required to assure detection of mutations especially when one strand is refractory to cleavage, as is observed for about 50% of the sites using wild-type EndoV.

For amplification of either a newly generated 3'OH or 5' phosphate, there is the risk of amplifying either very short or almost full-length fragments that occur as a consequence of EndoV cleavage near the ends. False signal may be reduced by use of gene-specific primers 20-60 bp from either end. Further, PNA (peptide nucleotide analogue), or 2'-o-methyl groups, and/or 5-propinyl-dU and 5-propinyl-dC containing oligonucleotides may be used to block amplification of almost full-length strands, that would lead to undesired amplicons.

Capturing EndoV PCR Amplified Products on Universal Zipcode Arrays

The third scheme is based on capturing and amplifying zip-code encoded DNA containing the site of the mutation through a newly generated 3'OH end (FIGS. 11 and 12).

Heteroduplexed DNA is formed, and the DNA is preferentially nicked one base to the 3' side of mismatches using thermostable Endonuclease V. Thermostable ligase is added to reseal background nicks at perfect match regions. The endonuclease and ligation reactions may be performed in a single step. The newly generated 3'OH is tailed (e.g. with dGTP) using terminal transferase. A set of 12 poly dC primers containing 2 unique bases on the 3' end (AA, AG, AT, CA, CG, CT, GA, GG, GT, TA, TG, TT), unique identifier sequences (E1-E12), and a universal sequence (Un1) on the 5' end are added, and hybridized primers extended with Taq DNA polymerase. Use of 2 unique bases on the 3' strand provides specificity in extension on the template that may be difficult to achieve with a primer ending in polydC, as well as provides a scoring for a particular base present at the mismatch. PCR amplification is carried out with a gene-specific upstream primer containing a zipcode sequence and a universal sequence (Un2) on the 5' end, phosphorylated Un2 primer, and fluorescently labeled Un1 primer, using Taq DNA polymerase and dNTP's. Multiple primers with different zipcode sequences are available, but the shortest PCR product possible at a given position dominates. PCR products are then digested from the 5' end using lambda exonuclease. Only the 5' labeled single-stranded fragment containing gene-specific sequence adjacent to and including the site of mismatch will remain. Labeled fragments are hybridized on a universal array containing zipcode sequences to identify approximate position of mismatch. A separate procedure with opposite strand primers would be performed to determine the presence of mismatches on the complementary strand.

The mutation containing fragment(s) may be sequenced individually from the PCR products, by re-amplifying with the specific zipcode primer and a primer containing unique E1 and Un1 sequence. (Other amplifications would use primers with unique E2-E12 sequences on the 3' end of a Un1 sequence.) Alternatively, the set of 12 poly dC primers containing 2 unique bases on the 3' end could contain 12 unique zipcodes (Q-zips, separate and compatible with those used on the array) on the 5' end. The fragment is PCR amplified via one of 12 Q-zip primers (either blocked or not phosphorylated on the 5' end) and a phosphorylated upstream gene-specific primer containing a zipcode sequence and a universal sequence (Un2) on the 5' end, phosphorylated Un2 primer. After fragmentation with EndoV and digestion, the 5' fragment containing the gene-specific sequence and the zip-code sequence is hybridized to the universal array. The Q-zip sequence provides a unique region that may capture a complementary oligonucleotide containing a reporter group. The reporter group may be labeled with a fluorescent dye, with a unique Q-dot, or labeled with a combination of fluorescent groups or Q-dots such that all 12 possible Q-zip sequences corresponding to the 12 different 2 base combinations would be distinguished. The advantage of identifying the precise two bases at the mutation site is: (i) improved signal-to-noise in distinguishing authentic mutation from background cleavage; (ii) improved ability to distinguish mutation from common polymorphism within the adjacent 50 bases; and (iii) the ability to determine zipcode sequences to use for subsequent PCR amplification and sequencing.

One major advantage of using the array format is that multiple regions of the same fragment may be scored at the same time. Further, use of multiple gene-specific primers allows for scoring of mutations in the presence of common known polymorphisms, as illustrated in FIG. 12. In this example, gene-specific primers, containing a zipcode sequence and a universal sequence (Un2), are designed to cover the important target regions at a spacing of 50 to 100 bases. Blocking oligonucleotides, composed of PNA (peptide nucleotide analogue), or 2'-o-methyl groups, and/or 5-propinyl-dU and 5-propinyl-dC containing oligonucleotides, are designed to hybridize just downstream from the gene-specific binding sites. This assures that the desired shorter PCR products dominate. When a known polymorphism is present in the target sequence, allele-specific primers containing different zipcode sequences and the same universal sequence (Un2) are used. If a sample is heterozygous at a given position (i.e. G, A), and then contains a nearby downstream mutation (i.e. G→dA), the following 16 heteroduplexes could form (1) G:C, G:C; (2) G/T, G:C; (3) G:C, G/T; (4) G/T, G/T; (5) G:C, A/C; (6) G/T, A/C; (7) G:C, A:T; (8) G/T, A:T; (9) A/C, G:C; (10) A:T, G:C; (11) A/C, G/T; (12) A:T, G/T; (13) A/C, A/C; (14) A:T, A/C; (15) A/C, A:T; and (16) A:T, A:T. Depending on the base adjacent to the new mutation, it may be difficult to score. However, if two allele-specific PCR primers are used at the position of the upstream polymorphism, then heteroduplexes 3, 5, 12, and 14 would be able to score the presence of the mutation. If the mutation is present in the G allele chromosome, then heteroduplexes 3 and 5 would allow for scoring of the mutation. If the mutation is present in the A allele chromosome, then heteroduplexes 12 and 14 would allow for scoring of the mutation. If the mutation is slightly upstream of the polymorphism, then primers designed to score the complementary strand (i.e., the mutation is now downstream of the polymorphism) would be used.

When using multiple zipcode encoded gene-specific primers and adjacent blocking groups, there is a risk of "blind spots" i.e. regions where a mutation may be missed because it is within the same sequence used by a given gene-specific primer containing a zipcode, so the primer does not extend that cleavage product. The upstream zipcode encoded gene-specific primer may also not work, as the blocking oligonucleotide would still block amplification of sequences directly adjacent to the blocking sequence. This potential problem is addressed by dividing the gene to be tested into multiple consecutive regions. A first multiplexed PCR reaction amplifies potential mutations in the odd numbered regions, while a second multiplexed PCR reaction amplifies potential mutations in the even numbered regions. This allows for use of primers that generate fragments that may contain some overlaps, such that large exon sequences are still fully covered in either the even or odd set of PCR products. An additional two sets of multiplexed PCR reactions cover sequences on the lower strand. The two sets for each strand are designed such that each set covers the "blind spots" for the other set.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method for identifying one or more mutant nucleotide target sequences differing by one or more single-base changes, insertions, or deletions, from one or more normal nucleotide target sequences, said method comprising:

providing one or more sample(s) potentially containing the normal nucleotide target sequences, one or more mutant nucleotide target sequences, or both;

providing a group of one or more primary oligonucleotide primer sets, each set comprising (a) a first primary oligonucleotide primer, having a target-specific portion and a 5' upstream secondary primer-specific portion and (b) a second primary oligonucleotide primer, having a target-specific portion and a 5' upstream secondary primer-specific portion, wherein the first primary oligonucleotide primers of each set in a group contain the same 5' upstream secondary primer-specific portion and the second oligonucleotide primers of each set in a group contain the same 5' upstream secondary primer-specific portion;

blending the sample, the one or more primary oligonucleotide primer sets, and a polymerase to form one or more primary polymerase chain reaction mixture(s);

subjecting the one or more primary polymerase chain reaction mixture(s) to one or more polymerase chain reaction cycles to form primary extension products complementary to the normal nucleotide and mutant nucleotide target sequences present in the sample;

providing a group of one or more secondary oligonucleotide primer sets, each set comprising (a) a first secondary oligonucleotide primer which comprises the same sequence as the 5' upstream secondary primer-specific portion of the first primary oligonucleotide primer and (b) a second secondary oligonucleotide primer which comprises the same sequence as the 5' upstream secondary primer-specific portion of the second primary oligonucleotide primer;

blending the one or more primary polymerase chain reaction mixture(s), the one or more secondary oligonucleotide primer sets, and a polymerase to form one or more secondary polymerase chain reaction mixture(s);

subjecting the one or more secondary polymerase chain reaction mixture(s) to one or more polymerase chain reaction cycles to form secondary extension products complementary to the primary extension products;

inactivating the polymerase;

subjecting the one or more secondary polymerase chain reaction mixture(s) to a process which converts the secondary extension products to a single-stranded form and anneals the single-stranded secondary extension products to form heteroduplexed products potentially comprising nucleic acid molecules which include nucleotide sequences from the normal nucleotide target sequence and from the mutant nucleotide target sequence;

providing an endonuclease, which preferentially nicks or cleaves heteroduplexed DNA at a location within one base away from mismatched base pairs;

blending the heteroduplexed products and the endonuclease to form an endonuclease cleavage reaction mixture;

subjecting the endonuclease cleavage reaction mixture to an endonuclease cleavage reaction so that the endonuclease preferentially nicks or cleaves heteroduplexed products at a location within one base away from mismatched base pairs;

providing a ligase;

blending the endonuclease cleavage reaction mixture and the ligase to form a ligase resealing reaction mixture;

subjecting the ligase resealing reaction mixture to a ligase resealing reaction to seal the nicked heteroduplexed products at perfectly matched base pairs but with substantially no resealing of nicked heteroduplexed products at locations adjacent to mismatched base pairs;

separating products after said subjecting the ligase resealing reaction mixture to a ligase resealing reaction by size or electrophoretic mobility or hybridization to capture probes attached to a solid support; and detecting the presence of the normal nucleotide target sequence and the one or more mutant nucleotide target sequence in the sample by distinguishing the separated products.

2. The method according to claim 1, wherein one or both of the secondary oligonucleotide primers are provided with a label.

3. The method according to claim 2, wherein a first secondary polymerase chain reaction is carried out with a first secondary oligonucleotide primer which is labeled and one or more second secondary oligonucleotide primers which are unlabeled, and a second secondary polymerase chain reaction is carried out with a second secondary oligonucleotide primer which labeled and one or more first secondary oligonucleotide primers which are unlabeled.

4. The method according to claim 2, wherein first and second secondary polymerase chain reactions are carried out with a first secondary oligonucleotide primer which is labeled and one or more second secondary oligonucleotide primers which are unlabeled and third and fourth secondary polymerase chain reactions are carried out with one or more first secondary oligonucleotide primers which are unlabeled and a second secondary oligonucleotide primer which is labeled.

5. The method according to claim 2, wherein a plurality of secondary polymerase chain reaction mixtures comprise a first secondary oligonucleotide primer which is labeled and one or more second secondary oligonucleotide primers which are unlabeled, and a plurality of secondary polymerase chain reaction mixtures comprise a second secondary oligonucleotide primer which is labeled and one or more first secondary oligonucleotide primers which are unlabeled.

6. The method according to claim 1, wherein the process which converts the secondary extension products to a single-stranded form is carried out by digestion with an exonuclease.

7. The method according to claim 1, wherein said method further comprises the following steps after said subjecting the ligase resealing reaction mixture to a ligase resealing reaction and before said separating:

providing a terminal transferase;

blending the potentially nicked or cleaved heteroduplexed products from the ligase resealing reaction mixture and the terminal transferase to form a terminal transferase extension reaction mixture;

incubating the terminal transferase extension reaction mixture with a single dNTP to extend nicked or cleaved heteroduplexed products at newly generated 3' OH groups to form terminal transferase extension products;

providing one or more tertiary oligonucleotide primers suitable for hybridization to the newly generated terminal transferase extension products and suitable for 3' end extension;

blending the terminal transferase extension products, the tertiary oligonucleotide primers, and a polymerase to form a tertiary polymerase extension reaction mixture;

incubating the tertiary polymerase extension reaction mixture under conditions allowing for the tertiary oligonucleotide primers to hybridize to the terminal transferase extension products, and polymerase to produce tertiary extension products, which are complementary copies of said terminal transferase extension products, containing sites of mismatch and adjacent target-specific sequences;

providing a group of one or more quaternary oligonucleotide primer sets, each set characterized by (a) a first quaternary oligonucleotide primer, having a tertiary extension product-specific portion and a 5' upstream quintenary primer-specific portion, (b) a second quaternary oligonucleotide primer, having a tertiary extension product-specific portion and a 5' upstream quintenary primer-specific portion;

blending the tertiary extension products, the quaternary oligonucleotide primers, and a polymerase to form one or more quaternary extension reaction mixture(s);

subjecting the one or more quaternary polymerase chain reaction mixture(s) to one or more quaternary polymerase chain reaction cycles to form an quaternary extension product;

providing a group of one or more quintenary oligonucleotide primer sets, each set characterized by (a) a first quintenary oligonucleotide primer having the same sequence as the 5' upstream portion of the first quaternary oligonucleotide primer, and (b) a second quintenary oligonucleotide primer containing the same sequence as the 5' upstream portion of the second quaternary oligonucleotide;

blending the quaternary extension product, the group of one or more quintenary oligonucleotide primer sets, and a polymerase to form a quintenary polymerase chain reaction mixture(s); and subjecting the quintenary polymerase chain reaction mixture(s) to one or more quintenary polymerase chain reaction cycles to form quintenary extension product complementary to the quaternary extension product, wherein the quintenary extension product is subjected to said separating.

8. The method according to claim 7, wherein the tertiary oligonucleotide primers contain either: (1) 2 unique bases on their 3' end, followed by a mononucleotide repeat sequence complementary to the dNTP used in the terminal transferase extension reaction, and a 5' upstream secondary primer-specific portion or (2) additional unique mutation identifier sequences that correspond to the 2 unique bases on their 3' ends.

9. The method according to claim 8, further comprising;
providing a solid support with different capture oligonucleotides immobilized at different sites on the solid support, wherein the capture oligonucleotides have nucleotide sequences complementary to tertiary extension product-specific portions and
contacting the quintenary polymerase chain reaction mixture(s) with the solid support under conditions effective to hybridize the quintenary extension products to the capture oligonucleotides in a base-specific manner, wherein said detecting indicates the presence of quintenary extension product captured using the tertiary extension product-specific portions and immobilized to the solid support at particular sites, thereby indicating the presence of one or more mutant nucleotide target sequences in the sample.

10. The method according to claim 9, wherein the tertiary oligonucleotide primers contain additional unique mutation identifier sequences that correspond to the 2 unique bases on their 3' ends.

11. The method according to claim 10 further comprising:
fragmenting the quintenary extension product to generate fragments containing unique target-specific sequences of average length of 20-50 bases.

12. The method according to claim 11, further comprising:
providing a solid support with different capture oligonucleotides immobilized at different sites on the solid support, wherein the capture oligonucleotides have nucleotide sequences complementary to tertiary extension product-specific portions and
contacting the quintenary polymerase chain reaction mixture(s), after said fragmenting, with the solid support under conditions effective to hybridize the fragmented quintenary extension product to the capture oligonucleotides in a base-specific manner, wherein said detecting indicates the presence of fragmented quintenary extension product captured using the tertiary extension product-specific portions and immobilized to the solid support at particular sites, thereby indicating the presence of one or more mutant nucleotide target sequences in the sample.

13. The method according to claim 10, wherein the first quaternary oligonucleotide primer in each set contains a unique addressable array specific portion.

14. The method according to claim 13 further comprising:
providing a solid support with different capture oligonucleotides immobilized at different sites on the solid support, wherein the capture oligonucleotides have nucleotide sequences complementary to the addressable array-specific portions and
contacting the quintenary polymerase chain reaction mixture(s) with the solid support under conditions effective to hybridize the quintenary extension product to the capture oligonucleotides in a base-specific manner, wherein said detecting indicates the presence of quintenary extension product captured using the addressable array-specific portions and immobilized to the solid support at particular sites, thereby indicating the presence of one or more mutant nucleotide target sequences in the sample.

15. The method according to claim 1, wherein said method further comprises the following steps after said subjecting the ligase resealing reaction mixture to a ligase resealing reaction and before said separating:
providing one or more tertiary oligonucleotide primers suitable for hybridization to the 5' end of a strand of the nicked heteroduplex products which have been sealed;
blending the ligase resealing reaction mixture after resealing, the tertiary oligonucleotide primers, and a polymerase to form a tertiary polymerase extension reaction mixture;
incubating the tertiary polymerase extension reaction mixture under conditions allowing for the tertiary oligonucleotide primers to hybridize to the strand of the nicked heteroduplex products which have been sealed, and a polymerase to produce tertiary extension products;
providing a blunt end linker;
providing a ligase with blunt end activity;
blending the tertiary extension products, the blunt end linker, and the ligase with blunt end activity to form a blunt end ligase reaction mixture;
incubating the blunt end ligase reaction mixture under conditions effective to ligate the blunt end linker to tertiary extension products and produce blunt end ligation products;
providing a plurality of quaternary oligonucleotide primer sets, each set characterized by (a) a first quaternary oligonucleotide primer, having a blunt end ligation product-specific portion and a 5' upstream quinternary primer-specific portion, (b) a second quaternary oligonucleotide primer, having a linker-specific portion;
blending the blunt end ligation products, the quaternary oligonucleotide primer sets, and a polymerase to form one or more quintenary polymerase chain reaction mixture(s);
subjecting the one or more quaternary polymerase chain reaction mixture(s) to one or more polymerase chain reaction cycles to form a quaternary extension product;
providing a quintenary oligonucleotide primer having the same sequence as the 5' upstream portion of a first quaternary oligonucleotide primer;
blending the quintenary oligonucleotide primer, quaternary polymerase extension product, and a polymerase to for quintenary polymerase chain reaction mixture; and
subjecting the one or more quintenary polymerase chain reaction mixture to one or more polymerase chain reaction cycles to form a quintenary extension product, wherein the quintenary extension product is subjected to said separating.

16. The method according to claim 15 further comprising:
fragmenting the quintenary extension products to generate fragments containing unique tertiary extension product-specific sequences of average length of 20-50 bases.

17. The method according to claim 16 further comprising:
providing a solid support with different capture oligonucleotides immobilized at different sites on the solid support, wherein the capture oligonucleotides have nucleotide sequences complementary to tertiary extension product-specific portions and
contacting the quintenary polymerase chain reaction mixture(s), after said fragmenting, with the solid support under conditions effective to hybridize the fragmented quintenary extension product to the capture oligonucleotides in a base-specific manner, wherein said detecting indicates the presence of fragmented quintenary extension product captured using the tertiary extension product-specific portions and immobilized to the solid support at particular sites, thereby indicating the presence of one or more mutant nucleotide sequences in the sample.

18. A method for identifying one or more mutant nucleotide target sequences differing by one or more single-base changes, insertions, or deletions, from one or more normal nucleotide target sequences, said method comprising:

providing one or more sample(s) potentially containing the normal nucleotide target sequence, one or more mutant nucleotide target sequences, or both;
providing a group of one or more primary oligonucleotide primer sets, each set characterized by (a) a first oligonucleotide primer, having a target-specific portion, and (b) a second oligonucleotide primer, having a target-specific portion, wherein only one of the primary oligonucleotide primers is provided with a label;
providing a polymerase;
blending the sample, the primary oligonucleotide primer sets, and the polymerase to form one or more primary polymerase chain reaction mixture(s);
subjecting the primary polymerase chain reaction mixture to one or more polymerase chain reaction cycles to form primary extension products complementary to the normal nucleotide target sequence and mutant nucleotide target sequences present in the sample;
inactivating the polymerase;
subjecting the primary polymerase chain reaction mixture(s) to a process which converts the primary extension products to a single-stranded form and anneals the single-stranded primary extension products to form heteroduplexed products potentially comprising nucleic acid molecules which include nucleotide sequences from the normal nucleotide target sequence and from the mutant nucleotide target sequences;
providing an endonuclease, which preferentially nicks or cleaves heteroduplexed DNA at a location within one base away from mismatched base pairs;
blending the heteroduplexed products and the endonuclease to form an endonuclease cleavage reaction mixture;
subjecting the endonuclease cleavage reaction mixture to an endonuclease cleavage reaction so that the endonuclease preferentially nicks or cleaves the heteroduplexed products at a location within one base away from mismatched base pairs;
providing a ligase;
blending the endonuclease cleavage reaction mixture and the ligase to form a ligase resealing reaction mixture;
subjecting the ligase resealing reaction mixture to a ligase resealing reaction to seal the nicked heteroduplexed products at perfectly matched base pairs but with substantially no resealing of nicked heteroduplexed products at locations adjacent to mismatched base pairs;
separating products resulting from said subjecting the ligase resealing reaction mixture to a ligase resealing reaction by size or electrophoretic mobility; and
detecting the presence of the normal nucleotide target sequences and the one or more mutant nucleotide target sequences in the sample by distinguishing the separated products resulting from the ligase resealing reaction.

19. The method according to claim 18, wherein a first primary polymerase chain reaction is carried out with a first primary oligonucleotide primer which is labeled and one or more second primary oligonucleotide primers which are unlabeled, and a second polymerase chain reaction is carried out with a second primary oligonucleotide primer which is labeled and one or more first primary oligonucleotide primers which are unlabeled.

20. The method according to claim 18, wherein first and second primary polymerase chain reactions are carried out with a first primary oligonucleotide primer which is labeled and one or more second primary oligonucleotide primers which are unlabeled and third and fourth primary polymerase chain reactions are carried out with one or more first primary oligonucleotide primers which are unlabeled and a second primary oligonucleotide primer which is labeled.

21. The method according to claim 18, wherein a plurality of primary polymerase chain reaction mixtures comprise a first primary oligonucleotide primer which is labeled and one or more second primary oligonucleotide primers which are unlabeled, and a plurality of primary polymerase chain reaction mixtures comprise a second primary oligonucleotide primer which is labeled and one or more first primary oligonucleotide primers which are unlabeled.

22. The method according to claim 18, wherein the process which converts the primary extension products to a single-stranded form is carried out by digestion with an exonuclease.

23. A method for identifying one or more mutant nucleotide target sequences differing by one or more single-base changes, insertions, or deletions, from a normal nucleotide target sequences, said method comprising:
providing one or more sample(s) potentially containing the normal nucleotide target sequences, one or more mutant nucleotide target sequences, or both;
providing a group of one or more primary oligonucleotide primer sets, each set characterized by (a) a first oligonucleotide primer, having a target-specific portion, and (b) a second oligonucleotide primer, having a target-specific portion, wherein only one of the primary oligonucleotide primers is provided with a label;
blending the sample, the primary oligonucleotide primer sets, and a polymerase to form one or more primary polymerase chain reaction mixture(s);
subjecting the primary polymerase chain reaction mixture to one or more polymerase chain reaction cycles to form primary extension products complementary to the normal nucleotide target sequences present in the sample;
inactivating the polymerase;
subjecting the primary polymerase chain reaction mixture(s) to a process which converts the primary extension products to a single-stranded form and anneals the single-stranded primary extension products to form heteroduplexed products potentially comprising nucleic acid molecules which include nucleotide sequences from the normal nucleotide target sequences and from the mutant nucleotide target sequences;
providing an endonuclease, which preferentially nicks or cleaves heteroduplexed DNA at a location within one base away from mismatched base pairs;
blending the heteroduplexed products and the endonuclease to form an endonuclease cleavage reaction mixture;
subjecting the endonuclease cleavage reaction mixture to an endonuclease cleavage reaction so that the endonuclease preferentially nicks or cleaves the heteroduplexed products at a location within one base away from mismatched base pairs;
providing a ligase;
blending the endonuclease cleavage reaction mixture and the ligase to form a ligase resealing reaction mixture;
subjecting the ligase resealing reaction mixture to a ligase resealing reaction to seal the nicked heteroduplexed products at perfectly matched base pairs but with substantially no resealing of nicked heteroduplexed products at locations adjacent to mismatched base pairs;
providing a terminal transferase;
blending the potentially nicked or cleaved heteroduplexed products from the ligase resealing reaction mixture and the terminal transferase to form a terminal transferase extension reaction mixture;

incubating the terminal transferase extension reaction mixture with a single dNTP to extend nicked or cleaved heteroduplexed products at newly generated 3' OH groups to form terminal transferase extension products;

providing one or more tertiary oligonucleotide primers suitable for hybridization to the newly generated terminal transferase extension products and suitable for 3' end extension;

blending the terminal transferase extension products, the tertiary oligonucleotide primers, and a polymerase to form a tertiary polymerase extension reaction mixture;

incubating the tertiary polymerase extension reaction mixture under conditions allowing the tertiary oligonucleotide primers to hybridize to the terminal transferase extension products, and polymerase to produce tertiary extension products, which are complementary copies of said terminal transferase extension products, containing sites of mismatch and adjacent target-specific sequences;

providing a group of one or more quaternary oligonucleotide primer sets, each set characterized by (a) a first quaternary oligonucleotide primer, having a tertiary extension product-specific portion and a 5' upstream quinternary primer-specific portion, and (b) a second quaternary oligonucleotide primer, having a tertiary extension product-specific portion and a 5' upstream quinternary primer-specific portion;

blending the tertiary extension products, the quaternary oligonucleotide primers, and a polymerase to form one or more quaternary extension reaction mixture(s);

subjecting the one or more quaternary polymerase chain reaction mixture(s) to one or more quaternary polymerase chain reaction cycles to form a quaternary extension product;

providing a group of one or more quinternary oligonucleotide primer sets, each set characterized by (a) a first quinternary oligonucleotide primer, having the same sequence as the 5' upstream portion of the first quaternary oligonucleotide primer, and (b) a second quinternary oligonucleotide primer, containing the same sequence as the 5' upstream portion of the second quaternary oligonucleotide, blending the quaternary extension product, the group of one or more quinternary oligonucleotide primer sets, and a polymerase to form a quinternary polymerase chain reaction mixture(s);

subjecting the quinternary polymerase chain reaction mixture(s) to one or more quinternary polymerase chain reaction cycles to form a quinternary extension product complementary to the quaternary extension product;

separating products resulting from said subjecting the ligase resealing reaction mixture to a ligase resealing reaction by size or electrophoretic mobility or hybridization to capture probes attached to a solid support; and detecting the presence of the normal nucleotide target sequences and the one or more mutant nucleotide target sequences in the sample by distinguishing the separated products resulting from the ligase resealing reaction.

24. The method according to claim 23, wherein the endonuclease cleavage and ligase resealing reactions are carried out simultaneously.

25. The method according to claim 23, wherein the tertiary oligonucleotide primers contain 2 unique bases on their 3' end, followed by a mononucleotide repeat sequence complementary to the dNTP used in the terminal transferase extension reaction, and a 5' upstream secondary primer-specific portion.

26. The method according to claim 25 further comprising: fragmenting the quinternary extension product to generate fragments containing unique target-specific sequences of average length of 20-50 bases.

27. The method according to claim 26 further comprising: providing a solid support with different capture oligonucleotides immobilized at different sites on the solid support, wherein the capture oligonucleotides have nucleotide sequences complementary to tertiary extension product-specific portions and contacting the quinternary polymerase chain reaction mixture(s), after said fragmenting, with the solid support under conditions effective to hybridize the fragmented quinternary extension product to the capture oligonucleotides in a base-specific manner, wherein said detecting indicates the presence of fragmented quinternary extension product captured using the tertiary extension product-specific portions and immobilized to the solid support at particular sites, thereby indicating the presence of one or more mutant target nucleotide sequences in the sample.

28. The method according to claim 25, wherein the first quaternary oligonucleotide primer in each set contains a unique addressable array specific portion.

29. The method according to claim 28, wherein the second quinternary oligonucleotide primer is labeled.

30. The method according to claim 28 further comprising: providing a solid support with different capture oligonucleotides immobilized at different sites on the solid support, wherein the capture oligonucleotides have nucleotide sequences complementary to the addressable array-specific portions and contacting the quinternary polymerase chain reaction mixture(s) with the solid support under conditions effective to hybridize the quinternary extension product to the capture oligonucleotides in a base-specific manner, wherein said detecting indicates the presence of quinternary extension product captured using the addressable array-specific portions and immobilized to the solid support at particular sites, thereby indicating the presence of one or more mutant target nucleotide sequences in the sample.

31. A method for identifying one or more mutant nucleotide target sequences differing by one or more single-base changes, insertions, or deletions, from a normal nucleotide target sequences, said method comprising:

providing one or more sample(s) potentially containing the normal nucleotide target sequences, one or more mutant nucleotide target sequences, or both;

providing a group of one or more primary oligonucleotide primer sets, each set characterized by (a) a first oligonucleotide primer, having a target-specific portion, and (b) a second oligonucleotide primer, having a target-specific portion, wherein only one of the primary oligonucleotide primers is provided with a label;

providing a polymerase;

blending the sample, the primary oligonucleotide primer sets, and the polymerase to form one or more primary polymerase chain reaction mixture(s);

subjecting the primary polymerase chain reaction mixture to one or more polymerase chain reaction cycles to form primary extension products complementary to the normal target and mutant nucleotide target sequences present in the sample;

inactivating the polymerase;

subjecting the primary polymerase chain reaction mixture(s) to a process which converts the primary extension products to a single-stranded form and anneals the single-stranded primary extension products to form heteroduplexed products potentially comprising nucleic acid molecules which include nucleotide sequences from the normal nucleotide target sequences and from the mutant nucleotide target sequences;

providing an endonuclease, which preferentially nicks or cleaves heteroduplexed DNA at a location within one base away from mismatched base pairs;

blending the heteroduplexed products and the endonuclease to form an endonuclease cleavage reaction mixture;

subjecting the endonuclease cleavage reaction mixture to an endonuclease cleavage reaction so that the endonuclease preferentially nicks or cleaves the heteroduplexed products at a location within one base away from mismatched base pairs;

providing a ligase;

blending the endonuclease cleavage reaction mixture and the ligase to form a ligase resealing reaction mixture;

subjecting the ligase resealing reaction mixture to a ligase resealing reaction to seal the nicked heteroduplexed products at perfectly matched base pairs but with substantially no resealing of nicked heteroduplexed products at locations adjacent to mismatched base pairs;

providing one or more tertiary oligonucleotide primers suitable for hybridization to the 5' end of a strand of the nicked heteroduplex products which have been sealed;

blending the ligase resealing reaction mixture after resealing, the tertiary oligonucleotide primers, and a polymerase to form a tertiary polymerase extension reaction mixture;

incubating the tertiary polymerase extension reaction mixture under conditions allowing for the tertiary oligonucleotide primers to hybridize to strand of the nicked heteroduplex products which have been sealed, and the polymerase to produce tertiary extension products;

providing a blunt end linker;

providing a ligase with blunt end activity;

blending the tertiary extension products, the blunt end linker, and the ligase with blunt end activity to form a blunt end ligase reaction mixture;

incubating the blunt end ligase reaction mixture under conditions effective to ligate the blunt end linker to tertiary extension products and produce blunt end ligation products;

providing a plurality of quaternary oligonucleotide primer sets, each set characterized by (a) a first quaternary oligonucleotide primer, having a blunt end ligation product-specific portion and a 5' upstream quinternary primer-specific portion, and (b) a second quaternary oligonucleotide primer, having a linker-specific portion;

blending the blunt end ligation products, the quaternary oligonucleotide primer sets, and a polymerase to form one or more quaternary polymerase chain reaction mixture(s);

subjecting the one or more quaternary polymerase chain reaction mixture(s) to one or more polymerase chain reaction cycles to form a quaternary extension product;

providing a quinternary oligonucleotide primer having the same sequence as the 5' upstream portion of a first quaternary oligonucleotide primer;

blending the quinternary oligonucleotide primer, quaternary polymerase extension product, and a polymerase to form a quinternary polymerase chain reaction mixture;

subjecting the one or more quinternary polymerase chain reaction mixture to one or more polymerase chain reaction cycles to form a quinternary extension product;

separating products resulting from said subjecting the one or more quinternary polymerase chain reaction mixture to one or more polymerase chain reaction cycles by size or electrophoretic mobility or hybridization to capture probes attached to a solid support; and detecting the presence of the normal nucleotide target sequences and the one or more mutant nucleotide target sequences in the sample by distinguishing the separated products resulting from the quinternary polymerase chain reaction.

32. The method according to claim 31 further comprising:

fragmenting the quinternary extension products to generate fragments containing unique tertiary extension product-specific sequences of average length of 20-50 bases.

33. The method according to claim 32, further comprising:

providing a solid support with different capture oligonucleotides immobilized at different sites on the solid support, wherein the capture oligonucleotides have nucleotide sequences complementary to tertiary extension product-specific portions and contacting the quinternary polymerase chain reaction mixture(s), after said fragmenting, with the solid support under conditions effective to hybridize the fragmented quinternary extension product to the capture oligonucleotides in a base-specific manner, wherein said detecting indicates the presence of fragmented quinternary extension product captured using the tertiary extension product-specific portions and immobilized to the solid support at particular sites, thereby indicating the presence of one or more mutant target nucleotide sequences in the sample.

* * * * *